US010065956B2

United States Patent
Biemans et al.

(10) Patent No.: US 10,065,956 B2
(45) Date of Patent: Sep. 4, 2018

(54) ETHYNYL DERIVATIVES

(71) Applicant: Hoffmann-La Roche Inc., Little Falls, NJ (US)

(72) Inventors: Barbara Biemans, Basel (CH); Wolfgang Guba, Muelheim (DE); Georg Jaeschke, Basel (CH); Jean-Marc Plancher, Hagenthal-le-Bas (FR); Antonio Ricci, Birsfelden (CH); Daniel Rueher, Raedersdorf (FR); Eric Vieira, Frenkendorf (CH); Fionn O'Hara, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/707,848

(22) Filed: Sep. 18, 2017

(65) Prior Publication Data
US 2018/0002333 A1   Jan. 4, 2018

Related U.S. Application Data

(63) Continuation of application No. PCT/EP2016/055487, filed on Mar. 15, 2016.

(30) Foreign Application Priority Data

Mar. 19, 2015   (EP) .................................... 15159868

(51) Int. Cl.
| C07D 471/04 | (2006.01) |
| C07D 417/04 | (2006.01) |
| C07D 413/04 | (2006.01) |
| C07D 405/14 | (2006.01) |
| C07D 403/04 | (2006.01) |

(52) U.S. Cl.
CPC ......... *C07D 471/04* (2013.01); *C07D 403/04* (2013.01); *C07D 405/14* (2013.01); *C07D 413/04* (2013.01); *C07D 417/04* (2013.01)

(58) Field of Classification Search
CPC .......................... C07D 239/22; C07D 239/70; C07D 491/107; C07D 401/04; C07D 487/04; C07D 401/14; C07D 403/04; C07D 471/04
See application file for complete search history.

(56) References Cited

FOREIGN PATENT DOCUMENTS

WO   2015/128307 A1   3/2015

OTHER PUBLICATIONS

ISR of PCT/EP2016/055487 (dated May 3, 2016).

*Primary Examiner* — Kahsay Habte
(74) *Attorney, Agent, or Firm* — Tamara A. Kale

(57) ABSTRACT

The present invention relates to compounds that may be used for the treatment of Parkinson's disease, anxiety, emesis, obsessive compulsive disorder, autism, neuroprotection, cancer, depression and diabetes type 2. Compounds of formula I are representative, where substituents are defined herein:

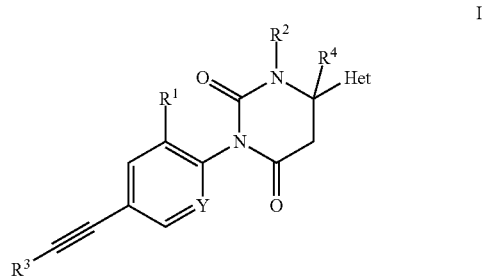

or a pharmaceutically acceptable salt or acid addition salt, a racemic mixture, or its corresponding enantiomer and/or optical isomer and/or stereoisomer thereof.

12 Claims, 1 Drawing Sheet

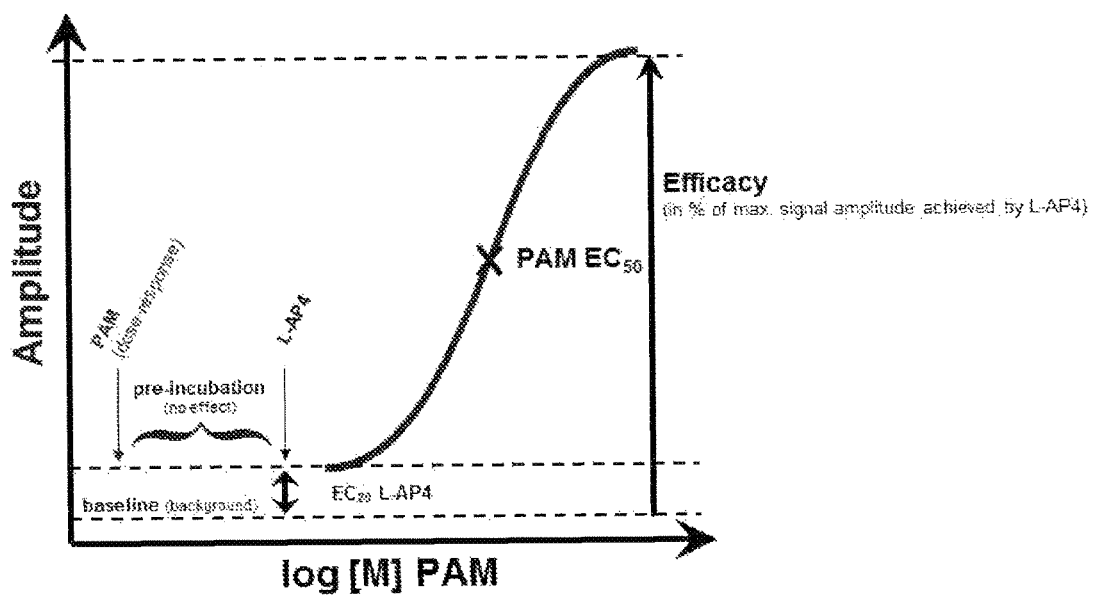

ETHYNYL DERIVATIVES

CROSS REFERENCE TO RELATED APPLICATIONS

This application is a continuation of International Application No. PCT/EP2016/055487, having a filing date of 15 Mar. 2016, which claims benefit under 35 U.S.C. 119 to European Patent Application No. 15159868.7, filed 19 Mar. 2015, the entire contents of each of which are incorporated herein by reference.

The present invention relates to compounds of formula I

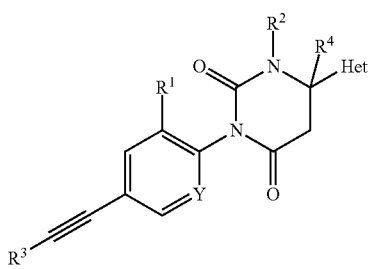

wherein
Y is C—R$^1$;
R$^{1'}$ is hydrogen, F or Cl;
R$^1$ is F or Cl;
R$^2$ is hydrogen or lower alkyl;
R$^3$ is phenyl, pyridinyl or isothiazolyl, wherein the N atom in the pyridinyl group may be in different positions, optionally substituted by one or two halogen atoms;
R$^4$ is hydrogen or lower alkyl;
Het is a 5-membered heteroaryl group, containing two or three heteroatoms, selected from N, O or S, optionally substituted by lower alkyl, cycloalkyl, lower alkoxyalkyl, heterocycloalkyl, wherein the hetero-atom is O, or lower alkyl substituted by hydroxy, or is a bicyclic heteroaromatic ring, containing two or three N-heteroatoms selected from the groups

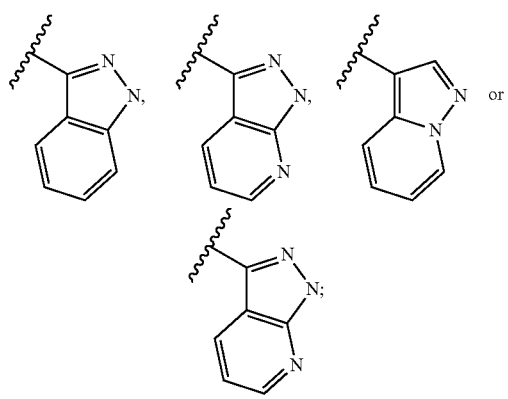

or to a pharmaceutically acceptable salt or acid addition salt, to a racemic mixture, or to its corresponding enantiomer and/or optical isomer and/or stereoisomer thereof.

It has been surprisingly been found that the compounds of general formula I are positive allosteric modulators (PAMs) of metabotropic glutamate receptor 4 (mGluR4).

Metabotropic glutamate receptor 4 is a protein that in humans is encoded by the GRM4 gene.

Together with GRM6, GRM7 and GRM8 it belongs to group III of the Metabotropic glutamate receptor family, and is negatively coupled to adenylate cyclase via activation of the Gαi/o protein. It is expressed primarily on presynaptic terminals, functioning as an autoreceptor or heteroceptor and its activation leads to decreases in transmitter release from presynaptic terminals. mGluR4 is currently receiving much attention based primarily upon its unique distribution and the recent evidence that activation of this receptor plays key modulatory role in many CNS and non-CNS pathways (Celanire S, Campo B, *Expert Opinion in Drug Discovery*, 2012)

The similarity in the ligand binding domains of group III mGluRs creates a challenge for identifying selective orthosteric agonists of this receptor, although some progress has been made in this area. However, targeting positive allosteric modulators (PAMs) rather than orthosteric agonists provides a broader opportunity to identify molecules that are exclusively selective between mGluRs.

mGluR4 PAMs are emerging as promising therapeutic agents for the treatment of motor (and non motor) symptoms as well as a disease-modifying agent in Parkinson's disease through a non-dopaminergic approach.

Parkinson's disease is a progressive neurodegenerative disease that results in the loss of dopaminergic neurons in the substantia nigra (SN). One consequence of the depletion of dopamine in this disease is a series of movement disorders, including bradykinesia, akinesia, tremor, gait disorders and problems with balance. These motor disturbances form the hallmark of PD, although there are many other non-motor symptoms that are associated with the disease. Early in the course of the disease, PD symptoms are effectively treated by dopamine replacement or augmentation, with the use of dopamine D2 receptor agonists, levodopa or monoamine oxidase B inhibitors. However, as the disease progresses these agents become less effective in controlling motor symptoms. Additionally, their use is limited by the emergence of adverse effects including dopamine agonist-induced dyskinesias.

Consequently, there remains a need for new approaches to the treatment of PD that improve the effectiveness of the control of motor symptoms.

Activation of metabotropic glutamate receptor 4 (mGluR4) has been proposed as a potential therapeutic approach to Parkinson's disease. A member of the group III mGluRs, mGluR4 is predominantly a presynaptic glutamate receptor that is expressed in several key locations in the basal ganglia circuits that control movement. Activation of mGluR4 with group III-preferring agonists decreases inhibitory and excitatory post synaptic potentials, presumably by decreasing the release of GABA and glutamate respectively.

The search for novel drugs that relieve motor symptoms of Parkinsonism whilst attenuating the ongoing degeneration of nigrostriatal neurons is of particular interest. Orthosteric mGluR4 agonist L-AP4 has demonstrated neuroprotective effects in a 6-OHDA rodent model of PD and first positive allosteric modulator (−)-PHCCC reduced nigrostriatal degeneration in mice treated with 1-Methyl-4-Phenyl-1,2,3,6-Tetrahydropyridine (MPTP). These studies provide convincing preclinical evidence suggesting that mGluR4 activators constitute a valid approach not only for symptomatic treatments of PD, but also potentially as disease modifiers for this indication.

The neuroprotective effects of selective mGluR4 modulators was also described in *Neuroreport*, 19(4), 475-8, 2008, *Proc. Natl. Acad. Sci, USA,* 100(23), 13668-73, 2003 and *J. Neurosci.* 26(27), 7222-9, 2006 and *Mol. Pharmacol.* 74(5), 1345-58, 2008.

Anxiety disorders are among the most prevalent psychiatric disorders in the world, and are co-morbid with Parkinson's disease (Prediger R, et al. *Neuropharmacology* 2012; 62:115-24). Excessive glutamatergic neurotransmission is one important feature of anxiety pathophysiology. Based on presynaptic localization of mGluR4 in brain areas involved in anxiety and mood disorders, and dampening excessive brain excitability, the mGluR4 activators may represent a new generation of anxiolytic therapeutics (*Eur. J. Pharmacol.,* 498(1-3), 153-6, 2004).

Addex has reported in 2010 that ADX88178 was active in two preclinical rodent models of anxiety: the marble burying test in mice and EPM in mice and rats. ADX88178 also displayed an anxiolytic-like profile in the rat EPM test after oral dosing.

mGluR4 modulators were also shown to exert anti-depressive actions (*Neuropharmacology,* 46(2), 151-9, 2004).

In addition, mGluR4 modulators were also shown to be involved in glucagon secretion inhibition (*Diabetes,* 53(4), 998-1006, 2004). Therefore, orthosteric or positive allosteric modulators of mGluR4 have potential for the treatment of type 2 diabetes through its hypoglycemic effect.

Moreover, mGluR4 was shown to be expressed in prostate cancer cell-line (*Anticancer Res.* 29(1), 371-7, 2009) or colorectal carcinoma (*Cli. Cancer Research,* 11(9)3288-95, 2005). mGluR4 modulators may therefore have also potential role for the treatment of cancers.

Other proposed effects of mGluR4 PAM's can be expected for the treatment of emesis, obsessive compulsive disorder, anorexia and autism.

Compounds of formula I are distinguished by having valuable therapeutic properties. They can be used in the treatment or prevention of disorders, relating to allosteric modulators for the mGluR4 receptor.

The most preferred indications for compounds which are allosteric modulators for the mGluR4 receptor are Parkinson's disease, anxiety, emesis, obsessive compulsive disorder, anorexia, autism, neuroprotection, cancer, depression and type 2 diabetes.

The present invention relates to compounds of formula I and to their pharmaceutically acceptable salts, to these compounds as pharmaceutically active substances, to the processes for their production as well as to their use in the treatment or prevention of disorders, relating to allosteric modulators for the mGluR4 receptor, such as Parkinson's disease, anxiety, emesis, obsessive compulsive disorder, autism, neuroprotection, cancer, depression and diabetes type 2 and to pharmaceutical compositions containing the compounds of formula I.

A further object of the present invention is a method for the treatment or prophylaxis of Parkinson's disease, anxiety, emesis, obsessive compulsive disorder, anorexia, autism, neuroprotection, cancer, depression and type 2 diabetes, which method comprises administering an effective amount of a compound of formula I to a mammal in need.

Furthermore, the invention includes all racemic mixtures, all their corresponding enantiomers and/or optical isomers, or analogues containing isotopes of hydrogen, fluorine, carbon, oxygen or nitrogen.

BRIEF DESCRIPTION OF THE FIGURE

FIG. 1: Illustration of the experimental outline for mGlu4 PAM Ca2+ mobilization screening assay and the determination of $EC_{50}$ and % Emax values.

The following definitions of the general terms used in the present description apply irrespective of whether the terms in question appear alone or in combination.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "cycloalkyl" denotes a cyclic alkyl group with 3 to 6 carbon atoms.

As used herein, the term "lower alkoxy" denotes a lower alkyl group as defined above, which is linked with an O atom.

As used herein, the term "lower alkoxyalkyl" denotes a lower alkoxy group as defined above, which is linked with a lower alkyl group.

The term "5-membered heteroaryl group, containing two or three heteroatoms, selected from N, O or S" encompasses the following groups:

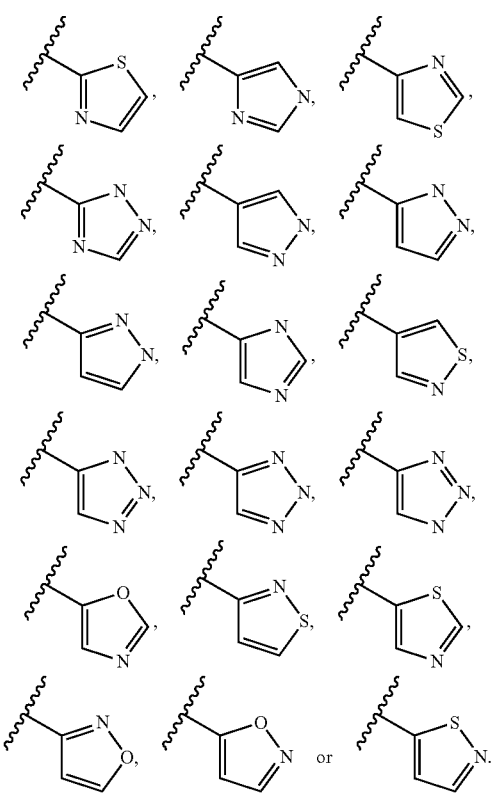

The term "a bicyclic heteroaromatic ring, containing two or three N-heteroatoms" encompasses the following groups:

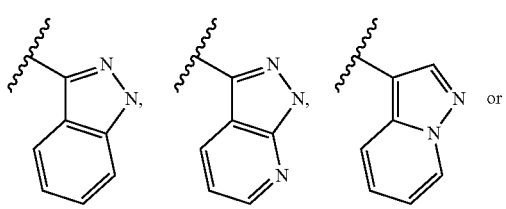

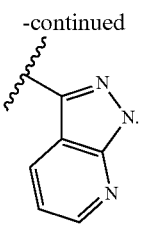

The term "heterocycloalkyl, wherein the hetero-atom is O" denotes a 4 or 5 membered cycloalkyl, wherein one carbon atom is replaced by O, for example oxetan-3-yl or tetrahydrofuran-3-yl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred are compounds of formula I, wherein $R^1$ and $R^{1'}$ are both fluoro.

One embodiment of the invention are compounds of formula IA

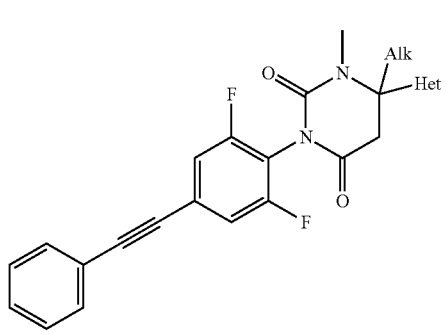

IA

Het is a 5-membered heteroaryl group, containing two or three heteroatoms, selected from N, O or S, optionally substituted by lower alkyl, cycloalkyl, lower alkoxyalkyl, heterocycloalkyl, wherein the hetero-atom is O, or lower alkyl substituted by hydroxy;

Alk is lower alkyl;

or a pharmaceutically acceptable salt or acid addition salt, a racemic mixture, or its corresponding enantiomer and/or optical isomer and/or stereoisomer thereof, for example the following compounds (6S)-3-[2,6-Difluoro-4-(2-phenylethynyl)phenyl]-1,6-dimethyl-6-thiazol-2-yl-hexahydropyrimidine-2,4-dione (6S)-3-[2,6-Difluoro-4-(2-phenylethynyl)phenyl]-1,6-dimethyl-6-(1-methylimidazol-4-yl)hexahydropyrimidine-2,4-dione (6RS)-3-[2,6-Difluoro-4-(2-phenylethynyl)phenyl]-1,6-dimethyl-6-(2-methylthiazol-4-yl)hexahydropyrimidine-2,4-dione (6S)-3-[2,6-Difluoro-4-(2-phenylethynyl)phenyl]-1,6-dimethyl-6-(2-methyl-1,2,4-triazol-3-yl)hexahydropyrimidine-2,4-dione (6S)-3-[2,6-Difluoro-4-(2-phenylethynyl)phenyl]-6-methyl-6-(1-methylpyrazol-4-yl)hexahydropyrimidine-2,4-dione (6S)-3-[2,6-Difluoro-4-(2-phenylethynyl)phenyl]-1,6-dimethyl-6-(1-methylpyrazol-4-yl)hexahydropyrimidine-2,4-dione (6S)-3-[2,6-Difluoro-4-(2-phenylethynyl)phenyl]-1,6-dimethyl-6-(2-methylpyrazol-3-yl)hexahydropyrimidine-2,4-dione (6S)-3-[2,6-Difluoro-4-(2-phenylethynyl)phenyl]-1,6-dimethyl-6-(1H-pyrazol-3-yl)hexahydropyrimidine-2,4-dione (6S)-3-[2,6-Difluoro-4-(2-phenylethynyl)phenyl]-1,6-dimethyl-6-(3-methylimidazol-4-yl)hexahydropyrimidine-2,4-dione (6S)-3-[2,6-Difluoro-4-(2-phenylethynyl)phenyl]-1-ethyl-6-methyl-6-(1-methylpyrazol-4-yl)hexahydropyrimidine-2,4-dione (6S)-3-[2,6-Difluoro-4-(2-phenylethynyl)phenyl]-6-(1-ethylpyrazol-4-yl)-1,6-dimethyl-hexahydropyrimidine-2,4-dione (6S)-3-[2,6-Difluoro-4-(2-phenylethynyl)phenyl]-6-isothiazol-4-yl-1,6-dimethyl-hexahydropyrimidine-2,4-dione (6S)-3-[2,6-Difluoro-4-(2-phenylethynyl)phenyl]-1,6-dimethyl-6-(1H-pyrazol-4-yl)hexahydropyrimidine-2,4-dione (6S)-3-[2,6-Difluoro-4-(2-phenylethynyl)phenyl]-6-ethyl-1-methyl-6-(1-methylpyrazol-4-yl)hexahydropyrimidine-2,4-dione (6S)-3-[2,6-Difluoro-4-(2-phenylethynyl)phenyl]-6-(1-isopropylpyrazol-4-yl)-1,6-dimethyl-hexahydropyrimidine-2,4-dione (6S)-3-[2,6-Difluoro-4-(2-phenylethynyl)phenyl]-6-[1-(2-methoxyethyl)pyrazol-4-yl]-1,6-dimethyl-hexahydropyrimidine-2,4-dione (6S)-3-[2,6-Difluoro-4-(2-phenylethynyl)phenyl]-6-[1-(3-methoxypropyl)pyrazol-4-yl]-1,6-dimethyl-hexahydropyrimidine-2,4-dione (6S)-3-[2,6-Difluoro-4-(2-phenylethynyl)phenyl]-6-[1-(3-hydroxypropyl)pyrazol-4-yl]-1,6-dimethyl-hexahydropyrimidine-2,4-dione (6S)-3-[2,6-Difluoro-4-(2-phenylethynyl)phenyl]-6-[1-(2-hydroxyethyl)pyrazol-4-yl]-1,6-dimethyl-hexahydropyrimidine-2,4-dione (6S)-3-[2,6-Difluoro-4-(2-phenylethynyl)phenyl]-1,6-dimethyl-6-(1-methylpyrazol-3-yl)hexahydropyrimidine-2,4-dione (6S)-3-[2,6-Difluoro-4-(2-phenylethynyl)phenyl]-6-ethyl-1-methyl-6-(1-methylpyrazol-3-yl)hexahydropyrimidine-2,4-dione (6S)-3-[2,6-Difluoro-4-(2-phenylethynyl)phenyl]-6-(1-ethylpyrazol-3-yl)-1,6-dimethyl-hexahydropyrimidine-2,4-dione (6S)-3-[2,6-Difluoro-4-(2-phenylethynyl)phenyl]-6-(1-isopropylpyrazol-3-yl)-1,6-dimethyl-hexahydropyrimidine-2,4-dione (6S)-3-[2,6-Difluoro-4-(2-phenylethynyl)phenyl]-6-[1-(2-methoxyethyl)pyrazol-3-yl]-1,6-dimethyl-hexahydropyrimidine-2,4-dione (6S)-3-[2,6-Difluoro-4-(2-phenylethynyl)phenyl]-6-[1-(3-methoxypropyl)pyrazol-3-yl]-1,6-dimethyl-hexahydropyrimidine-2,4-dione (6S)-3-[2,6-Difluoro-4-(2-phenylethynyl)phenyl]-1,6-dimethyl-6-(1H-triazol-5-yl)hexahydropyrimidine-2,4-dione (6S)-3-[2,6-Difluoro-4-(2-phenylethynyl)phenyl]-1,6-dimethyl-6-(2-methyltriazol-4-yl)hexahydropyrimidine-2,4-dione (6S)-3-[2,6-Difluoro-4-(2-phenylethynyl)phenyl]-1,6-dimethyl-6-(1-methyltriazol-4-yl)hexahydropyrimidine-2,4-dione (6S)-3-[2,6-Difluoro-4-(2-phenylethynyl)phenyl]-1,6-dimethyl-6-oxazol-5-yl-hexahydropyrimidine-2,4-dione (6S)-3-[2,6-Difluoro-4-(2-phenylethynyl)phenyl]-6-isothiazol-3-yl-1,6-dimethyl-hexahydropyrimidine-2,4-dione (6S)-3-[2,6-Difluoro-4-(2-phenylethynyl)phenyl]-1,6-dimethyl-6-(2-methylthiazol-5-yl)hexahydropyrimidine-2,4-dione (6S)-3-[2,6-Difluoro-4-(2-phenylethynyl)phenyl]-6-isoxazol-3-yl-1,6-dimethyl-hexahydropyrimidine-2,4-dione (6S)-3-[2,6-Difluoro-4-(2-phenylethynyl)phenyl]-6-isoxazol-5-yl-1,6-dimethyl-hexahydropyrimidine-2,4-dione (6S)-3-[2,6-Difluoro-4-(2-phenylethynyl)phenyl]-1,6-dimethyl-6-thiazol-5-yl-hexahydropyrimidine-2,4-dione of (6S)-3-[2,6-Difluoro-4-(2-phenylethynyl)phenyl]-6-isothiazol-5-yl-1,6-dimethyl-hexahydropyrimidine-2,4-dione (6S)-3-[2,6-Difluoro-4-(2-phenylethynyl)phenyl]-6-ethyl-1-methyl-6-(1H-pyrazol-4-yl)hexahydropyrimidine-2,4-dione (S)-3-(2,6-Difluoro-4-(phenylethynyl)phenyl)-6-(1-(2-hydroxyethyl)-1H-pyrazol-3-yl)-1,6-dimethyldihydropyrimidine-2,4(1H,3H)-dione (6S)-6-(1-Cyclopropylpyrazol-4-yl)-3-[2,6-difluoro-4-(2-phenylethynyl)phenyl]-1,6-dimethyl-hexahydropyrimidine-2,4-dione (6S)-3-[2,6-Difluoro-4-(2-phenylethynyl)phenyl]-6-[1-(2-hydroxy-2-methyl-propyl)pyrazol-4-yl]-1,6-dimethyl-hexahydropyrimidine-2,4-dione (6S)-3-[2,6-Difluoro-4-(2-phenylethynyl)phenyl]-1,6-dimethyl-6-[1-(oxetan-3-ylmethyl)pyrazol-4-yl]hexahydropyrimidine-2,4-dione (6S)-3-[2,6-Difluoro-4-(2-phenylethynyl)phenyl]-1,6-dimethyl-6-[1-[(3RS)-tetrahydrofuran-3-yl]pyrazol-4-yl]hexahydropyrimidine-2,4-dione (6S)-3-[2,6-Difluoro-4-(2-phenylethynyl)phenyl]-6-[1-(2-hydroxy-2-methyl-propyl)pyrazol-3-yl]-1,6-dimethyl-hexahydropyrimidine-2,4-dione or (6S)-3-[2,6-Difluoro-4-(2-phenylethynyl)phenyl]-1,6-dimethyl-6-[1-[(3RS)-tetrahydrofuran-3-yl]pyrazol-3-yl]hexahydropyrimidine-2,4-dione.

One further object of the present invention are compounds of formula IB

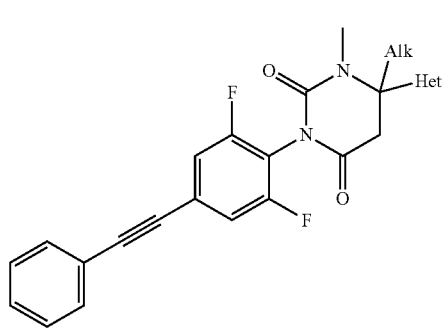

wherein

Het is a bicyclic heteroaromatic ring, containing two or three N-heteroatoms selected from the groups

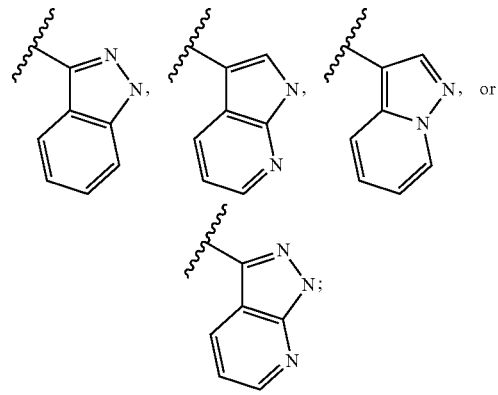

Alk is lower alkyl;
or a pharmaceutically acceptable salt or acid addition salt, a racemic mixture, or its corresponding enantiomer and/or optical isomer and/or stereoisomer thereof, for example the following compounds (6S)-3-[2,6-Difluoro-4-(2-phenylethynyl)phenyl]-1,6-dimethyl-6-(1-methylindazol-3-yl)hexahydropyrimidine-2,4-dione (6S)-3-[2,6-Difluoro-4-(2-phenylethynyl)phenyl]-1,6-dimethyl-6-(1-methylpyrrolo[2,3-b]pyridin-3-yl)hexahydropyrimidine-2,4-dione (6S)-3-[2,6-Difluoro-4-(2-phenylethynyl)phenyl]-1,6-dimethyl-6-pyrazolo[1,5-a]pyridin-3-yl-hexahydropyrimidine-2,4-dione or (6S)-3-[2,6-Difluoro-4-(2-phenylethynyl)phenyl]-1,6-dimethyl-6-(1-methylpyrazolo[3,4-b]pyridin-3-yl)hexahydropyrimidine-2,4-dione.

One further object of the present invention are compounds of formula IC

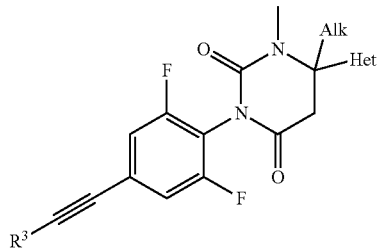

wherein $R^3$ is phenyl, pyridinyl or isothiazolyl, wherein the N atom in the pyridinyl group may be in different positions, and wherein phenyl is substituted by one or two halogen atoms;

Het is a 5-membered heteroaryl group, containing two or three heteroatoms, selected from N, O or S, optionally substituted by lower alkyl, cycloalkyl, lower alkoxyalkyl; heterocycloalkyl, wherein the hetero-atom is O, or lower alkyl substituted by hydroxy, Alk is lower alkyl;
or a pharmaceutically acceptable salt or acid addition salt, a racemic mixture, or its corresponding enantiomer and/or optical isomer and/or stereoisomer thereof, for example the following compounds (6S)-3-[2,6-Difluoro-4-[2-(3-pyridyl)ethynyl]phenyl]-1,6-dimethyl-6-(1-methylpyrazol-4-yl)hexahydropyrimidine-2,4-dione (6S)-3-[2,6-Difluoro-4-(2-isothiazol-4-ylethynyl)phenyl]-1,6-dimethyl-6-(1-methylpyrazol-4-yl)hexahydropyrimidine-2,4-dione (6S)-3-[2,6-Difluoro-4-[2-(3-pyridyl)ethynyl]phenyl]-1,6-dimethyl-6-(1H-pyrazol-4-yl)hexahydropyrimidine-2,4-dione (6S)-3-[2,6-Difluoro-4-[2-(3-fluorophenyl)ethynyl]phenyl]-1,6-dimethyl-6-(1-methylpyrazol-4-yl)hexahydropyrimidine-2,4-dione (6S)-3-[4-[2-(2,5-Difluorophenyl)ethynyl]-2,6-difluorophenyl]-1,6-dimethyl-6-(1-methylpyrazol-4-yl)hexahydropyrimidine-2,4-dione (6S)-3-[2,6-Difluoro-4-[2-(4-fluorophenyl)ethynyl]phenyl]-1,6-dimethyl-6-(1-methylpyrazol-4-yl)hexahydropyrimidine-2,4-dione (6S)-3-[2,6-Difluoro-4-[2-(2-fluorophenyl)ethynyl]phenyl]-1,6-dimethyl-6-(1-methylpyrazol-4-yl)hexahydropyrimidine-2,4-dione
(6S)-3-[2,6-Difluoro-4-[2-(3-pyridyl)ethynyl]phenyl]-6-ethyl-1-methyl-6-(1H-pyrazol-4-yl)hexahydropyrimidine-2,4-dione
(6S)-3-[2,6-Difluoro-4-[2-(2-fluorophenyl)ethynyl]phenyl]-1,6-dimethyl-6-(1H-pyrazol-4-yl)hexahydropyrimidine-2,4-dione
(6S)-3-[2,6-Difluoro-4-[2-(4-fluorophenyl)ethynyl]phenyl]-1,6-dimethyl-6-(1H-pyrazol-4-yl)hexahydropyrimidine-2,4-dione
(6S)-3-[4-[2-(2,3-Difluorophenyl)ethynyl]-2,6-difluorophenyl]-1,6-dimethyl-6-(1H-pyrazol-4-yl)hexahydropyrimidine-2,4-dione
(6S)-3-[4-[2-(2,4-Difluorophenyl)ethynyl]-2,6-difluorophenyl]-1,6-dimethyl-6-(1H-pyrazol-4-yl)hexahydropyrimidine-2,4-dione
(6S)-3-[4-[2-(2,3-Difluorophenyl)ethynyl]-2,6-difluorophenyl]-1,6-dimethyl-6-(1-methylpyrazol-4-yl)hexahydropyrimidine-2,4-dione
(6S)-3-[4-[2-(2,4-Difluorophenyl)ethynyl]-2,6-difluorophenyl]-1,6-dimethyl-6-(1-methylpyrazol-4-yl)hexahydropyrimidine-2,4-dione or
(6S)-3-[2,6-Difluoro-4-[2-(3-fluorophenyl)ethynyl]phenyl]-1,6-dimethyl-6-(1H-pyrazol-4-yl)hexahydropyrimidine-2,4-dione.

One further object of the present invention are compounds of formula

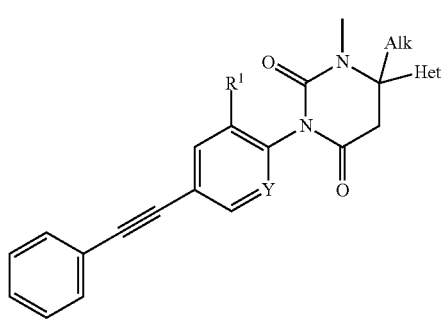

ID wherein
Y is C—$R^{1'}$;
$R^{1'}$ is hydrogen or Cl;
$R^1$ is F or Cl;
$R^3$ is phenyl, pyridinyl or isothiazolyl, wherein the N atom in the pyridinyl group may be in different positions, optionally substituted by one or two halogen atoms;
Alk is lower alkyl;
or a pharmaceutically acceptable salt or acid addition salt, a racemic mixture, or its corresponding enantiomer and/or optical isomer and/or stereoisomer thereof, for example the following compounds:
(6S)-3-[2-Chloro-4-(2-phenylethynyl)phenyl]-1,6-dimethyl-6-(1-methylpyrazol-4-yl)hexahydropyrimidine-2,4-dione or
(6S)-3-[2-Chloro-6-fluoro-4-(2-phenylethynyl)phenyl]-1,6-dimethyl-6-(1-methylpyrazol-4-yl)hexahydropyrimidine-2,4-dione.

The preparation of compounds of formula I of the present invention may be carried out in sequential or convergent synthetic routes. Syntheses of the compounds of the invention are shown in the following schemes 1 to 3. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises
a) alkylating a compound of formula

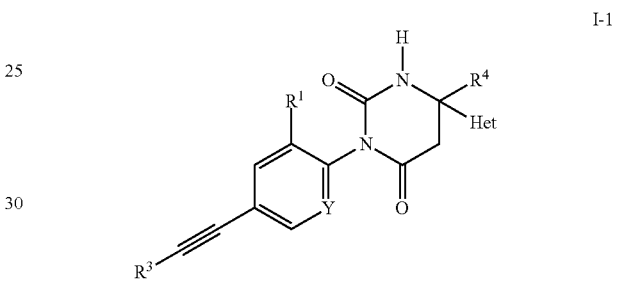

I-1 with $R^2$—I in the presence of NaH or $Cs_2CO_3$ in DMF to a compound of formula

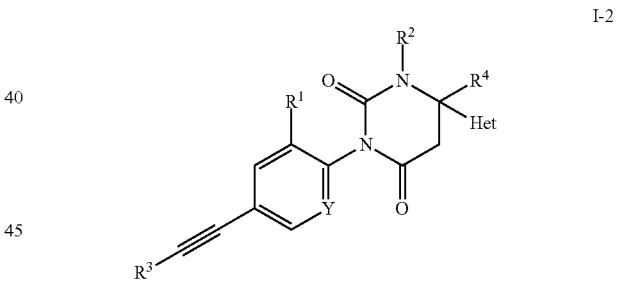

I-2 wherein $R^2$ is lower alkyl and the remaining substituents are described above, or if desired, converting the compounds obtained into pharmaceutically acceptable acid addition salts.

b) reacting a compound of formula 5

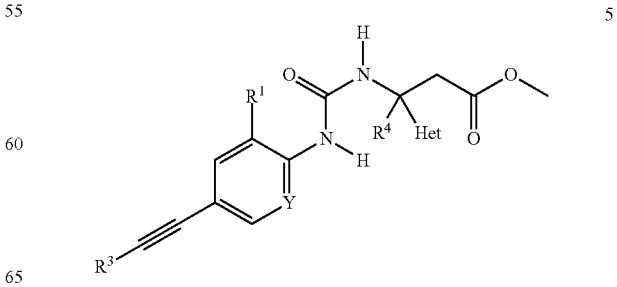

5 with NaH in THF or DMF to a compound of formula I-1

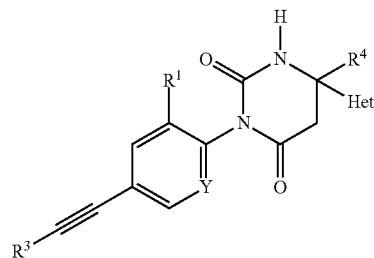
I-1 wherein the substituents are described above, or
if desired, converting the compounds obtained into pharmaceutically acceptable acid addition salts.

c) reacting a compound of formula 9

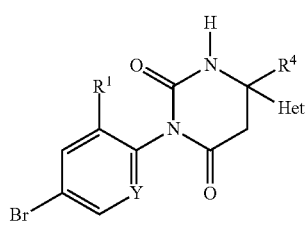
9 with a compound of formula

2 in the presence of Bis-(tpp)-Pd(II)Cl$_2$, Et3N, TPP, CUI in DMF or THF to a compound of formula

I-1 wherein the substituents are described above, or
if desired, converting the compounds obtained into pharmaceutically acceptable acid addition salts.

The preparation of compounds of formula I is further described in more detail in schemes 1 to 3 and in examples 1-64.

Scheme 1

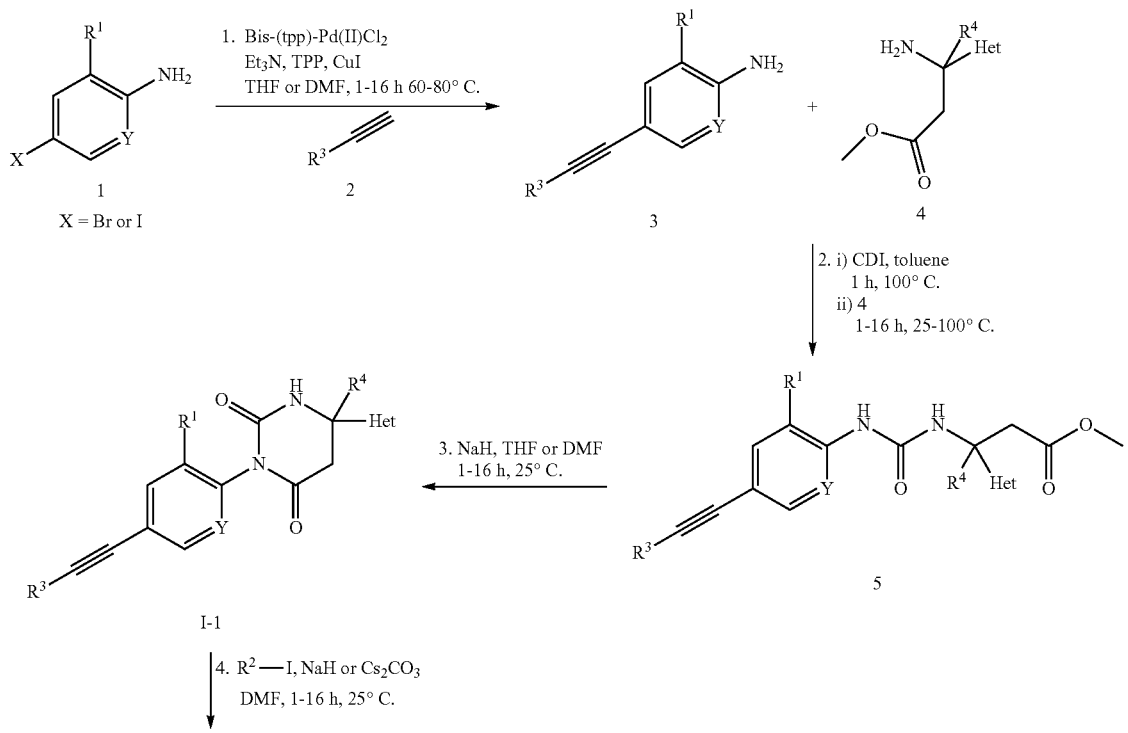

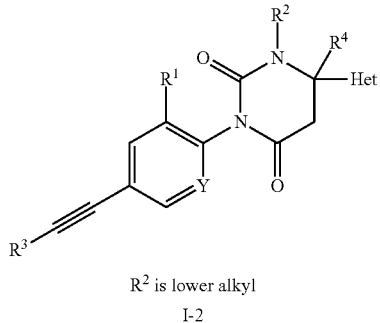

R² is lower alkyl

I-2

An ethynyl-phenyl, ethynyl-pyridyl or ethynyl-isothiazolyl substituted pyrimidine-2,4-dione compound of general formula I can be obtained for example by Sonogashira coupling of an appropriately substituted aniline or aminopyridine 1 with an appropriately substituted arylacetylene 2 to yield the desired ethynyl compounds of formula 3. Reacting ethynyl compounds of formula 3 with an appropriately substituted aminoester of formula 4 with phosgene or a phosgene equivalent such as triphosgene or carbonyldiimidazole (CDI) in presence or absence of a base such as triethylamine in a solvent such as DMF, toluene or dioxane forms the desired urea analogues of formula 5. Ring closure of 5 with a strong base such as NaH or KOtBu in a solvent like THF or DMF forms the desired pyrimidine-2,4-dione compounds of formula I-1. Introduction of the R² substituent (R²=lower alkyl) via alkylation forms the desired ethynyl-phenyl, ethynyl-pyridyl or ethynyl-isothiazolyl substituted pyrimidine-2,4-dione compound of general formula I-2 (scheme 1).

Generally speaking, the sequence of steps used to synthesize the compounds of formula I can also be modified in certain cases.

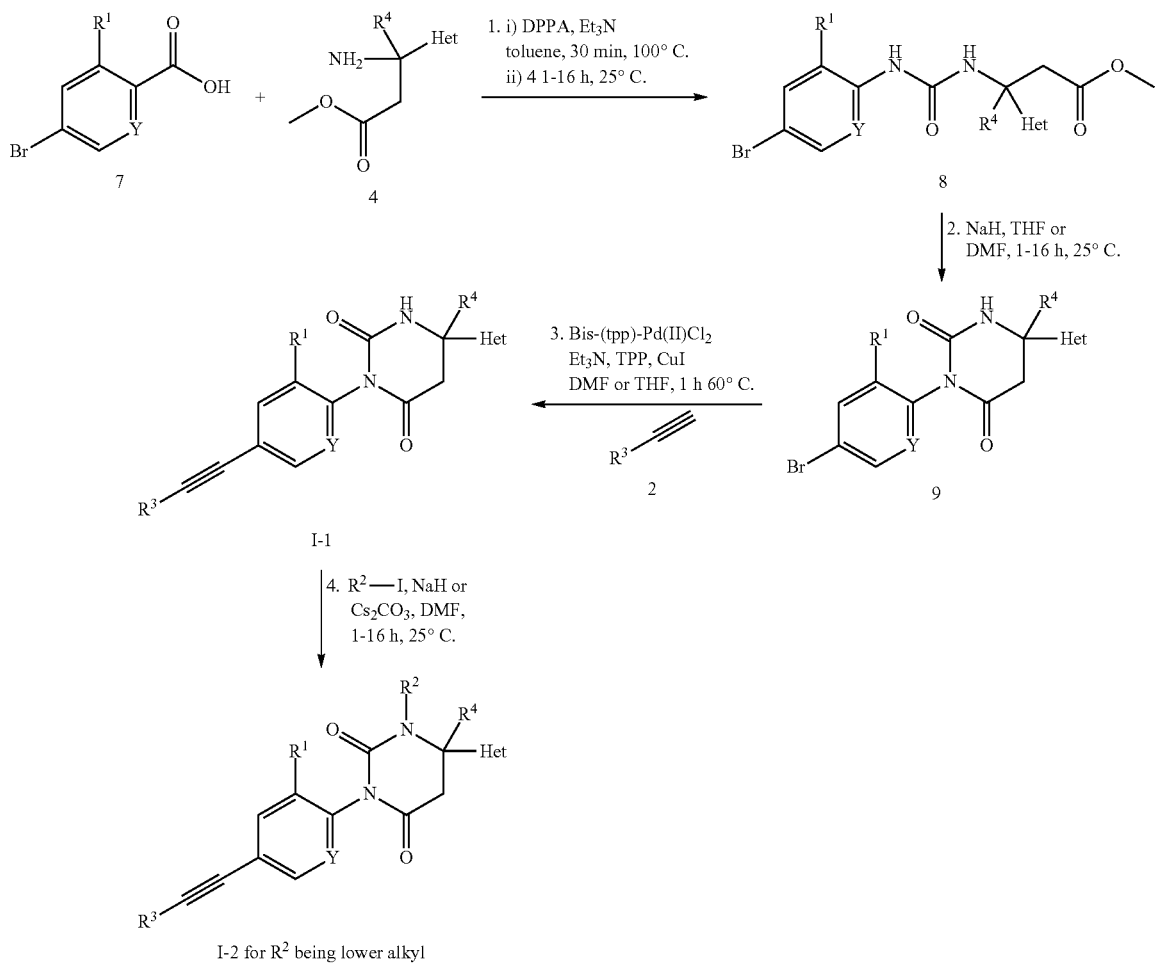

An ethynyl-phenyl, ethynyl-pyridyl or ethynyl-isothiazolyl substituted pyrimidine-2,4-dione compound of general formula I can also be obtained for example by reacting an appropriately substituted acid 7 with DPPA to form the corresponding isocyanate which is then reacted with an appropriately substituted aminoester of formula 4 in presence of a base such as triethylamine in a solvent such as toluene to yield the desired urea analogue of formula 8. Ring closure of 8 with a strong base such as NaH or KOtBu in a solvent like THF or DMF forms the desired pyrimidine-2,4-dione compounds of formula 9. Sonogashira coupling of compounds 9 with an appropriately substituted arylacetylene 2 yields the desired ethynyl compounds of formula I-1. Introduction of the $R^2$ substituent ($R^2$=lower alkyl) via alkylation forms the desired ethynyl-phenyl, ethynyl-pyridyl or ethynyl-isothiazolyl substituted pyrimidine-2,4-dione compound of general formula I-2 (scheme 2).

Generally speaking, the sequence of steps used to synthesize the compounds of formula I can also be modified in certain cases.

An ethynyl-phenyl, ethynyl-pyridyl or ethynyl-isothiazolyl substituted pyrimidine-2,4-dione compound of general formula I can be obtained for example by Sonogashira coupling of an appropriately substituted aniline or aminopyridine 1 with an appropriately substituted arylacetylene 2 to yield the desired ethynyl compounds of formula 3. Reacting ethynyl compounds of formula 3 with phenyl chloroformate 10 forms the reactive phenylcarbamate 11. Reacting the intermediate 11 with an appropriately substituted aminoester of formula 4 with a base such as potassium carbonate in a solvent such as THF or DMF forms the desired urea analogues of formula 5. Ring closure of 5 with a strong base such as NaH or KOtBu in a solvent like THF or DMF forms the desired pyrimidine-2,4-dione compounds of formula I-1. Introduction of the $R^2$ substituent ($R^2$=lower alkyl) via alkylation forms the desired ethynyl-phenyl, ethynyl-pyridyl or ethynyl-isothiazolyl substituted pyrimidine-2,4-dione compound of general formula I-2 (scheme 1).

Generally speaking, the sequence of steps used to synthesize the compounds of formula I can also be modified in certain cases.

Scheme 3

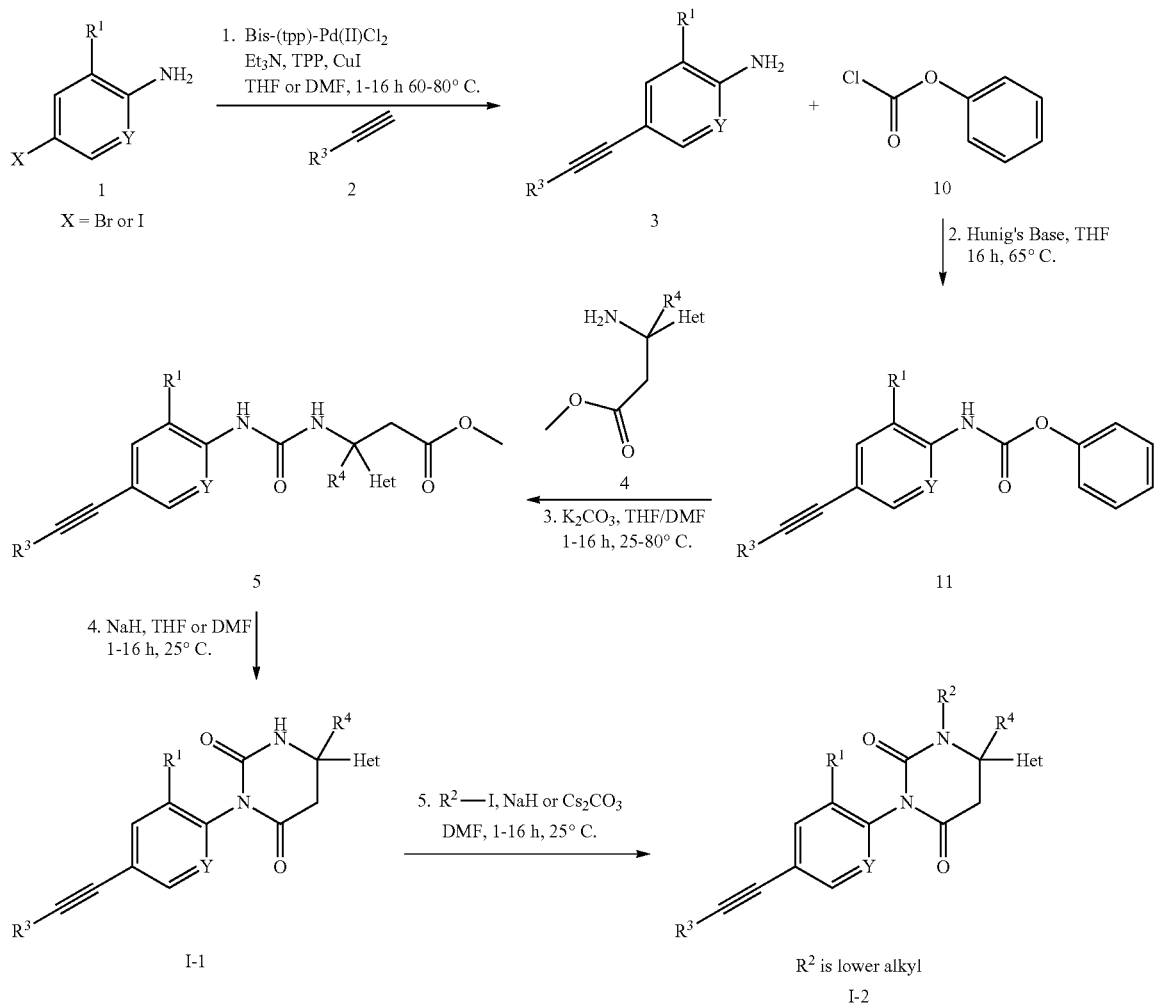

Biological Assay and Data

Determination of $EC_{50}$ Values Using a Ca2+ Mobilization In Vitro Assay on Recombinant Human mGlu4 Expressed in HEK293 Cells:

A monoclonal HEK-293 cell line stably transfected with a cDNA encoding for the human mGlu4 receptor was generated; for the work with mGlu4 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist (2S)-2-amino-4-phosphonobutanoic acid (L-AP4) was added to the cells at a concentration corresponding to $EC_{20}$ with on-line recording of fluorescence; in order to account for day-to-day variations in the responsiveness of cells, the $EC_{20}$ of L-AP4 was determined immediately ahead of each experiment by recording of a full dose-response curve of L-AP4.

Responses were measured as peak increase in fluorescence minus basal (i.e. fluorescence without addition of L-AP4), normalized to the maximal stimulatory effect obtained with saturating concentrations of L-AP4. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (drug concentration at which 50% of the maximal receptor activation was achieved), the Hill coefficient as well as the maximal response in % of the maximal stimulatory effect obtained with saturating concentrations of L-AP4 were calculated (see FIG. 1).

Positive signals obtained during the pre-incubation with the PAM test compounds (i.e. before application of an $EC_{20}$ concentration of L-AP4) were indicative of an agonistic activity, the absence of such signals were demonstrating the lack of agonistic activities. A depression of the signal observed after addition of the $EC_{20}$ concentration of L-AP4 was indicative of an inhibitory activity of the test compound.

List of Examples and Data:

| | Structure | Name | $EC_{50}$ (nM) mGlu4 PAM | Eff. (%) |
|---|---|---|---|---|
| 1 | 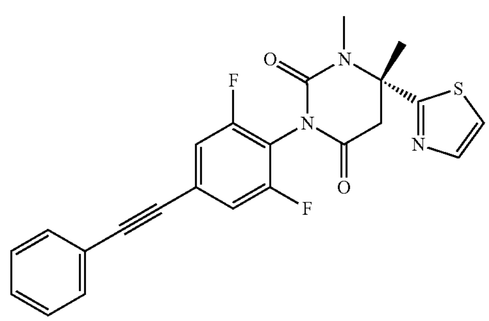 | (6S)-3-[2,6-Difluoro-4-(2-phenylethynyl)phenyl]-1,6-dimethyl-6-thiazol-2-yl-hexahydropyrimidine-2,4-dione | 113 | 119 |
| 2 | 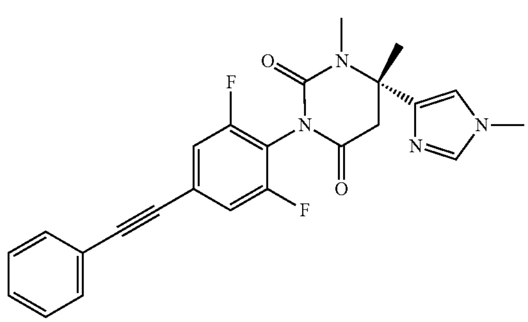 [SMILES: CN1C(=O)N(c2c(F)cc(C#Cc3ccccc3)cc2F)C(=O)C[C@@]1(C)c1cn(C)cn1] | (6S)-3-[2,6-Difluoro-4-(2-phenylethynyl)phenyl]-1,6-dimethyl-6-(1-methylimidazol-4-yl)hexahydropyrimidine-2,4-dione | 121 | 109 |

-continued

| | Structure | Name | EC$_{50}$ (nM) mGlu4 PAM | Eff. (%) |
|---|---|---|---|---|
| 3 | 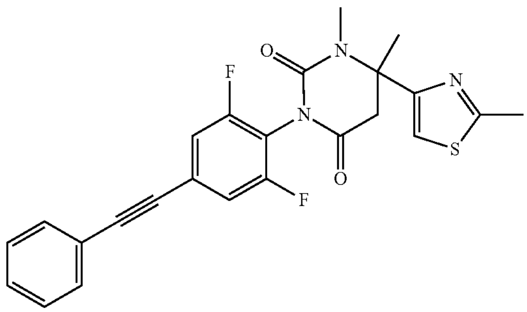 [SMILES: Cc1nc(C2(C)CC(=O)N(c3c(F)cc(C#Cc4ccccc4)cc3F)C(=O)N2C)cs1] | (6RS)-3-[2,6-Difluoro-4-(2-phenylethynyl)phenyl]-1,6-dimethyl-6-(2-methylthiazol-4-yl)hexahydropyrimidine-2,4-dione | 94 | 138 |
| 4 | 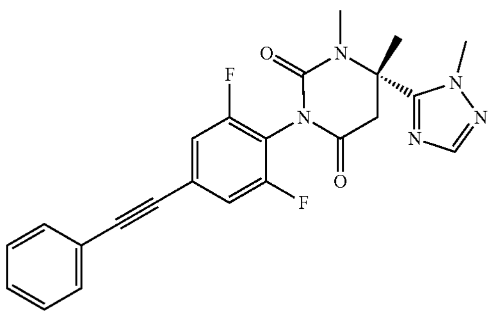 [SMILES: CN1C(=O)N(c2c(F)cc(C#Cc3ccccc3)cc2F)C(=O)C[C@@]1(C)c1ncnn1C] | (6S)-3-[2,6-Difluoro-4-(2-phenylethynyl)phenyl]-1,6-dimethyl-6-(2-methyl-1,2,4-triazol-3-yl)hexahydropyrimidine-2,4-dione | 136 | 95 |
| 5 | 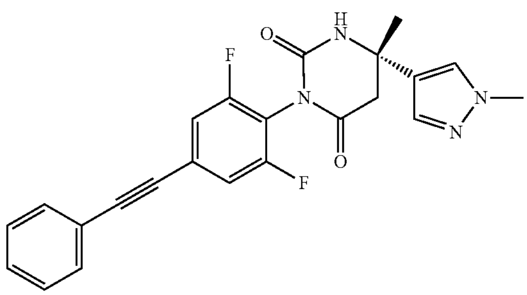 [SMILES: Cn1cc([C@]2(C)CC(=O)N(c3c(F)cc(C#Cc4ccccc4)cc3F)C(=O)N2)cn1] | (6S)-3-[2,6-Difluoro-4-(2-phenylethynyl)phenyl]-6-methyl-6-(1-methylpyrazol-4-yl)hexahydropyrimidine-2,4-dione | 110 | 103 |
| 6 | 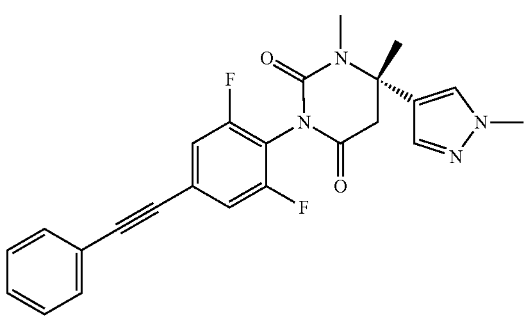 | (6S)-3-[2,6-Difluoro-4-(2-phenylethynyl)phenyl]-1,6-dimethyl-6-(1-methylpyrazol-4-yl)hexahydropyrimidine-2,4-dione | 36 | 98 |
| 7 | 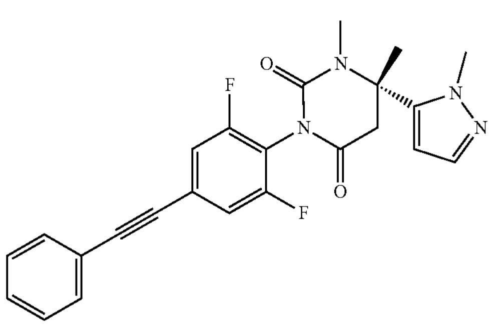 [SMILES: CN1C(=O)N(c2c(F)cc(C#Cc3ccccc3)cc2F)C(=O)C[C@@]1(C)c1ccnn1C] | (6S)-3-[2,6-Difluoro-4-(2-phenylethynyl)phenyl]-1,6-dimethyl-6-(2-methylpyrazol-3-yl)hexahydropyrimidine-2,4-dione | 147 | 100 |

-continued

| | Structure | Name | EC$_{50}$ (nM) mGlu4 PAM | Eff. (%) |
|---|---|---|---|---|
| 8 | 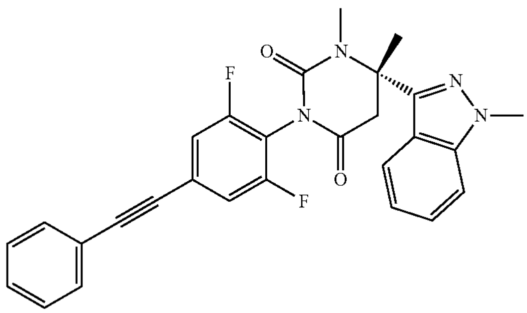 [SMILES: CN1C(=O)N(c2c(F)cc(C#Cc3ccccc3)cc2F)C(=O)C[C@@]1(C)c1nn(C)c2ccccc12] | (6S)-3-[2,6-Difluoro-4-(2-phenylethynyl)phenyl]-1,6-dimethyl-6-(1-methylindazol-3-yl)hexahydropyrimidine-2,4-dione | 157 | 99 |
| 9 | 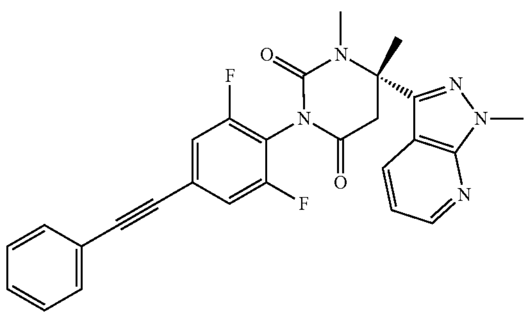 [SMILES: CN1C(=O)N(c2c(F)cc(C#Cc3ccccc3)cc2F)C(=O)C[C@@]1(C)c1nn(C)c2ncccc12] | (6S)-3-[2,6-Difluoro-4-(2-phenylethynyl)phenyl]-1,6-dimethyl-6-(1-methylpyrrolo[2,3-b]pyridin-3-yl)hexahydropyrimidine-2,4-dione | 81 | 155 |
| 10 | 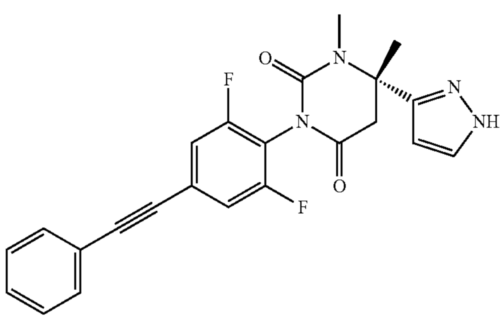 [SMILES: CN1C(=O)N(c2c(F)cc(C#Cc3ccccc3)cc2F)C(=O)C[C@@]1(C)c1cc[nH]n1] | (6S)-3-[2,6-Difluoro-4-(2-phenylethynyl)phenyl]-1,6-dimethyl-6-(1H-pyrazol-3-yl)hexahydropyrimidine-2,4-dione | 84 | 134 |
| 11 | 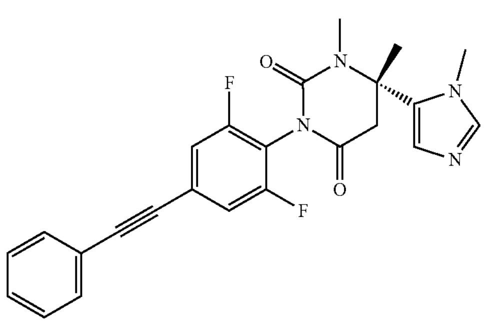 [SMILES: CN1C(=O)N(c2c(F)cc(C#Cc3ccccc3)cc2F)C(=O)C[C@@]1(C)c1cncn1C] | (6S)-3-[2,6-Difluoro-4-(2-phenylethynyl)phenyl]-1,6-dimethyl-6-(3-methylimidazol-4-yl)hexahydropyrimidine-2,4-dione | 59 | 91 |

-continued

| | Structure | Name | EC$_{50}$ (nM) mGlu4 PAM | Eff. (%) |
|---|---|---|---|---|
| 12 | 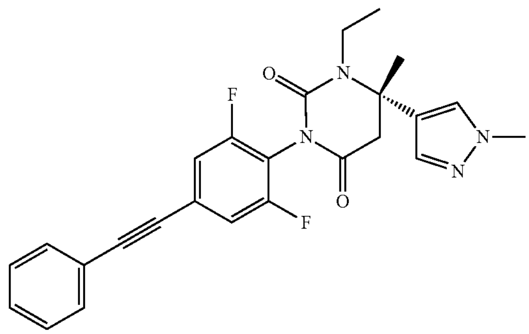 [SMILES: CCN1C(=O)N(c2c(F)cc(C#Cc3ccccc3)cc2F)C(=O)C[C@@]1(C)c1cnn(C)c1] | (6S)-3-[2,6-Difluoro-4-(2-phenylethynyl)phenyl]-1-ethyl-6-methyl-6-(1-methylpyrazol-4-yl)hexahydropyrimidine-2,4-dione | 67 | 95 |
| 13 | 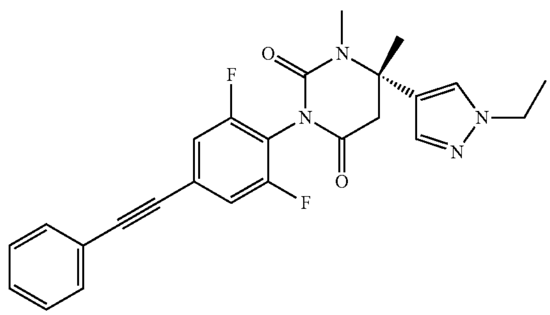 [SMILES: CCn1cc([C@]2(C)CC(=O)N(c3c(F)cc(C#Cc4ccccc4)cc3F)C(=O)N2C)cn1] | (6S)-3-[2,6-Difluoro-4-(2-phenylethynyl)phenyl]-6-(1-ethylpyrazol-4-yl)-1,6-dimethyl-hexahydropyrimidine-2,4-dione | 64 | 115 |
| 14 | 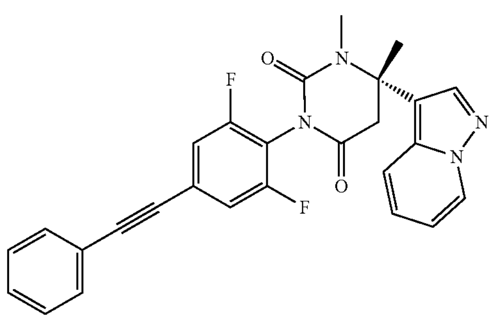 [SMILES: CN1C(=O)N(c2c(F)cc(C#Cc3ccccc3)cc2F)C(=O)C[C@@]1(C)c1cnn2ccccc12] | (6S)-3-[2,6-Difluoro-4-(2-phenylethynyl)phenyl]-1,6-dimethyl-6-pyrazolo[1,5-a]pyridin-3-yl-hexahydropyrimidine-2,4-dione | 93 | 137 |
| 15 | 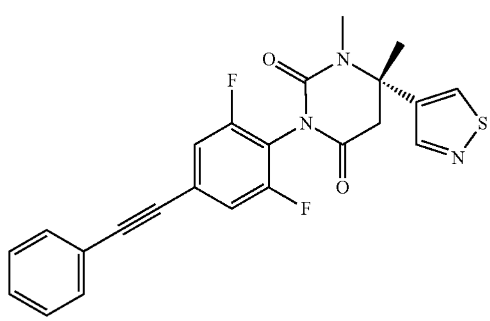 [SMILES: CN1C(=O)N(c2c(F)cc(C#Cc3ccccc3)cc2F)C(=O)C[C@@]1(C)c1cnsc1] | (6S)-3-[2,6-Difluoro-4-(2-phenylethynyl)phenyl]-6-isothiazol-4-yl-1,6-dimethyl-hexahydropyrimidine-2,4-dione | 38 | 167 |

-continued

| | Structure | Name | EC$_{50}$ (nM) mGlu4 PAM | Eff. (%) |
|---|---|---|---|---|
| 16 | 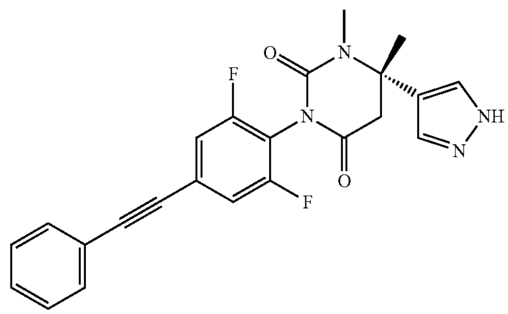 [SMILES: CN1C(=O)N(c2c(F)cc(C#Cc3ccccc3)cc2F)C(=O)C[C@@]1(C)c1cn[nH]c1] | (6S)-3-[2,6-Difluoro-4-(2-phenylethynyl)phenyl]-1,6-dimethyl-6-(1H-pyrazol-4-yl)hexahydropyrimidine-2,4-dione | 36 | 131 |
| 17 | 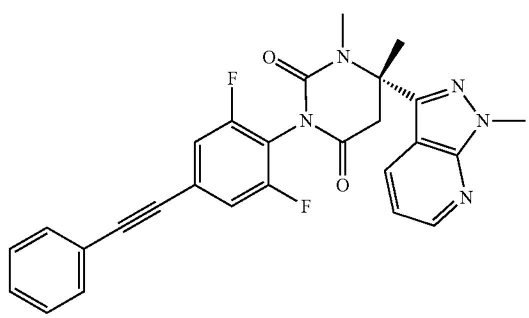 [SMILES: CN1C(=O)N(c2c(F)cc(C#Cc3ccccc3)cc2F)C(=O)C[C@@]1(C)c1nn(C)c2ncccc12] | (6S)-3-[2,6-Difluoro-4-(2-phenylethynyl)phenyl]-1,6-dimethyl-6-(1-methylpyrazolo[3,4-b]pyridin-3-yl)hexahydropyrimidine-2,4-dione | 126 | 154 |
| 18 | 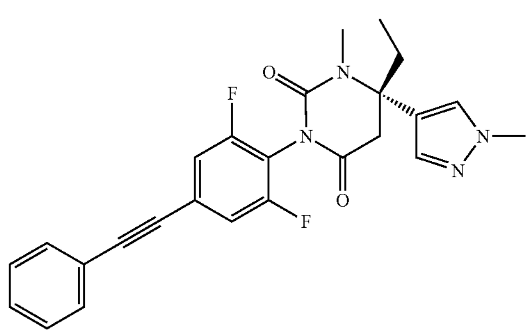 [SMILES: CC[C@@]1(c2cnn(C)c2)CC(=O)N(c2c(F)cc(C#Cc3ccccc3)cc2F)C(=O)N1C] | (6S)-3-[2,6-Difluoro-4-(2-phenylethynyl)phenyl]-6-ethyl-1-methyl-6-(1-methylpyrazol-4-yl)hexahydropyrimidine-2,4-dione | 47 | 135 |
| 19 | 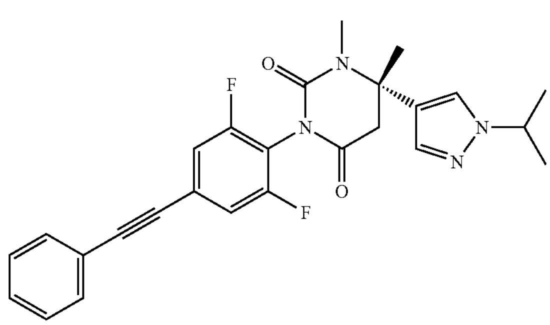 [SMILES: CC(C)n1cc([C@]2(C)CC(=O)N(c3c(F)cc(C#Cc4ccccc4)cc3F)C(=O)N2C)cn1] | (6S)-3-[2,6-Difluoro-4-(2-phenylethynyl)phenyl]-6-(1-isopropylpyrazol-4-yl)-1,6-dimethyl-hexahydropyrimidine-2,4-dione | 36 | 139 |

-continued

| | Structure | Name | EC$_{50}$ (nM) mGlu4 PAM | Eff. (%) |
|---|---|---|---|---|
| 20 | 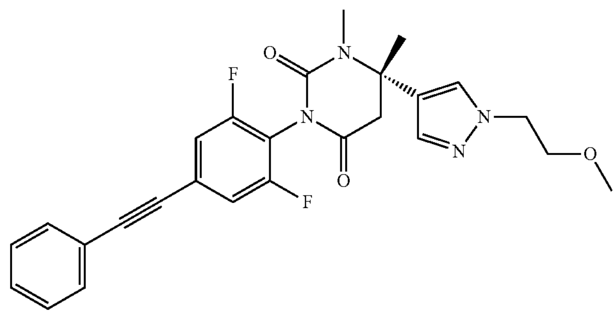 [SMILES: COCCn1cc([C@]2(C)CC(=O)N(c3c(F)cc(C#Cc4ccccc4)cc3F)C(=O)N2C)cn1] | (6S)-3-[2,6-Difluoro-4-(2-phenylethynyl)phenyl]-6-[1-(2-methoxyethyl)pyrazol-4-yl]-1,6-dimethyl-hexahydropyrimidine-2,4-dione | 54 | 137 |
| 21 | 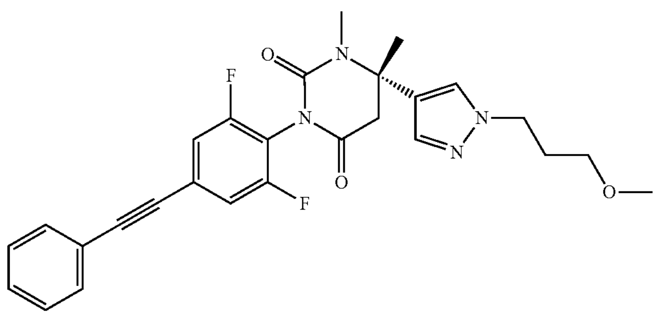 [SMILES: COCCCn1cc([C@]2(C)CC(=O)N(c3c(F)cc(C#Cc4ccccc4)cc3F)C(=O)N2C)cn1] | (6S)-3-[2,6-Difluoro-4-(2-phenylethynyl)phenyl]-6-[1-(3-methoxypropyl)pyrazol-4-yl]-1,6-dimethyl-hexahydropyrimidine-2,4-dione | 70 | 136 |
| 22 | 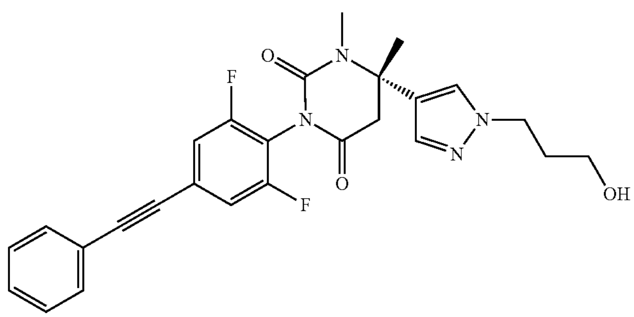 [SMILES: CN1C(=O)N(c2c(F)cc(C#Cc3ccccc3)cc2F)C(=O)C[C@@]1(C)c1cnn(CCCO)c1] | (6S)-3-[2,6-Difluoro-4-(2-phenylethynyl)phenyl]-6-[1-(3-hydroxypropyl)pyrazol-4-yl]-1,6-dimethyl-hexahydropyrimidine-2,4-dione | 56 | 143 |
| 23 | 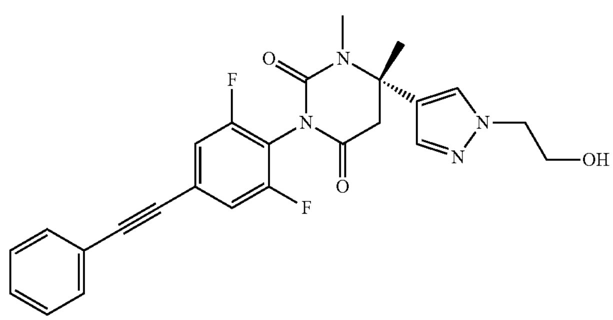 [SMILES: CN1C(=O)N(c2c(F)cc(C#Cc3ccccc3)cc2F)C(=O)C[C@@]1(C)c1cnn(CCO)c1] | (6S)-3-[2,6-Difluoro-4-(2-phenylethynyl)phenyl]-6-[1-(2-hydroxyethyl)pyrazol-4-yl]-1,6-dimethyl-hexahydropyrimidine-2,4-dione | 108 | 147 |
| 24 | 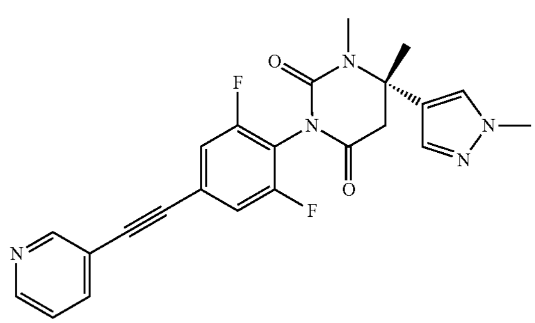 [SMILES: CN1C(=O)N(c2c(F)cc(C#Cc3cccnc3)cc2F)C(=O)C[C@@]1(C)c1cnn(C)c1] | (6S)-3-[2,6-Difluoro-4-[2-(3-pyridyl)ethynyl]phenyl]-1,6-dimethyl-6-(1-methylpyrazol-4-yl)hexahydropyrimidine-2,4-dione | 39 | 141 |

|  | Structure | Name | EC₅₀ (nM) mGlu4 PAM | Eff. (%) |
|---|---|---|---|---|
| 25 | 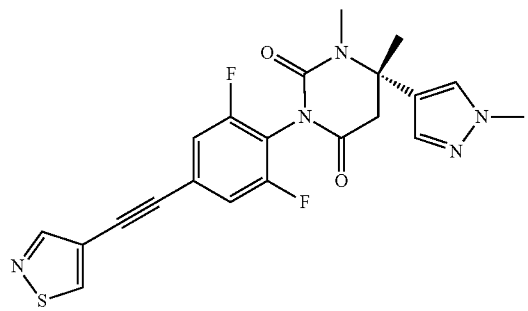 [SMILES: CN1C(=O)N(c2c(F)cc(C#Cc3cnsc3)cc2F)C(=O)C[C@@]1(C)c1cnn(C)c1] | (6S)-3-[2,6-Difluoro-4-(2-isothiazol-4-ylethynyl)phenyl]-1,6-dimethyl-6-(1-methylpyrazol-4-yl)hexahydropyrimidine-2,4-dione | 45 | 149 |
| 26 | 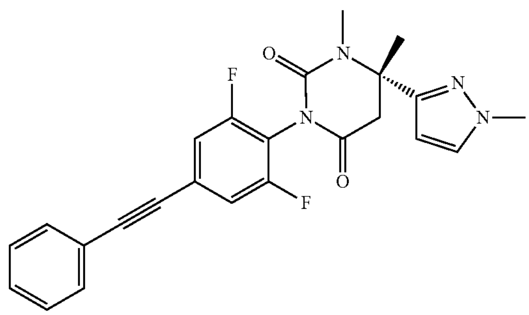 [SMILES: CN1C(=O)N(c2c(F)cc(C#Cc3ccccc3)cc2F)C(=O)C[C@@]1(C)c1ccn(C)n1] | (6S)-3-[2,6-Difluoro-4-(2-phenylethynyl)phenyl]-1,6-dimethyl-6-(1-methylpyrazol-3-yl)hexahydropyrimidine-2,4-dione | 69 | 146 |
| 27 | 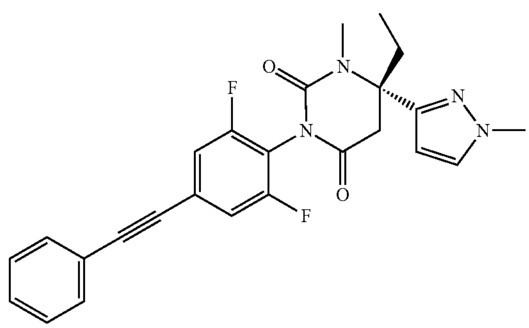 [SMILES: CC[C@@]1(c2ccn(C)n2)CC(=O)N(c2c(F)cc(C#Cc3ccccc3)cc2F)C(=O)N1C] | (6S)-3-[2,6-Difluoro-4-(2-phenylethynyl)phenyl]-6-ethyl-1-methyl-6-(1-methylpyrazol-3-yl)hexahydropyrimidine-2,4-dione | 83 | 143 |
| 28 | 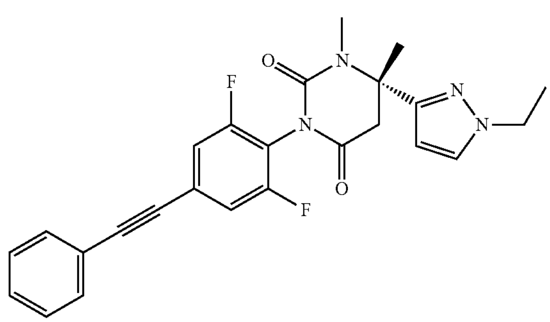 | (6S)-3-[2,6-Difluoro-4-(2-phenylethynyl)phenyl]-6-(1-ethylpyrazol-3-yl)-1,6-dimethyl-hexahydropyrimidine-2,4-dione | 96 | 139 |

-continued

| | Structure | Name | EC₅₀ (nM) mGlu4 PAM | Eff. (%) |
|---|---|---|---|---|
| 29 | 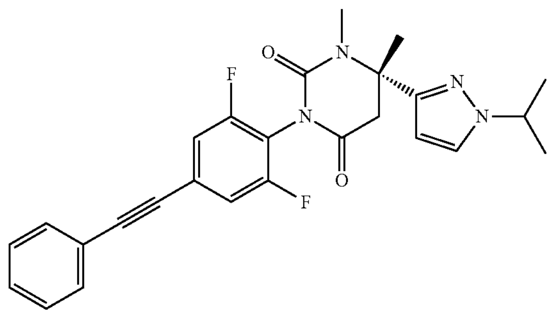 [SMILES: CC(C)n1ccc([C@]2(C)CC(=O)N(c3c(F)cc(C#Cc4ccccc4)cc3F)C(=O)N2C)n1] | (6S)-3-[2,6-Difluoro-4-(2-phenylethynyl)phenyl]-6-(1-isopropylpyrazol-3-yl)-1,6-dimethyl-hexahydropyrimidine-2,4-dione | 126 | 146 |
| 30 | 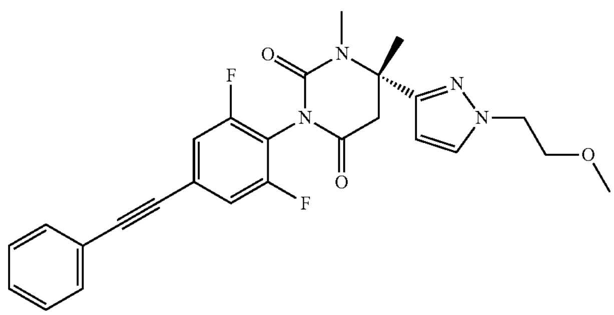 [SMILES: COCCn1ccc([C@]2(C)CC(=O)N(c3c(F)cc(C#Cc4ccccc4)cc3F)C(=O)N2C)n1] | (6S)-3-[2,6-Difluoro-4-(2-phenylethynyl)phenyl]-6-[1-(2-methoxyethyl)pyrazol-3-yl]-1,6-dimethyl-hexahydropyrimidine-2,4-dione | 59 | 143 |
| 31 | 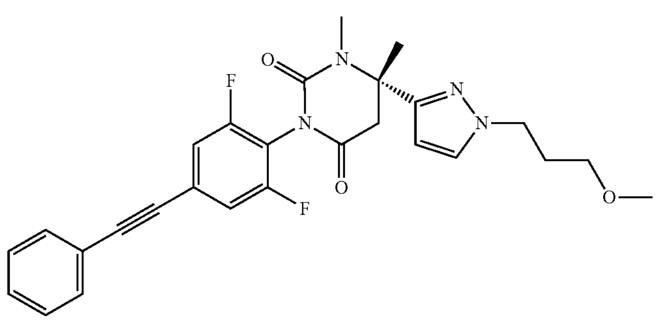 [SMILES: COCCCn1ccc([C@]2(C)CC(=O)N(c3c(F)cc(C#Cc4ccccc4)cc3F)C(=O)N2C)n1] | (6S)-3-[2,6-Difluoro-4-(2-phenylethynyl)phenyl]-6-[1-(3-methoxypropyl)pyrazol-3-yl]-1,6-dimethyl-hexahydropyrimidine-2,4-dione | 23 | 117 |
| 32 | 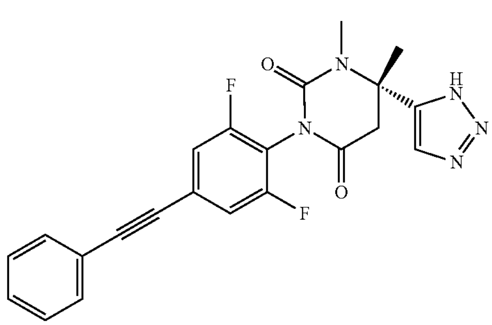 [SMILES: CN1C(=O)N(c2c(F)cc(C#Cc3ccccc3)cc2F)C(=O)C[C@@]1(C)c1cnn[nH]1] | (6S)-3-[2,6-Difluoro-4-(2-phenylethynyl)phenyl]-1,6-dimethyl-6-(1H-triazol-5-yl)hexahydropyrimidine-2,4-dione | 20 | 114 |

-continued

| | Structure | Name | EC$_{50}$ (nM) mGlu4 PAM | Eff. (%) |
|---|---|---|---|---|
| 33 | 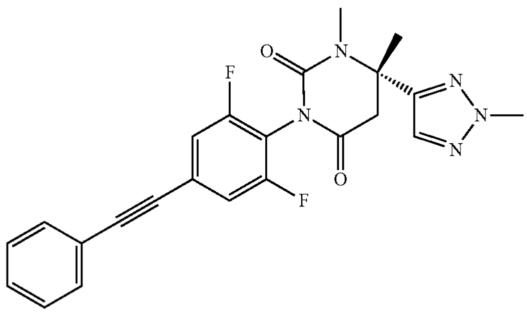 [SMILES: CN1C(=O)N(c2c(F)cc(C#Cc3ccccc3)cc2F)C(=O)C[C@@]1(C)c1cnn(C)n1] | (6S)-3-[2,6-Difluoro-4-(2-phenylethynyl)phenyl]-1,6-dimethyl-6-(2-methyltriazol-4-yl)hexahydropyrimidine-2,4-dione | 59 | 196 |
| 34 | 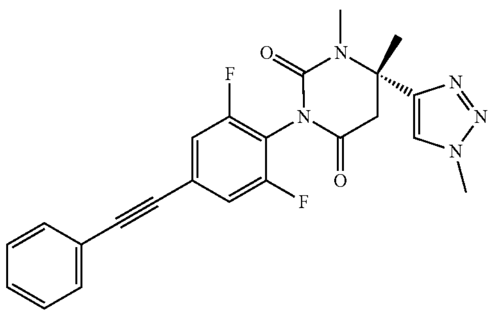 [SMILES: CN1C(=O)N(c2c(F)cc(C#Cc3ccccc3)cc2F)C(=O)C[C@@]1(C)c1cn(C)nn1] | (6S)-3-[2,6-Difluoro-4-(2-phenylethynyl)phenyl]-1,6-dimethyl-6-(1-methyltriazol-4-yl)hexahydropyrimidine-2,4-dione | 71 | 207 |
| 35 | 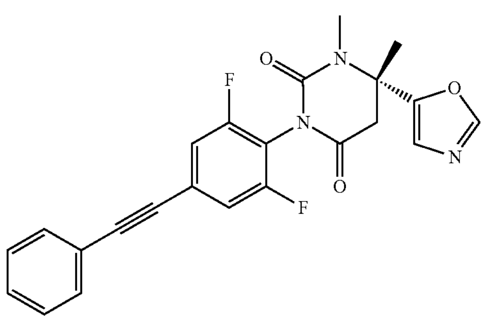 [SMILES: CN1C(=O)N(c2c(F)cc(C#Cc3ccccc3)cc2F)C(=O)C[C@@]1(C)c1cnco1] | (6S)-3-[2,6-Difluoro-4-(2-phenylethynyl)phenyl]-1,6-dimethyl-6-oxazol-5-yl-hexahydropyrimidine-2,4-dione | 90 | 195 |
| 36 | 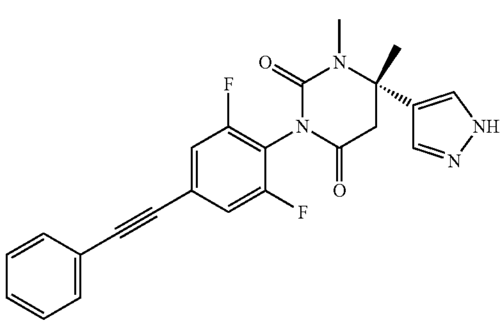 [SMILES: CN1C(=O)N(c2c(F)cc(C#Cc3ccccc3)cc2F)C(=O)C[C@@]1(C)c1cn[nH]c1] | (6S)-3-[2,6-Difluoro-4-[2-(3-pyridyl)ethynyl]phenyl]-1,6-dimethyl-6-(1H-pyrazol-4-yl)hexahydropyrimidine-2,4-dione | 41 | 164 |

-continued

| | Structure | Name | EC$_{50}$ (nM) mGlu4 PAM | Eff. (%) |
|---|---|---|---|---|
| 37 | 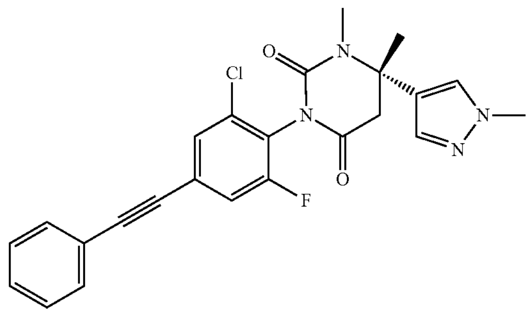 [SMILES: CN1C(=O)N(c2c(F)cc(C#Cc3ccccc3)cc2Cl)C(=O)C[C@@]1(C)c1cnn(C)c1] | (6S)-3-[2-Chloro-4-(2-phenylethynyl)phenyl]-1,6-dimethyl-6-(1-methylpyrazol-4-yl)hexahydropyrimidine-2,4-dione | 112 | 175 |
| 38 | 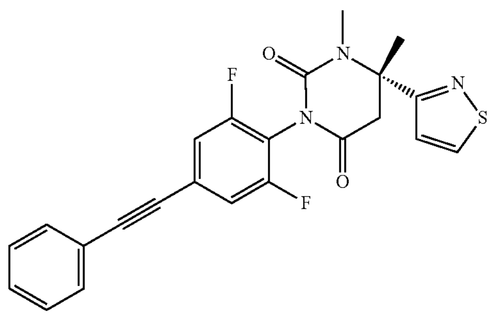 [SMILES: CN1C(=O)N(c2c(F)cc(C#Cc3ccccc3)cc2F)C(=O)C[C@@]1(C)c1ccsn1] | (6S)-3-[2,6-Difluoro-4-(2-phenylethynyl)phenyl]-6-isothiazol-3-yl-1,6-dimethyl-hexahydropyrimidine-2,4-dione | 39 | 152 |
| 39 | 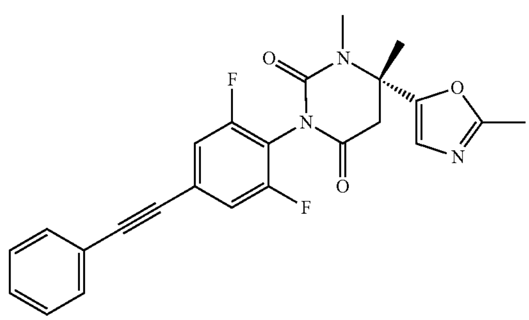 [SMILES: Cc1ncc([C@]2(C)CC(=O)N(c3c(F)cc(C#Cc4ccccc4)cc3F)C(=O)N2C)o1] | (6S)-3-[2,6-Difluoro-4-(2-phenylethynyl)phenyl]-1,6-dimethyl-6-(2-methylthiazol-5-yl)hexahydropyrimidine-2,4-dione | 71 | 148 |
| 40 | 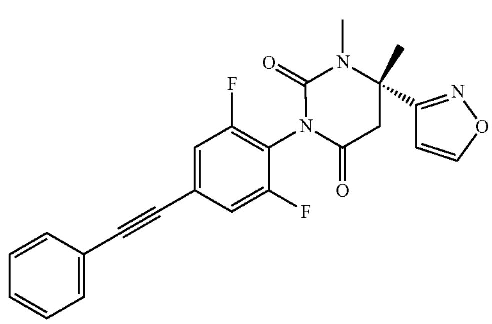 [SMILES: CN1C(=O)N(c2c(F)cc(C#Cc3ccccc3)cc2F)C(=O)C[C@@]1(C)c1ccon1] | (6S)-3-[2,6-Difluoro-4-(2-phenylethynyl)phenyl]-6-isoxazol-3-yl-1,6-dimethyl-hexahydropyrimidine-2,4-dione | 37 | 142 |

-continued

| | Structure | Name | EC$_{50}$ (nM) mGlu4 PAM | Eff. (%) |
|---|---|---|---|---|
| 41 | 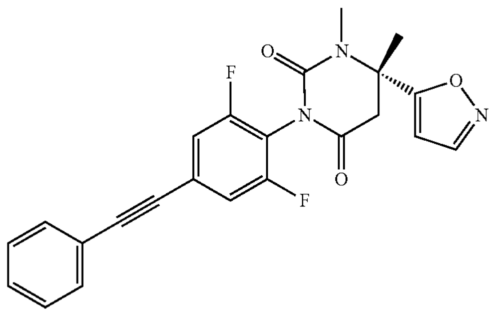 [SMILES: CN1C(=O)N(c2c(F)cc(C#Cc3ccccc3)cc2F)C(=O)C[C@@]1(C)c1ccno1] | (6S)-3-[2,6-Difluoro-4-(2-phenylethynyl)phenyl]-6-isoxazol-5-yl-1,6-dimethyl-hexahydropyrimidine-2,4-dione | 123 | 165 |
| 42 | 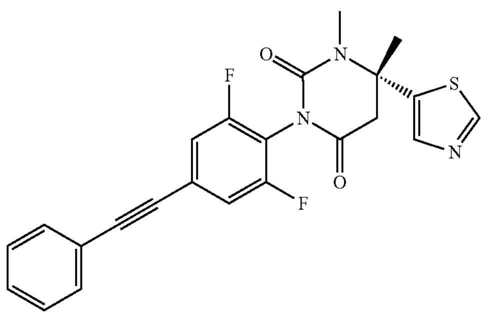 | (6S)-3-[2,6-Difluoro-4-(2-phenylethynyl)phenyl]-1,6-dimethyl-6-thiazol-5-yl-hexahydropyrimidine-2,4-dione | 86 | 135 |
| 43 | 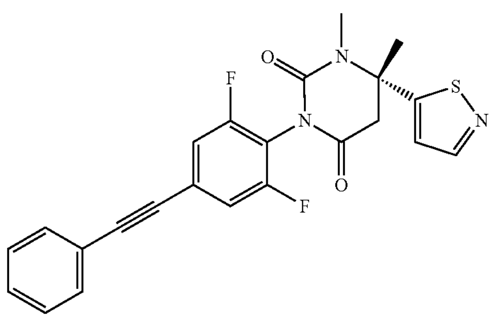 [SMILES: CN1C(=O)N(c2c(F)cc(C#Cc3ccccc3)cc2F)C(=O)C[C@@]1(C)c1ccns1] | (6S)-3-[2,6-Difluoro-4-(2-phenylethynyl)phenyl]-6-isothiazol-5-yl-1,6-dimethyl-hexahydropyrimidine-2,4-dione | 67 | 151 |
| 44 | 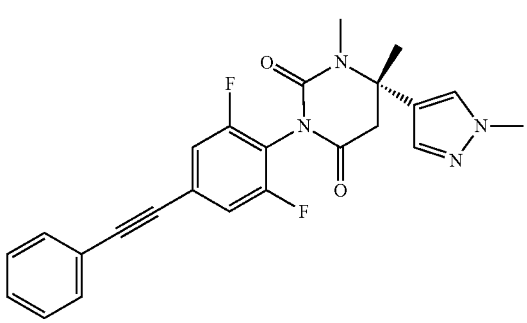 [SMILES: CN1C(=O)N(c2c(F)cc(C#Cc3ccccc3)cc2F)C(=O)C[C@@]1(C)c1cnn(C)c1] | (6S)-3-[2-Chloro-6-fluoro-4-(2-phenylethynyl)phenyl]-1,6-dimethyl-6-(1-methylpyrazol-4-yl)hexahydropyrimidine-2,4-dione | 99 | 153 |

-continued

| | Structure | Name | EC₅₀ (nM) mGlu4 PAM | Eff. (%) |
|---|---|---|---|---|
| 45 | 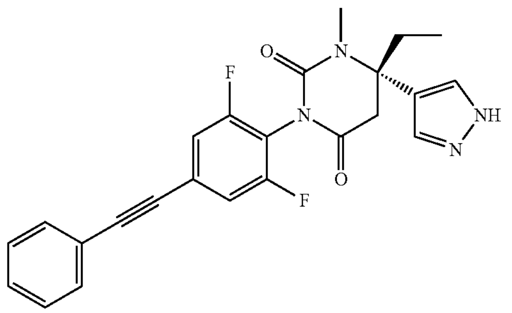 [SMILES: CC[C@@]1(c2cn[nH]c2)CC(=O)N(c2c(F)cc(C#Cc3ccccc3)cc2F)C(=O)N1C] | (6S)-3-[2,6-Difluoro-4-(2-phenylethynyl)phenyl]-6-ethyl-1-methyl-6-(1H-pyrazol-4-yl)hexahydropyrimidine-2,4-dione | 39 | 126 |
| 46 | 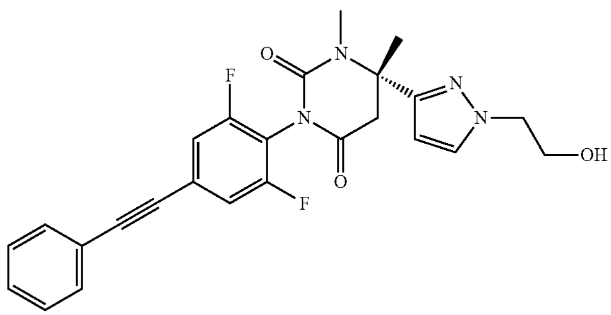 [SMILES: CN1C(=O)N(c2c(F)cc(C#Cc3ccccc3)cc2F)C(=O)C[C@@]1(C)c1ccn(CCO)n1] | (S)-3-(2,6-Difluoro-4-(phenylethynyl)phenyl)-6-(1-(2-hydroxyethyl)-1H-pyrazol-3-yl)-1,6-dimethyldihydropyrimidine-2,4(1H,3H)-dione | 97 | 156 |
| 47 | 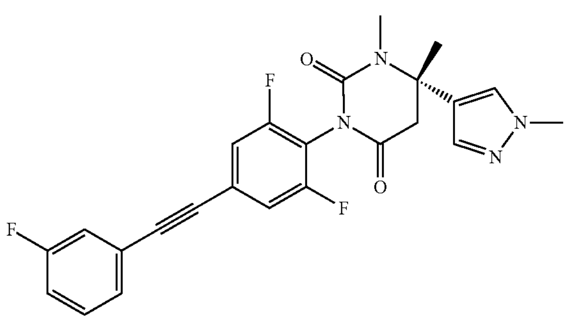 [SMILES: CN1C(=O)N(c2c(F)cc(C#Cc3cccc(F)c3)cc2F)C(=O)C[C@@]1(C)c1cnn(C)c1] | (6S)-3-[2,6-Difluoro-4-[2-(3-fluorophenyl)ethynyl]phenyl]-1,6-dimethyl-6-(1-methylpyrazol-4-yl)hexahydropyrimidine-2,4-dione | 71 | 136 |
| 48 | 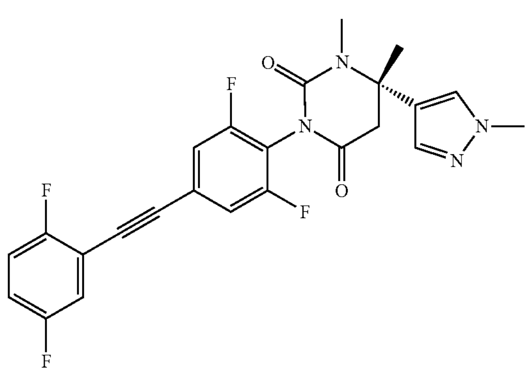 [SMILES: CN1C(=O)N(c2c(F)cc(C#Cc3cc(F)ccc3F)cc2F)C(=O)C[C@@]1(C)c1cnn(C)c1] | (6S)-3-[4-[2-(2,5-Difluorophenyl)ethynyl]-2,6-difluoro-phenyl]-1,6-dimethyl-6-(1-methylpyrazol-4-yl)hexahydropyrimidine-2,4-dione | 79 | 140 |

-continued

| | Structure | Name | EC$_{50}$ (nM) mGlu4 PAM | Eff. (%) |
|---|---|---|---|---|
| 49 | 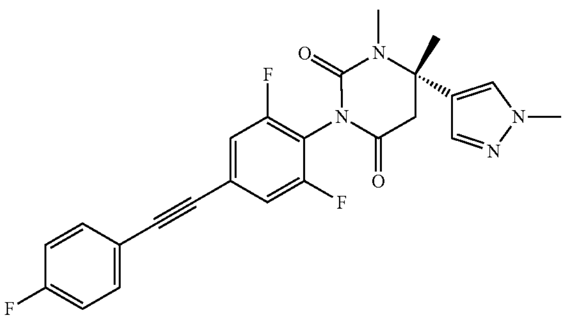 [SMILES: CN1C(=O)N(c2c(F)cc(C#Cc3ccc(F)cc3)cc2F)C(=O)C[C@@]1(C)c1cnn(C)c1] | (6S)-3-[2,6-Difluoro-4-[2-(4-fluorophenyl)ethynyl]phenyl]-1,6-dimethyl-6-(1-methylpyrazol-4-yl)hexahydropyrimidine-2,4-dione | 55 | 142 |
| 50 | 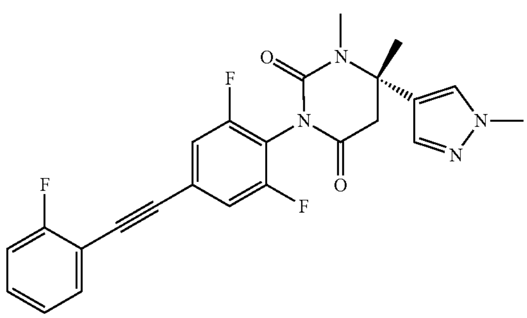 [SMILES: CN1C(=O)N(c2c(F)cc(C#Cc3ccccc3F)cc2F)C(=O)C[C@@]1(C)c1cnn(C)c1] | (6S)-3-[2,6-Difluoro-4-[2-(2-fluorophenyl)ethynyl]phenyl]-1,6-dimethyl-6-(1-methylpyrazol-4-yl)hexahydropyrimidine-2,4-dione | 50 | 147 |
| 51 | 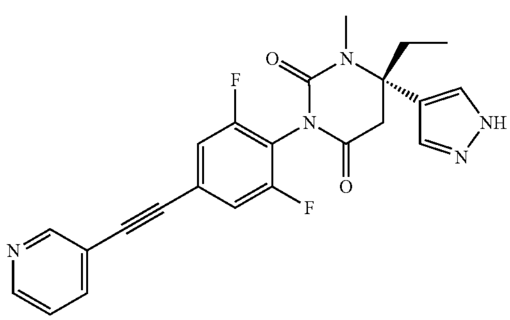 [SMILES: CC[C@@]1(c2cn[nH]c2)CC(=O)N(c2c(F)cc(C#Cc3cccnc3)cc2F)C(=O)N1C] | (6S)-3-[2,6-Difluoro-4-[2-(3-pyridyl)ethynyl]phenyl]-6-ethyl-1-methyl-6-(1H-pyrazol-4-yl)hexahydropyrimidine-2,4-dione | 45 | 136 |
| 52 | 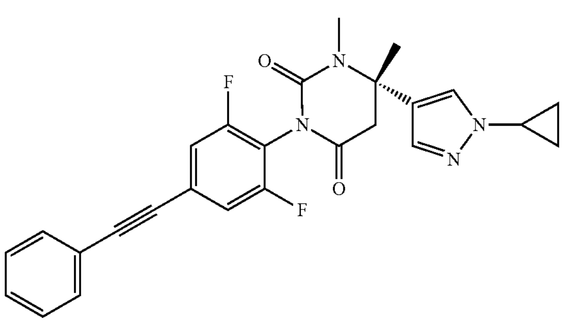 [SMILES: CN1C(=O)N(c2c(F)cc(C#Cc3ccccc3)cc2F)C(=O)C[C@@]1(C)c1cnn(C2CC2)c1] | (6S)-6-(1-Cyclopropylpyrazol-4-yl)-3-[2,6-difluoro-4-(2-phenylethynyl)phenyl]-1,6-dimethyl-hexahydropyrimidine-2,4-dione | 31 | 127 |

-continued

| | Structure | Name | EC$_{50}$ (nM) mGlu4 PAM | Eff. (%) |
|---|---|---|---|---|
| 53 | 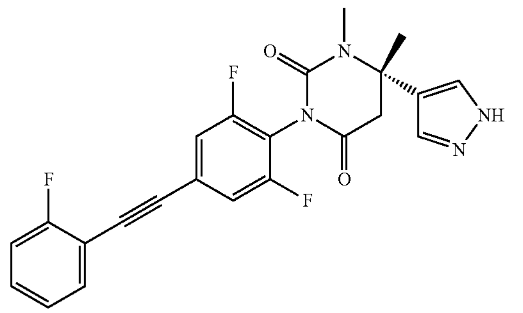 [SMILES: CN1C(=O)N(c2c(F)cc(C#Cc3ccccc3F)cc2F)C(=O)C[C@@]1(C)c1cn[nH]c1] | (6S)-3-[2,6-Difluoro-4-[2-(2-fluorophenyl)ethynyl]phenyl]-1,6-dimethyl-6-(1H-pyrazol-4-yl)hexahydropyrimidine-2,4-dione | 17 | 145 |
| 54 | 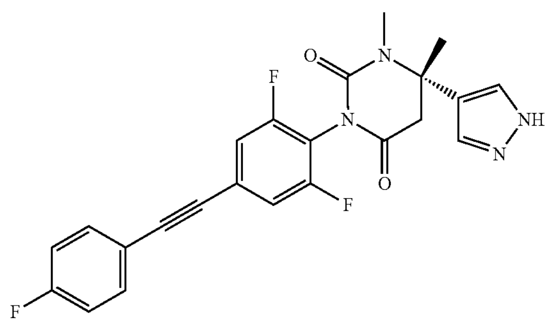 [SMILES: CN1C(=O)N(c2c(F)cc(C#Cc3ccc(F)cc3)cc2F)C(=O)C[C@@]1(C)c1cn[nH]c1] | (6S)-3-[2,6-Difluoro-4-[2-(4-fluorophenyl)ethynyl]phenyl]-1,6-dimethyl-6-(1H-pyrazol-4-yl)hexahydropyrimidine-2,4-dione | 27 | 135 |
| 55 | 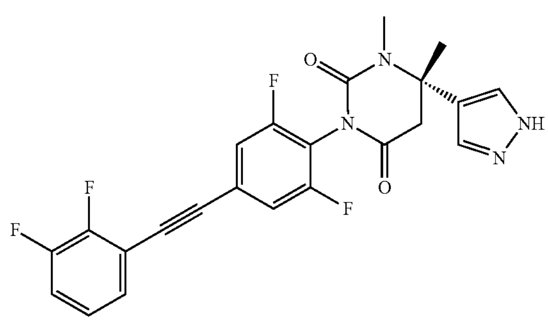 [SMILES: CN1C(=O)N(c2c(F)cc(C#Cc3cccc(F)c3F)cc2F)C(=O)C[C@@]1(C)c1cn[nH]c1] | (6S)-3-[4-[2-(2,3-Difluorophenyl)ethynyl]-2,6-difluoro-phenyl]-1,6-dimethyl-6-(1H-pyrazol-4-yl)hexahydropyrimidine-2,4-dione | 54 | 134 |
| 56 | 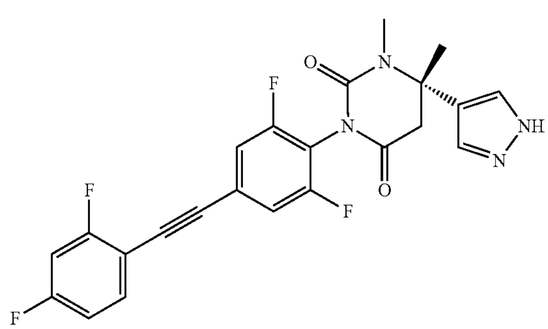 [SMILES: CN1C(=O)N(c2c(F)cc(C#Cc3ccc(F)cc3F)cc2F)C(=O)C[C@@]1(C)c1cn[nH]c1] | (6S)-3-[4-[2-(2,4-Difluorophenyl)ethynyl]-2,6-difluoro-phenyl]-1,6-dimethyl-6-(1H-pyrazol-4-yl)hexahydropyrimidine-2,4-dione | 44 | 143 |

| | | EC$_{50}$ (nM) mGlu4 PAM | Eff. (%) |
|---|---|---|---|
| # | Structure / Name | | |
| 57 | (6S)-3-[4-[2-(2,3-Difluorophenyl)ethynyl]-2,6-difluoro-phenyl]-1,6-dimethyl-6-(1-methylpyrazol-4-yl)hexahydropyrimidine-2,4-dione | 97 | 143 |
| 58 | (6S)-3-[4-[2-(2,4-Difluorophenyl)ethynyl]-2,6-difluoro-phenyl]-1,6-dimethyl-6-(1-methylpyrazol-4-yl)hexahydropyrimidine-2,4-dione | 80 | 139 |
| 59 | (6S)-3-[2,6-Difluoro-4-[2-(3-fluorophenyl)ethynyl]phenyl]-1,6-dimethyl-6-(1H-pyrazol-4-yl)hexahydropyrimidine-2,4-dione | 44 | 160 |
| 60 | (6S)-3-[2,6-Difluoro-4-(2-phenylethynyl)phenyl]-6-[1-(2-hydroxy-2-methyl-propyl)pyrazol-4-yl]-1,6-dimethyl-hexahydropyrimidine-2,4-dione | 47 | 142 |

| | Structure | Name | EC$_{50}$ (nM) mGlu4 PAM | Eff. (%) |
|---|---|---|---|---|
| 61 | 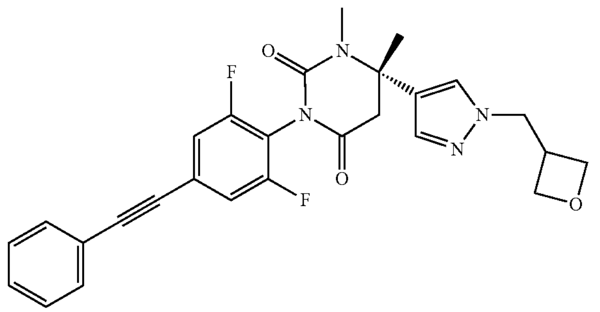 [SMILES: CN1C(=O)N(c2c(F)cc(C#Cc3ccccc3)cc2F)C(=O)C[C@@]1(C)c1cnn(CC2COC2)c1] | (6S)-3-[2,6-Difluoro-4-(2-phenylethynyl)phenyl]-1,6-dimethyl-6-[1-(oxetan-3-ylmethyl)pyrazol-4-yl]hexahydropyrimidine-2,4-dione | 63 | 110 |
| 62 | 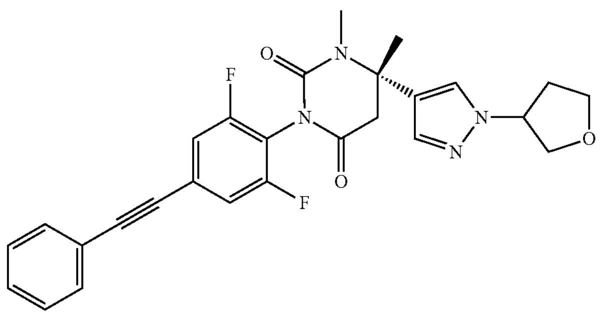 [SMILES: CN1C(=O)N(c2c(F)cc(C#Cc3ccccc3)cc2F)C(=O)C[C@@]1(C)c1cnn(C2CCOC2)c1] | (6S)-3-[2,6-Difluoro-4-(2-phenylethynyl)phenyl]-1,6-dimethyl-6-[1-[(3RS)-tetrahydrofuran-3-yl]pyrazol-4-yl]hexahydropyrimidine-2,4-dione | 71 | 128 |
| 63 | 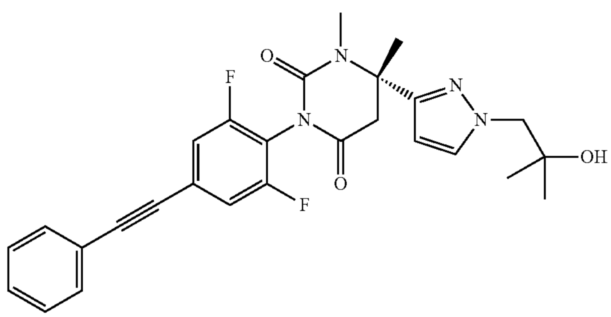 [SMILES: CN1C(=O)N(c2c(F)cc(C#Cc3ccccc3)cc2F)C(=O)C[C@@]1(C)c1ccn(CC(C)(C)O)n1] | (6S)-3-[2,6-Difluoro-4-(2-phenylethynyl)phenyl]-6-[1-(2-hydroxy-2-methyl-propyl)pyrazol-3-yl]-1,6-dimethyl-hexahydropyrimidine-2,4-dione | 71 | 99 |
| 64 | 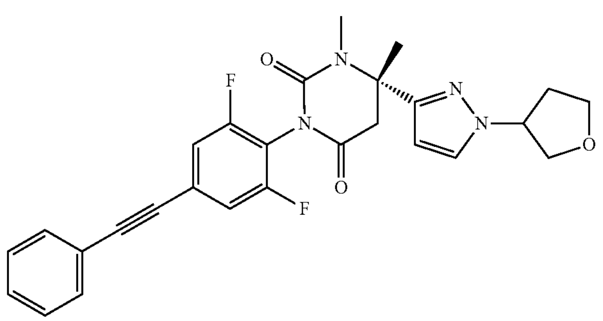 [SMILES: CN1C(=O)N(c2c(F)cc(C#Cc3ccccc3)cc2F)C(=O)C[C@@]1(C)c1ccn(C2CCOC2)n1] | (6S)-3-[2,6-Difluoro-4-(2-phenylethynyl)phenyl]-1,6-dimethyl-6-[1-[(3RS)-tetrahydrofuran-3-yl]pyrazol-3-yl]hexahydropyrimidine-2,4-dione | 88 | 98 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention:

Tablets of the following composition are manufactured in the usual manner:

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXPERIMENTAL SECTION

Example 1

(6S)-3-[2,6-Difluoro-4-(2-phenylethynyl)phenyl]-1,6-dimethyl-6-thiazol-2-yl-hexahydropyrimidine-2,4-dione

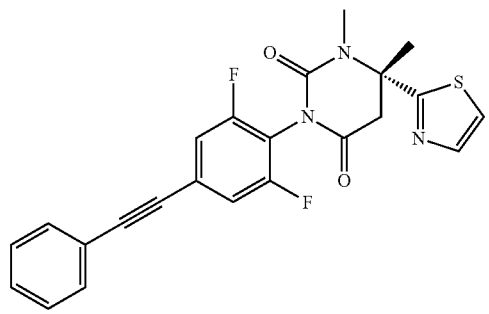 [SMILES: CN1C(=O)N(c2c(F)cc(C#Cc3ccccc3)cc2F)C(=O)C[C@@]1(C)c1nccs1]

Step 1: 2,6-Difluoro-4-phenylethynyl-phenylamine

Bis-(triphenylphosphine)-palladium(II)dichloride (826 mg, 1.18 mmol, 0.02 equiv.) was dissolved in 100 ml THF.

2,6-Difluoro-4-iodoaniline (15 g, 58.8 mmol) and phenylacetylene (7.2 g, 7.8 ml, 70.6 mmol, 1.2 equiv.) were added at room temperature. Triethylamine (29.8 g, 41 ml, 0.29 mol, 5 equiv.), triphenylphosphine (617 mg, 2.35 mmol, 0.04 equiv.) and copper(I)iodide (112 mg, 0.58 mmol, 0.01 equiv.) were added and the mixture was stirred for 1 hour at 60° C. The reaction mixture was cooled and extracted with saturated NaHCO₃ solution and two times with ethyl acetate. The organic layers were washed three times with water, dried over sodium sulfate and evaporated to dryness. The crude product was purified by flash chromatography on a silica gel column eluting with an ethyl acetate:heptane 0:100 to 40:60 gradient. The desired 2,6-difluoro-4-phenylethynyl-phenylamine (12.6 g, 93% yield) was obtained as a yellow solid, MS: m/e=230.1 (M+H⁺).

Step 2: (R,E)-2-Methyl-N-(1-thiazol-2-ylethylidene)propane-2-sulfinamide

2-Acetylthiazole (1.5 g, 11.8 mmol) was dissolved in 20 ml THF. (R)-2-Methylpropane-2-sulfinamide (CAS 196929-78-9) (1.86 g, 15.3 mmol, 1.3 equiv.) and titanium(IV) ethoxide (5.38 g, 4.98 ml, 23.6 mmol, 2.0 equiv.) were added and the mixture was stirred for 16 hours at 65° C. The reaction mixture was cooled and saturated NaHCO₃ solution and ethyl acetate were added. The formed suspension was filtered through Celite) and the filtrate was extracted twice with ethyl acetate. The organic layers were washed brine, dried over sodium sulfate and evaporated to dryness. The crude product was purified by flash chromatography on a silica gel column eluting with an ethyl acetate:heptane 0:100 to 60:40 gradient. The desired (R,E)-2-methyl-N-(1-thiazol-2-ylethylidene)propane-2-sulfinamide (1.73 g, 64% yield) was obtained as a yellow oil, MS: m/e=231.1 (M+H⁺).

Step 3: Methyl (3S)-3-[[(R)-tert-butylsulfinyl]amino]-3-thiazol-2-yl-butanoate

Methyl acetate (1.64 g, 1.76 ml, 22.14 mmol, 3 equiv.) was dissolved in 35 ml dry THF and the solution was cooled to −70° C. LDA (2.0 M in THF/heptane/ethylbenzene) (11 ml, 22.14 mmol, 3 equiv.) was added drop wise at −75° C. to −65° C. and the mixture was stirred for 45 minutes at −70° C. Chlorotitanium triisopropoxide (5.77 g, 22.14 mmol, 3 equiv.) dissolved in 5 ml of dry THF was added drop wise at −75° C. to −65° C. and the mixture was stirred for 45 minutes at −70° C. (R,E)-2-Methyl-N-(1-thiazol-2-ylethylidene)propane-2-sulfinamide (Example 1, step 2) (1.7 g, 7.38 mmol) dissolved in 10 ml of dry THF was added drop wise at −75° C. to −65° C. and the mixture was stirred for 1 hour at −70° C. Saturated NaHCO₃ solution was added and the mixture stirred for 10 minutes. Ethyl acetate was added to the formed suspension and the mixture was stirred for 10 minutes. The formed suspension was filtered through Celite® and the filtrate was extracted twice with ethyl acetate. The organic layers were washed brine, dried over sodium sulfate and evaporated to dryness. The crude product was purified by flash chromatography on a silica gel column eluting with an ethyl acetate:heptane 20:80 to 100:0 gradient. The desired methyl (3S)-3-[[(R)-tert-butylsulfinyl]amino]-3-thiazol-2-yl-butanoate (1.72 g, 77% yield) was obtained as a yellow oil, MS: m/e=305.2 (M+H⁺).

Step 4: Methyl (3S)-3-amino-3-thiazol-2-yl-butanoate

Methyl (3S)-3-[[(R)-tert-butylsulfinyl]amino]-3-thiazol-2-yl-butanoate (Example 1, step 3) (1.7 g, 5.58 mmol) was dissolved in 20 ml MeOH and HCl (4N in dioxane) (22 ml, 89.3 mmol, 15 equiv.) was added. The mixture was stirred for 1 hour at room temperature. The reaction mixture was evaporated and extracted with saturated Na₂CO₃ solution and three times with dichloromethane. The organic layers were combined, dried over sodium sulfate and evaporated to dryness. The crude product was purified by flash chromatography on a silica gel column eluting with a methanol:dichloromethane 0:100 to 10:90 gradient. The desired methyl (3S)-3-amino-3-thiazol-2-yl-butanoate (1.02 g, 93% yield) was obtained as a yellow oil, MS: m/e=201.1 (M+H⁺).

Step 5: Methyl (3S)-3-[[2,6-difluoro-4-(2-phenylethynyl)phenyl]carbamoyl amino]-3-thiazol-2-yl-butanoate 2,6-Difluoro-4-phenylethynyl-phenylamine (Example 1, step 1) (170 mg, 0.75 mmol, 1.5 equiv.) was dissolved in DMF (2.0 ml) and CDI (121 mg, 0.75 mmol, 1.5 equiv.) was added at room temperature. The mixture was stirred for 1 hour at 100° C. To the mixture methyl (3S)-3-amino-3-thiazol-2-yl-butanoate (Example 1, step 4) (100 mg, 0.50 mmol, 1.0 equiv.) was added and stirred for 1 hour at room temperature. The reaction mixture was evaporated with Isolute®. The crude product was purified by flash chromatography eluting with an ethyl acetate:heptane 0:100 to 100:0 gradient. The desired methyl (3S)-3-[[2,6-difluoro-4-(2-phenylethynyl)phenyl]carbamoylamino]-3-thiazol-2-yl-butanoate (155 mg, 68% yield) was obtained as a light yellow solid, MS: m/e=456.2 (M+H⁺).

Step 6: (6S)-3-[2,6-Difluoro-4-(2-phenylethynyl)phenyl]-6-methyl-6-thiazol-2-yl-hexahydropyrimidine-2,4-dione (155 mg, 0.34 mmol) Methyl (3S)-3-[[2,6-difluoro-4-(2-phenylethynyl)phenyl]carbamoylamino]-3-thiazol-2-yl-butanoate (Example 1, step 5) was dissolved in THF (2 ml) and sodium hydride (60% in mineral oil) (20 mg, 0.51 mmol, 1.5 equiv.) was added at room temperature. The mixture was stirred for 1 hour at room temperature. The reaction mixture was extracted with saturated NaHCO₃ solution and two times with ethyl acetate. The organic layers were washed with water and brine, dried over sodium sulfate and evaporated to dryness. The desired (6S)-3-[2,6-difluoro-4-(2-phenylethynyl)phenyl]-6-methyl-6-thiazol-2-yl-hexahydropyrimidine-2,4-dione (122 mg, 85% yield) was obtained as a white solid, MS: m/e=424.1 (M+H⁺).

Step 7: (6S)-3-[2,6-Difluoro-4-(2-phenylethynyl)phenyl]-1,6-dimethyl-6-thiazol-2-yl-hexahydropyrimidine-2,4-dione (122 mg, 0.29 mmol) (6S)-3-[2,6-Difluoro-4-(2-phenylethynyl)phenyl]-6-methyl-6-thiazol-2-yl-hexahydropyrimidine-2,4-dione (Example 1, step 7) was dissolved in DMF (2 ml) and cesium carbonate (141 mg, 0.43 mmol, 1.5 equiv.) and iodomethane (49 mg, 22 ul, 0.35 mmol, 1.2 equiv.) were added at room temperature. The mixture was stirred for 1 hour at room temperature. The reaction mixture was evaporated with Isolute®. The crude product was purified by flash chromatography on a silica gel column eluting with an ethyl acetate:heptane 0:100 to 100:0 gradient. The desired (6S)-3-[2,6-difluoro-4-(2-phenylethynyl)phenyl]-1,6-dimethyl-6-thiazol-2-yl-hexahydropyrimidine-2,4-dione (95 mg, 76% yield) was obtained as a colorless oil, MS: m/e=438.2 (M+H⁺).

Example 2

(6S)-3-[2,6-Difluoro-4-(2-phenylethynyl)phenyl]-1,6-dimethyl-6-(1-methylimidazol-4-yl)hexahydropyrimidine-2,4-dione

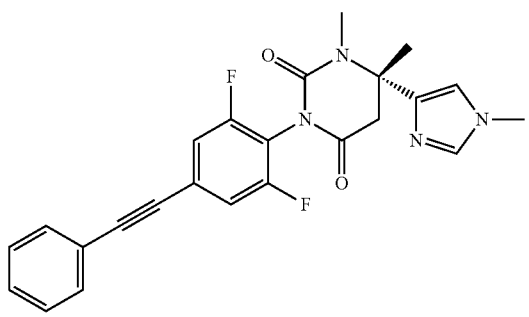 [SMILES: CN1C(=O)N(c2c(F)cc(C#Cc3ccccc3)cc2F)C(=O)C[C@@]1(C)c1cn(C)cn1]

Step 1: Methyl (3S)-3-amino-3-(1-methylimidazol-4-yl)butanoate

The title compound was obtained as a brown oil, MS: m/e=198.2 (M+H$^+$), using chemistry similar to that described in Example 1, step 2,3 and 4 starting from 1-(1-methyl-1H-imidazol-4-yl)ethanone.

Step 2: (6S)-3-[2,6-Difluoro-4-(2-phenylethynyl)phenyl]-1,6-dimethyl-6-(1-methylimidazol-4-yl)hexahydropyrimidine-2,4-dione The title compound was obtained as a white solid, MS: m/e=435.3 (M+H$^+$), using chemistry similar to that described in Example 1, step 5, 6 and 7 starting from 2,6-difluoro-4-phenylethynyl-phenylamine (Example 1, step 1) and methyl (3S)-3-amino-3-(1-methylimidazol-4-yl)butanoate (Example 2, step 1).

Example 3

(6RS)-3-[2,6-Difluoro-4-(2-phenylethynyl)phenyl]-1,6-dimethyl-6-(2-methylthiazol-4-yl)hexahydropyrimidine-2,4-dione

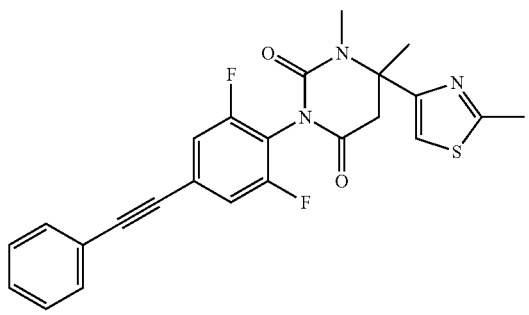 [SMILES: Cc1nc(C2(C)CC(=O)N(c3c(F)cc(C#Cc4ccccc4)cc3F)C(=O)N2C)cs1]

The title compound was obtained as a white solid, MS: m/e=452.2 (M+H$^+$), using chemistry similar to that described in Example 1, step 5 and 3 by using toluene instead of DMF in Example 1 step 5 starting from 2,6-difluoro-4-phenylethynyl-phenylamine (Example 1, step 1) and (3RS)-3-amino-3-(2-methylthiazol-4-yl)butanoic acid dihydro chloride.

Example 4

(6S)-3-[2,6-Difluoro-4-(2-phenylethynyl)phenyl]-1,6-dimethyl-6-(2-methyl-1,2,4-triazol-3-yl)hexahydropyrimidine-2,4-dione

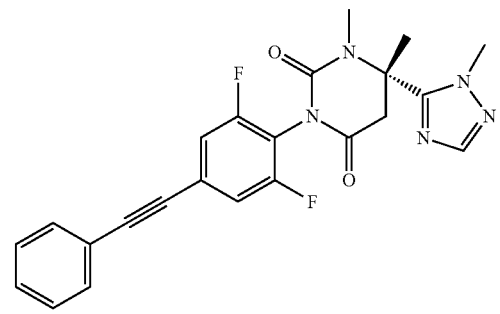 [SMILES: CN1C(=O)N(c2c(F)cc(C#Cc3ccccc3)cc2F)C(=O)C[C@@]1(C)c1ncnn1C]

Step 1: (R,E)-2-Methyl-N-[i-(2-methyl-1,2,4-triazol-3-yl)ethylidene]propane-2-sulfinamide The title compound was obtained as a yellow solid, MS: m/e=229.1 (M+H$^+$), using chemistry similar to that described in Example 1, step 2 from 1-(1-methyl-1H-1,2,4-triazol-5-yl)ethanone and (R)-2-methylpropane-2-sulfinamide (CAS 196929-78-9).

Step 2: Ethyl (3S)-3-[[(R)-tert-butylsulfinyl]amino]-3-(2-methyl-1,2,4-triazol-3-yl)butanoate Activated zinc (0.9 g, 13.8 mmol, 3 equiv.) was suspended in 15 ml THF and copper (I) chloride (470 mg, 4.6 mmol, 1 equiv.) was added. The mixture was stirred for 30 minutes at 60° C. and ethyl 2-bromoacetate (1.3 ml, 1.96 g, 11.5 mmol, 2.5 equiv.) was added dropwise. After 30 minutes at 60° C. the mixture was cooled to 0-5° C. and a mixture of (R,E)-2-methyl-N-[1-(2-methyl-1,2,4-triazol-3-yl)ethylidene]propane-2-sulfinamide (Example 4, step 1) (1.05 g, 4.6 mmol) in 5 ml THF was added dropwise at 0-5° C. The mixture was stirred for 1 hour 0-5° C. Saturated NH$_4$Cl solution and ethyl acetate were added and the formed suspension was filtered through Celite®. The filtrate was extracted twice with ethyl acetate. The organic layers were washed brine, dried over sodium sulfate and evaporated to dryness. The crude product was purified by flash chromatography on a silica gel column eluting with an ethyl acetate:heptane 0:100 to 100:0 gradient. The desired ethyl (3S)-3-[[(R)-tert-butylsulfinyl]amino]-3-(2-methyl-1,2,4-triazol-3-yl)butanoate (510 mg, 60% purity, 21% yield) was obtained as a yellow oil, MS: m/e=317.2 (M+H$^+$).

Step 3: Ethyl (3S)-3-amino-3-(2-methyl-1,2,4-triazol-3-yl)butanoate

The title compound was obtained as a light yellow liquid, MS: m/e=213.1 (M+H$^+$), using chemistry similar to that described in Example 1, step 4 from ethyl (3S)-3-[[(R)-tert-butylsulfinyl]amino]-3-(2-methyl-1,2,4-triazol-3-yl)butanoate (Example 4, step 2).

Step 4: (6S)-3-[2,6-Difluoro-4-(2-phenylethyl)phenyl]-1,6-dimethyl-6-(2-methyl-1,2,4-triazol-3-yl)hexahydropyrimidine-2,4-dione The title compound was obtained as a white solid, MS: m/e=436.3 (M+H⁺), using chemistry similar to that described in Example 1, step 5, 6 and 7 by using triphosgene in toluene instead of CDI in DMF starting from 2,6-difluoro-4-phenylethynyl-phenylamine (Example 1, step 1) and ethyl (3S)-3-amino-3-(2-methyl-1,2,4-triazol-3-yl)butanoate (Example 4, step 3).

Example 5

(6S)-3-[2,6-Difluoro-4-(2-phenylethynyl)phenyl]-6-methyl-6-(1-methylpyrazol-4-yl)hexahydropyrimidine-2,4-dione

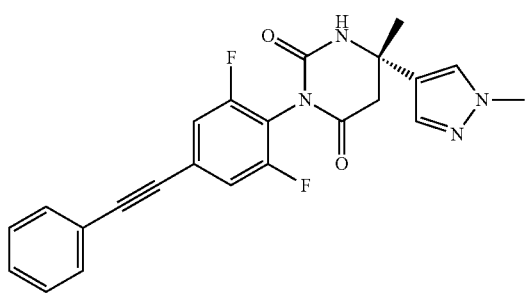 [SMILES: Cn1cc([C@]2(C)CC(=O)N(c3c(F)cc(C#Cc4ccccc4)cc3F)C(=O)N2)cn1]

Step 1: Methyl (3S)-3-amino-3-(1-methylpyrazol-4-yl)butanoate

The title compound was obtained as a brown oil, MS: m/e=119.1 (M+H⁺), using chemistry similar to that described in Example 1, step 2,3 and 4 starting from 1-(1-methyl-1H-pyrazol-4-yl)ethanone.

Step 2: (6S)-3-[2,6-Difluoro-4-(2-phenylethynyl)phenyl]-6-methyl-6-(1-methylpyrazol-4-yl)hexahydropyrimidine-2,4-dione The title compound was obtained as a light yellow solid, MS: m/e=421.2 (M+H⁺), using chemistry similar to that described in Example 1, step 5 and 6 starting from 2,6-difluoro-4-phenylethynyl-phenylamine (Example 1, step 1) and methyl (3S)-3-amino-3-(1-methylpyrazol-4-yl)butanoate (Example 5, step 1).

Example 6

(6S)-3-[2,6-Difluoro-4-(2-phenylethynyl)phenyl]-1,6-dimethyl-6-(1-methylpyrazol-4-yl)hexahydropyrimidine-2,4-dione

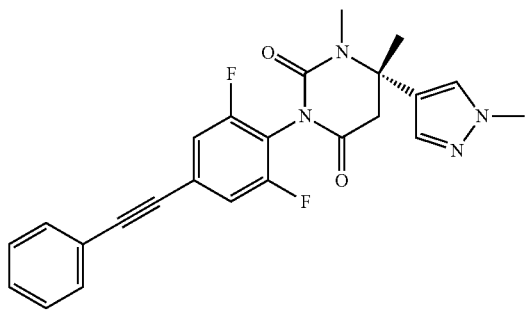 [SMILES: CN1C(=O)N(c2c(F)cc(C#Cc3ccccc3)cc2F)C(=O)C[C@@]1(C)c1cnn(C)c1]

The title compound was obtained as a yellow oil, MS: m/e=435.3 (M+H⁺), using chemistry similar to that described in Example 1, step 7 starting from (6S)-3-[2,6-difluoro-4-(2-phenylethynyl)phenyl]-6-methyl-6-(1-methylpyrazol-4-yl)hexahydropyrimidine-2,4-dione (Example 5) and iodomethane.

Example 7

(6S)-3-[2,6-Difluoro-4-(2-phenylethynyl)phenyl]-1,6-dimethyl-6-(2-methylpyrazol-3-yl)hexahydropyrimidine-2,4-dione

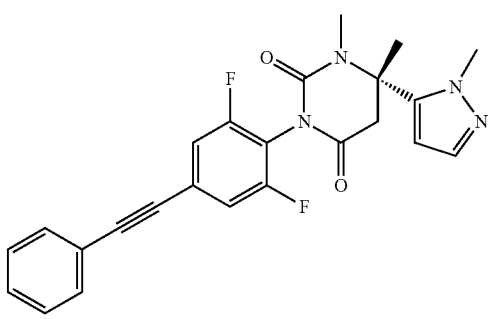

Step 1: Methyl (3S)-3-amino-3-(2-methylpyrazol-3-yl)butanoate

The title compound was obtained as an orange oil, MS: m/e=199.1 (M+H⁺), using chemistry similar to that described in Example 1, step 2,3 and 4 starting from 1-(1-methyl-1H-pyrazol-5-yl)ethanone.

Step 2: (6S)-3-[2,6-Difluoro-4-(2-phenylethynyl)phenyl]-1,6-dimethyl-6-(2-methylpyrazol-3-yl)hexahydropyrimidine-2,4-dione The title compound was obtained as a white solid, MS: m/e=435.3 (M+H⁺), using chemistry similar to that described in Example 1, step 5, 6 and 7 starting from 2,6-difluoro-4-phenylethynyl-phenylamine (Example 1, step 1) and methyl (3S)-3-amino-3-(2-methylpyrazol-3-yl)butanoate (Example 7, step 1).

Example 8

(6S)-3-[2,6-Difluoro-4-(2-phenylethynyl)phenyl]-1,6-dimethyl-6-(1-methylindazol-3-yl)hexahydropyrimidine-2,4-dione

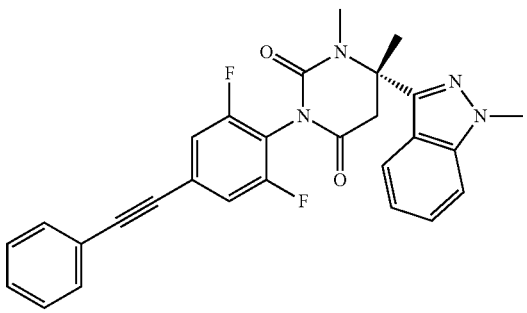 [SMILES: CN1C(=O)N(c2c(F)cc(C#Cc3ccccc3)cc2F)C(=O)C[C@@]1(C)c1nn(C)c2ccccc12]

Step 1: Methyl (3S)-3-amino-3-(1-methylindazol-3-yl)butanoate

The title compound was obtained as a light brown oil, MS: m/e=248.2 (M+H⁺), using chemistry similar to that described in Example 1, step 2,3 and 4 starting from 1-(1-methyl-1H-indazol-3-yl)ethanone (CAS 69271-42-7).

Step 2: (6S)-3-[2,6-Difluoro-4-(2-phenylethynyl)phenyl]-1,6-dimethyl-6-(1-methylindazol-3-yl)hexahydropyrimidine-2,4-dione The title compound was obtained as a white solid, MS: m/e=485.2 (M+H⁺), using chemistry similar to that described in Example 1, step 5 and 7 starting from 2,6-difluoro-4-phenylethynyl-phenylamine (Example 1, step 1) and methyl (3S)-3-amino-3-(1-methylindazol-3-yl)butanoate (Example 8, step 1).

Example 9

(6S)-3-[2,6-Difluoro-4-(2-phenylethynyl)phenyl]-1,6-dimethyl-6-(1-methylpyrrolo[2,3-b]pyridin-3-yl)hexahydropyrimidine-2,4-dione

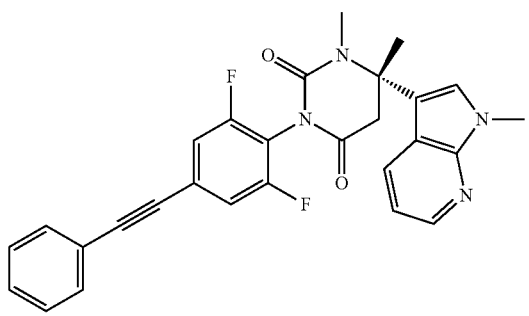 [SMILES: CN1C(=O)N(c2c(F)cc(C#Cc3ccccc3)cc2F)C(=O)C[C@@]1(C)c1cn(C)c2ncccc12]

Step 1: Methyl (3S)-3-amino-3-(1-methylpyrrolo[2,3-b]pyridin-3-yl)butanoate

The title compound was obtained as an orange oil, MS: m/e=249.2 (M+H⁺), using chemistry similar to that described in Example 1, step 2,3 and 4 starting from 1-(1-methyl-1H-pyrrolo[2,3-b]pyridin-3-yl)ethanone (CAS 1515505-67-5).

Step 2: (6S)-3-[2,6-Difluoro-4-(2-phenylethynyl)phenyl]-1,6-dimethyl-6-(1-methylpyrrolo[2,3-b]pyridin-3-yl)hexahydropyrimidine-2,4-dione The title compound was obtained as a white solid, MS: m/e=485.3 (M+H⁺), using chemistry similar to that described in Example 1, step 5, 6 and 7 starting from 2,6-difluoro-4-phenylethynyl-phenylamine (Example 1, step 1) and methyl (3S)-3-amino-3-(1-methylpyrrolo[2,3-b]pyridin-3-yl)butanoate (Example 9, step 1).

Example 10

(6S)-3-[2,6-Difluoro-4-(2-phenylethynyl)phenyl]-1,6-dimethyl-6-(1H-pyrazol-3-yl hexahydropyrimidine-2,4-dione

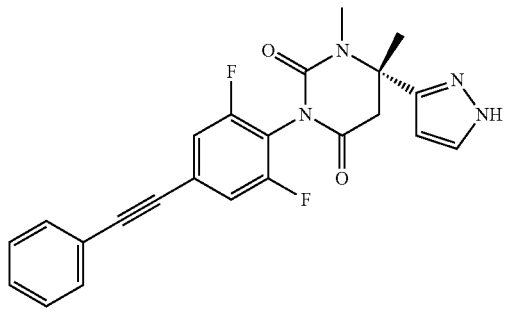 [SMILES: CN1C(=O)N(c2c(F)cc(C#Cc3ccccc3)cc2F)C(=O)C[C@@]1(C)c1cc[nH]n1]

Step 1: 1-(1-((2-(Trimethylsilyl)ethoxy)methyl)-1H-pyrazol-3-yl)ethanone 1-(1H-Pyrazol-3-yl)ethanone hydrochloride (1 g, 6.82 mmol) was dissolved in THF (20 ml) and cooled to 0-5° C. Sodium hydride (60% dispersion in mineral oil) (655 mg, 15.0 mmol, 2.2 equiv.) was added carefully in portions and the mixture was stirred for 30 minutes at room temperature. The reaction mixture was cooled again to 0-5° C. and (2-(chloromethoxy)ethyl)trimethylsilane (1.45 ml, 1.36 g, 8.2 mmol, 1.2 equiv.) was added and the mixture was stirred for 2 hours at room temperature. The reaction mixture was extracted carefully with saturated NaHCO₃ solution and twice with ethyl acetate. The organic layers were washed with brine, dried over sodium sulfate and evaporated to dryness. The desired 1-(1-((2-(trimethylsilyl)ethoxy)methyl)-1H-pyrazol-3-yl)ethanone (1.38 g, 84% yield) was obtained as a colorless oil, MS: m/e=241.3 (M+H⁺).

Step 2: Methyl (3S)-3-amino-3-[1-(2-trimethylsilylethoxymethyl)pyrazol-3-yl]butanoate The title compound was obtained as a yellow oil, MS: m/e=314.2 (M+H⁺), using chemistry similar to that described in Example 1, step 2,3 and 4 starting from 1-(1-((2-(trimethylsilyl)ethoxy)methyl)-1H-pyrazol-3-yl)ethanone (Example 10, step 1) by stirring the cleavage step with HCl just 10 minutes instead of 1 hour.

Step 3: (6S)-3-[2,6-Difluoro-4-(2-phenylethynyl)phenyl]-1,6-dimethyl-6-[1-(2-trimethylsilylethoxymethyl)pyrazol-3-yl]hexahydropyrimidine-2,4-dione The title compound was obtained as a colorless oil, MS: m/e=551.1 (M+H⁺), using chemistry similar to that described in Example 1, step 5, 6 and 7 starting from 2,6-difluoro-4-phenylethynyl-phenylamine (Example 1, step 1) and methyl (3S)-3-amino-3-[1-(2-trimethylsilylethoxymethyl)pyrazol-3-yl]butanoate (Example 10, step 2).

Step 4: (6S)-3-[2,6-Difluoro-4-(2-phenylethynyl)phenyl]-1,6-dimethyl-6-(1H-pyrazol-3-yl)hexahydropyrimidine-2,4-dione The title compound was obtained as a colorless oil, MS: m/e=421.2 (M+H⁺), using chemistry similar to that described in Example 1, step 4 by stirring the reaction for 2 hours at 60° C. instead of room temperature starting from (6S)-3-[2,6-difluoro-4-(2-phenylethynyl)phenyl]-1,6-dimethyl-6-[1-(2-trimethylsilylethoxymethyl)pyrazol-3-yl]hexahydropyrimidine-2,4-dione (Example 10, step 3).

Example 11

(6S)-3-[2,6-Difluoro-4-(2-phenylethynyl)phenyl]-1,6-dimethyl-6-(3-methylimidazol-4-yl)hexahydropyrimidine-2,4-dione

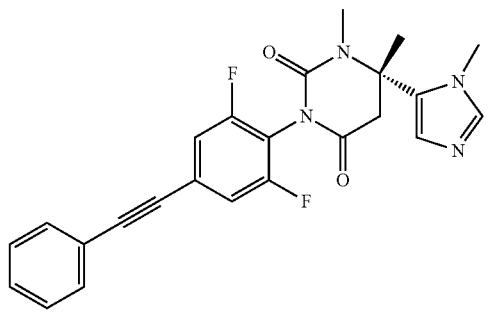 [SMILES: CN1C(=O)N(c2c(F)cc(C#Cc3ccccc3)cc2F)C(=O)C[C@@]1(C)c1cncn1C]

Step 1: Methyl (3S)-3-amino-3-(3-methylimidazol-4-yl)butanoate

The title compound was obtained as an orange oil, MS: m/e=198.2 (M+H⁺), using chemistry similar to that described in Example 1, step 2,3 and 4 starting from 1-(1-methyl-1H-imidazol-5-yl)ethanone.

Step 2: (6S)-3-[2,6-Difluoro-4-(2-phenylethynyl)phenyl]-1,6-dimethyl-6-(3-methylimidazol-4-yl)hexahydropyrimidine-2,4-dione The title compound was obtained as a white solid, MS: m/e=435.3 (M+H⁺), using chemistry similar to that described in Example 1, step 5, 6 and 7 starting from 2,6-difluoro-4-phenylethynyl-phenylamine (Example 1, step 1) and methyl (3S)-3-amino-3-(3-methylimidazol-4-yl)butanoate (Example 11, step 1).

Example 12

(6S)-3-[2,6-Difluoro-4-(2-phenylethynyl)phenyl]-1-ethyl-6-methyl-6-(1-methylpyrazol-4-yl)hexahydropyrimidine-2,4-dione

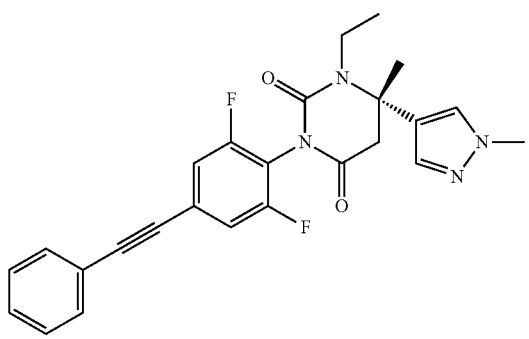 [SMILES: CCN1C(=O)N(c2c(F)cc(C#Cc3ccccc3)cc2F)C(=O)C[C@@]1(C)c1cnn(C)c1]

The title compound was obtained as a white solid, MS: m/e=449.3 (M+H⁺), using chemistry similar to that described in Example 1, step 7 starting from (6S)-3-[2,6-difluoro-4-(2-phenylethynyl)phenyl]-6-methyl-6-(1-methylpyrazol-4-yl)hexahydropyrimidine-2,4-dione (Example 5) and iodoethane.

Example 13

(6S)-3-[2,6-Difluoro-4-(2-phenylethynyl)phenyl]-6-(1-ethylpyrazol-4-yl)-1,6-dimethyl-hexahydropyrimidine-2,4-dione

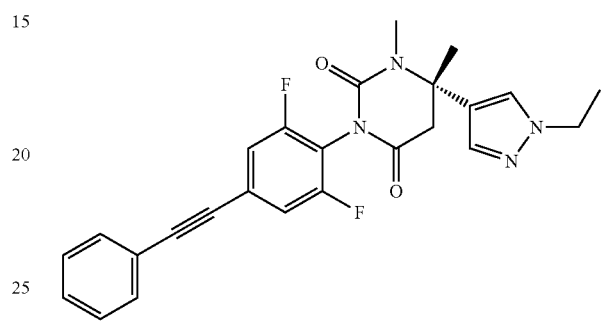

Step 1: Methyl (3S)-3-amino-3-(1-ethylpyrazol-4-yl)butanoate

The title compound was obtained as a yellow oil, MS: m/e=213.1 (M+H⁺), using chemistry similar to that described in Example 1, step 2,3 and 4 starting from 1-(1-ethylpyrazol-4-yl)ethanone.

Step 2: (6S)-3-[2,6-Difluoro-4-(2-phenylethynyl)phenyl]-6-(1-ethylpyrazol-4-yl)-1,6-dimethyl-hexahydropyrimidine-2,4-dione The title compound was obtained as a white solid, MS: m/e=449.3 (M+H⁺), using chemistry similar to that described in Example 1, step 5, 6 and 7 starting from 2,6-difluoro-4-phenylethynyl-phenylamine (Example 1, step 1) and methyl (3S)-3-amino-3-(1-ethylpyrazol-4-yl)butanoate (Example 13, step 1).

Example 14

(6S)-3-[2,6-Difluoro-4-(2-phenylethynyl)phenyl]-1,6-dimethyl-6-pyrazolo[1,5-a]pyridin-3-yl-hexahydropyrimidine-2,4-dione

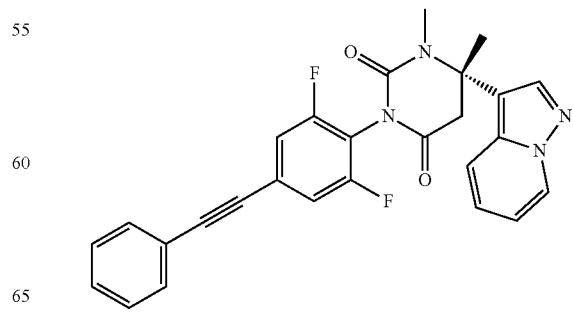

Step 1: Methyl (3S)-3-amino-3-pyrazolo[1,5-a]pyridin-3-yl-butanoate

The title compound was obtained as a yellow oil, MS: m/e=217.2 (M-NH$_2$+H$^+$), using chemistry similar to that described in Example 1, step 2,3 and 4 starting from 1-(pyrazolo[1,5-a]pyridin-3-yl)ethanone (CAS 59942-95-9).

Step 2: (6S)-3-[2,6-Difluoro-4-(2-phenylethynyl)phenyl]-1,6-dimethyl-6-pyrazolo[1,5-a]pyridin-3-yl-hexahydropyrimidine-2,4-dione The title compound was obtained as a light yellow solid, MS: m/e=471.3 (M+H$^+$), using chemistry similar to that described in Example 1, step 5, 6 and 7 starting from 2,6-difluoro-4-phenylethynyl-phenylamine (Example 1, step 1) and methyl (3S)-3-amino-3-pyrazolo[1,5-a]pyridin-3-yl-butanoate (Example 14, step 1).

Example 15

(6S)-3-[2,6-Difluoro-4-(2-phenylethynyl)phenyl]-6-isothiazol-4-yl-1,6-dimethyl-hexahydropyrimidine-2,4-dione

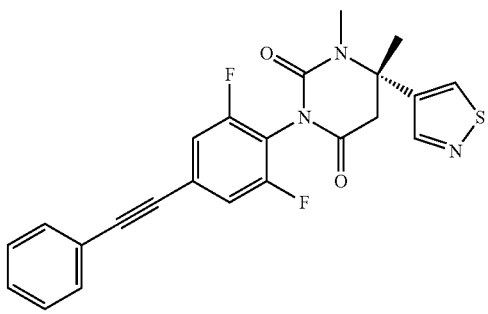 [SMILES: CN1C(=O)N(c2c(F)cc(C#Cc3ccccc3)cc2F)C(=O)C[C@@]1(C)c1cnsc1]

Step 1: Methyl (3S)-3-amino-3-isothiazol-4-yl-butanoate

The title compound was obtained as a yellow oil, MS: m/e=201.1 (M+H$^+$), using chemistry similar to that described in Example 1, step 2,3 and 4 starting from 1-(isothiazol-4-yl)ethanone (CAS 88511-36-8).

Step 2: (6S)-3-[2,6-Difluoro-4-(2-phenylethynyl)phenyl]-6-isothiazol-4-yl-1,6-dimethyl-hexahydropyrimidine-2,4-dione The title compound was obtained as a white foam, MS: m/e=438.2 (M+H$^+$), using chemistry similar to that described in Example 1, step 5, 6 and 7 starting from 2,6-difluoro-4-phenylethynyl-phenylamine (Example 1, step 1) and methyl (3S)-3-amino-3-isothiazol-4-yl-butanoate (Example 15, step 1).

Example 16

(6S)-3-[2,6-Difluoro-4-(2-phenylethynyl)phenyl]-1,6-dimethyl-6-(1H-pyrazol-4-yl)hexahydropyrimidine-2,4-dione

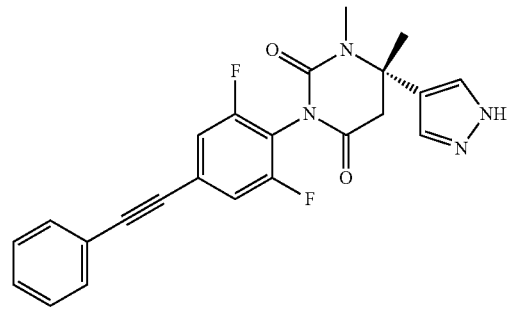 [SMILES: CN1C(=O)N(c2c(F)cc(C#Cc3ccccc3)cc2F)C(=O)C[C@@]1(C)c1cn[nH]c1]

Step 1: 1-(1-((2-(Trimethylsilyl)ethoxy)methyl)-1H-pyrazol-4-yl)ethanone

The title compound was obtained as a light yellow liquid, MS: m/e=241.2 (M+H$^+$), using chemistry similar to that described in Example 10, step 1 starting from 1-(1H-pyrazol-4-yl)ethanone.

Step 2: Methyl (3S)-3-amino-3-[1-(2-trimethylsilylethoxymethyl)pyrazol-4-yl]butanoate The title compound was obtained as a white solid, MS: m/e=315.2 (M+H$^+$), using chemistry similar to that described in Example 1, step 2,3 and 4 starting from 1-(1-((2-(trimethylsilyl)ethoxy)methyl)-1H-pyrazol-4-yl)ethanone (Example 16, step 1) by stirring the cleavage step with HCl just 10 minutes instead of 1 hour.

Step 3: (6S)-3-[2,6-Difluoro-4-(2-phenylethynyl)phenyl]-1,6-dimethyl-6-[1-(2-trimethylsilylethoxymethyl)pyrazol-4-yl]hexahydropyrimidine-2,4-dione The title compound was obtained as a yellow oil, MS: m/e=551.3 (M+H$^+$), using chemistry similar to that described in Example 1, step 5, 6 and 7 starting from 2,6-difluoro-4-phenylethynyl-phenylamine (Example 1, step 1) and methyl (3S)-3-amino-3-[1-(2-trimethylsilylethoxymethyl)pyrazol-4-yl]butanoate (Example 16, step 2).

Step 4: (6S)-3-[2,6-Difluoro-4-(2-phenylethynyl)phenyl]-1,6-dimethyl-6-(1H-pyrazol-4-yl)hexahydropyrimidine-2,4-dione The title compound was obtained as a colorless oil, MS: m/e=421.2 (M+H$^+$), using chemistry similar to that described in Example 1, step 4 starting from (6S)-3-[2,6-difluoro-4-(2-phenylethynyl)phenyl]-1,6-dimethyl-6-[1-(2-trimethylsilylethoxymethyl)pyrazol-4-yl]hexahydropyrimidine-2,4-dione (Example 16, step 3).

Example 17

(6S)-3-[2,6-Difluoro-4-(2-phenylethynyl)phenyl]-1,6-dimethyl-6-(1-methylpyrazolo[3,4-b]pyridin-3-yl)hexahydropyrimidine-2,4-dione

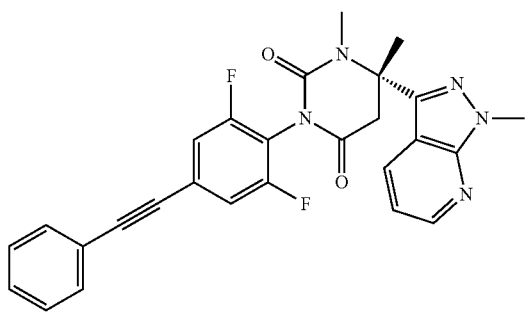 [SMILES: CN1C(=O)N(c2c(F)cc(C#Cc3ccccc3)cc2F)C(=O)C[C@@]1(C)c1nn(C)c2ncccc12]

Step 1: Methyl (3S)-3-amino-3-(1-methylpyrazolo[3,4-b]pyridin-3-yl)butanoate The title compound was obtained as a yellow oil, MS: m/e=249.2 (M+H⁺), using chemistry similar to that described in Example 1, step 2,3 and 4 starting from 1-(1-methyl-1H-pyrazolo[3,4-b]pyridin-3-yl)ethanone (CAS 1638593-63-1).

Step 2: (6S)-3-[2,6-Difluoro-4-(2-phenylethynyl)phenyl]-1,6-dimethyl-6-(1-methylpyrazolo[3,4-b]pyridin-3-yl)hexahydropyrimidine-2,4-dione The title compound was obtained as a white solid, MS: m/e=486.3 (M+H⁺), using chemistry similar to that described in Example 1, step 5, 6 and 7 starting from 2,6-difluoro-4-phenylethynyl-phenylamine (Example 1, step 1) and methyl (3S)-3-amino-3-(1-methylpyrazolo[3,4-b]pyridin-3-yl)butanoate (Example 17, step 1).

Example 18

(6S)-3-[2,6-Difluoro-4-(2-phenylethynyl)phenyl]-6-ethyl-1-methyl-6-(1-methylpyrazol-4-yl)hexahydropyrimidine-2,4-dione

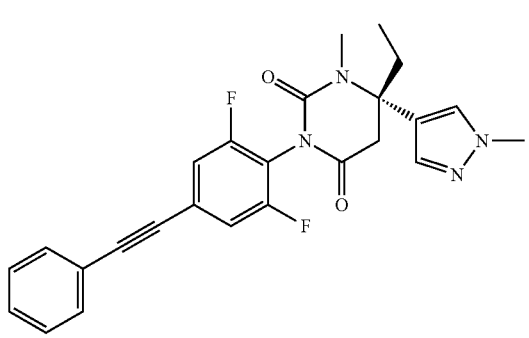 [SMILES: CC[C@@]1(c2cnn(C)c2)CC(=O)N(c2c(F)cc(C#Cc3ccccc3)cc2F)C(=O)N1C]

Step 1: Methyl (3S)-3-amino-3-(1-methylpyrazol-4-yl)pentanoate

The title compound was obtained as a yellow oil, MS: m/e=213.1 (M+H⁺), using chemistry similar to that described in Example 1, step 2,3 and 4 starting from 1-(1-methyl-1H-pyrazol-4-yl)propan-1-one (CAS 1007518-49-1).

Step 2: (6S)-3-[2,6-Difluoro-4-(2-phenylethynyl)phenyl]-6-ethyl-1-methyl-6-(1-methylpyrazol-4-yl)hexahydropyrimidine-2,4-dione The title compound was obtained as a white solid, MS: m/e=449.2 (M+H⁺), using chemistry similar to that described in Example 1, step 5, 6 and 7 starting from 2,6-difluoro-4-phenylethynyl-phenylamine (Example 1, step 1) and methyl (3S)-3-amino-3-(1-methylpyrazol-4-yl)pentanoate (Example 18, step 1).

Example 19

(6S)-3-[2,6-Difluoro-4-(2-phenylethynyl)phenyl]-6-(1-isopropylpyrazol-4-yl)-1,6-dimethyl-hexahydropyrimidine-2,4-dione

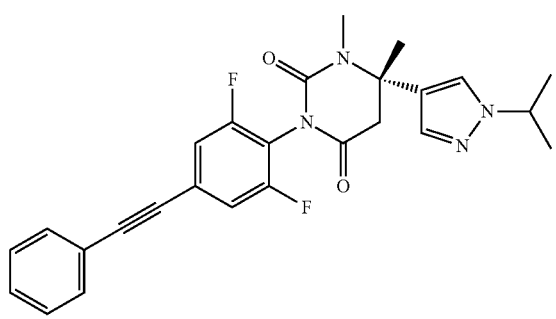 [SMILES: CC(C)n1cc([C@]2(C)CC(=O)N(c3c(F)cc(C#Cc4ccccc4)cc3F)C(=O)N2C)cn1]

The title compound was obtained as a white solid, MS: m/e=463.3 (M+H⁺), using chemistry similar to that described in Example 1, step 7 starting from (6S)-3-[2,6-difluoro-4-(2-phenylethynyl)phenyl]-1,6-dimethyl-6-(1H-pyrazol-4-yl)hexahydropyrimidine-2,4-dione (Example 16) and 2-iodopropane.

Example 20

(6S)-3-[2,6-Difluoro-4-(2-phenylethynyl)phenyl]-6-[1-(2-methoxyethyl)pyrazol-4-yl]-1,6-dimethyl-hexahydropyrimidine-2,4-dione

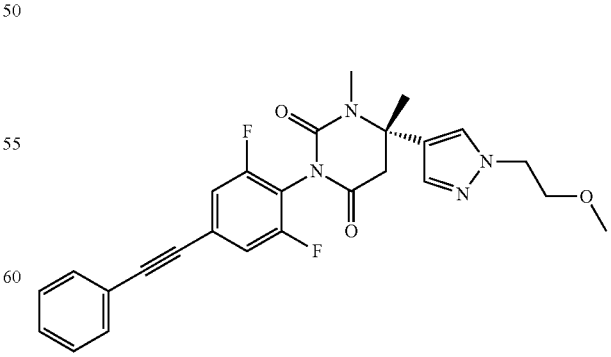

The title compound was obtained as a colorless oil, MS: m/e=479.2 (M+H⁺), using chemistry similar to that described in Example 1, step 7 starting from (6S)-3-[2,6- difluoro-4-(2-phenylethynyl)phenyl]-1,6-dimethyl-6-(1H-pyrazol-4-yl)hexahydropyrimidine-2,4-dione (Example 16) and 1-iodo-2-methoxyethane.

Example 21

(6S)-3-[2,6-Difluoro-4-(2-phenylethynyl)phenyl]-6-[1-(3-methoxypropyl)pyrazol-4-yl]-1,6-dimethyl-hexahydropyrimidine-2,4-dione

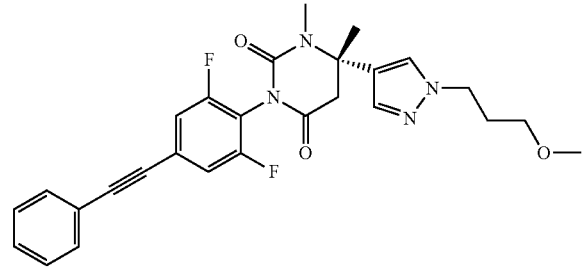 [SMILES: COCCCn1cc([C@]2(C)CC(=O)N(c3c(F)cc(C#Cc4ccccc4)cc3F)C(=O)N2C)cn1]

The title compound was obtained as a colorless oil, MS: m/e=493.2 (M+H$^+$), using chemistry similar to that described in Example 1, step 7 starting from (6S)-3-[2,6-difluoro-4-(2-phenylethynyl)phenyl]-1,6-dimethyl-6-(1H-pyrazol-4-yl)hexahydropyrimidine-2,4-dione (Example 16) and 1-bromo-3-methoxypropane.

Example 22

(6S)-3-[2,6-Difluoro-4-(2-phenylethynyl)phenyl]-6-[1-(3-hydroxypropyl)pyrazol-4-yl]-1,6-dimethyl-hexahydropyrimidine-2,4-dione

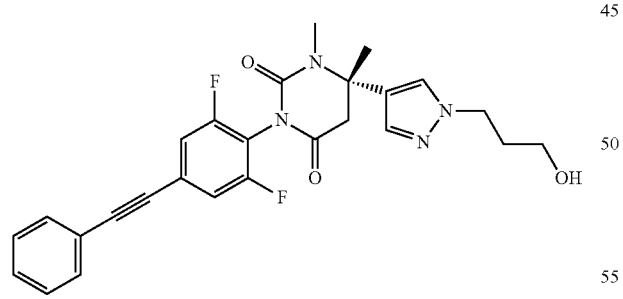

The title compound was obtained as a light yellow oil, MS: m/e=479.2 (M+H$^+$), using chemistry similar to that described in Example 1, step 7 starting from (6S)-3-[2,6-difluoro-4-(2-phenylethynyl)phenyl]-1,6-dimethyl-6-(1H-pyrazol-4-yl)hexahydropyrimidine-2,4-dione (Example 16) and 3-iodopropan-1-ol.

Example 23

(6S)-3-[2,6-Difluoro-4-(2-phenylethynyl)phenyl]-6-[1-(2-hydroxyethyl)pyrazol-4-yl]-1,6-dimethyl-hexahydropyrimidine-2,4-dione

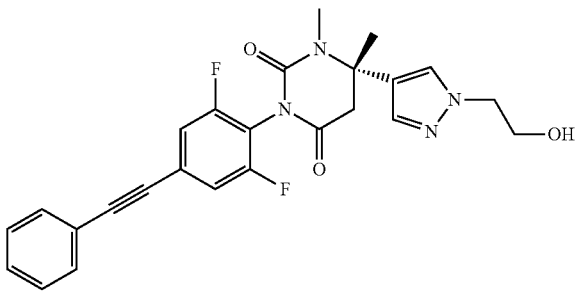 [SMILES: CN1C(=O)N(c2c(F)cc(C#Cc3ccccc3)cc2F)C(=O)C[C@@]1(C)c1cnn(CCO)c1]

The title compound was obtained as a yellow oil, MS: m/e=465.1 (M+H$^+$), using chemistry similar to that described in Example 1, step 7 starting from (6S)-3-[2,6-difluoro-4-(2-phenylethynyl)phenyl]-1,6-dimethyl-6-(1H-pyrazol-4-yl)hexahydropyrimidine-2,4-dione (Example 16) and 2-iodoethanol.

Example 24

(6S)-3-[2,6-Difluoro-4-[2-(3-pyridyl)ethynyl]phenyl]-1,6-dimethyl-6-(1-methylpyrazol-4-yl)hexahydropyrimidine-2,4-dione

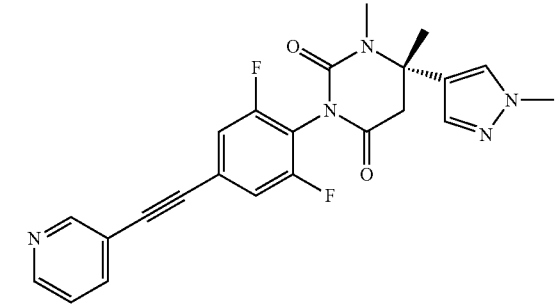 [SMILES: CN1C(=O)N(c2c(F)cc(C#Cc3cccnc3)cc2F)C(=O)C[C@@]1(C)c1cnn(C)c1]

Step 1: (6S)-3-(2,6-Difluoro-4-iodo-phenyl)-1,6-dimethyl-6-(1-methylpyrazol-4-yl)hexahydropyrimidine-2,4-dione The title compound was obtained as a light yellow solid, MS: m/e=461.1 (M+H$^+$), using chemistry similar to that described in Example 1, step 5, 6 and 7 starting from 2,6-difluoro-4-iodoaniline and methyl (3S)-3-amino-3-(1-methylpyrazol-4-yl)butanoate (Example 5, step 1).

Step 2: (6S)-3-[2,6-Difluoro-4-[2-(3-pyridyl)ethynyl]phenyl]-1,6-dimethyl-6-(1-methylpyrazol-4-yl)hexahydropyrimidine-2,4-dione The title compound was obtained as a light yellow solid, MS: m/e=436.2 (M+H$^+$), using chemistry similar to that described in Example 1, step 1 starting from (6S)-3-(2,6- difluoro-4-iodo-phenyl)-1,6-dimethyl-6-(1-methylpyrazol-4-yl)hexahydropyrimidine-2,4-dione (Example 24, step 1) and 3-ethynylpyridine.

Example 25

(6S)-3-[2,6-Difluoro-4-(2-isothiazol-4-ylethynyl)phenyl]-1,6-dimethyl-6-(1-methylpyrazol-4-yl)hexahydropyrimidine-2,4-dione

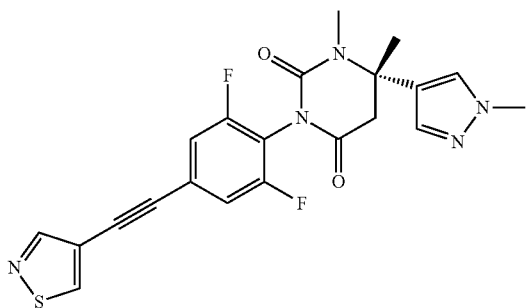 [SMILES: CN1C(=O)N(c2c(F)cc(C#Cc3cnsc3)cc2F)C(=O)C[C@@]1(C)c1cnn(C)c1]

Step 1: 4-((Trimethylsilyl)ethynyl)isothiazole

The title compound was obtained as a yellow oil, MS: m/e=182.1 (M+H$^+$), using chemistry similar to that described in Example 1, step 1 starting from 4-bromoisothiazole and ethynyltrimethylsilane.

Step 2: (6S)-3-[2,6-Difluoro-4-(2-isothiazol-4-ylethynyl)phenyl]-1,6-dimethyl-6-(1-methylpyrazol-4-yl)hexahydropyrimidine-2,4-dione The title compound was obtained as a yellow oil, MS: m/e=442.1 (M+H$^+$), using chemistry similar to that described in Example 1, step 1 starting from (6S)-3-(2,6-difluoro-4-iodo-phenyl)-1,6-dimethyl-6-(1-methylpyrazol-4-yl)hexahydropyrimidine-2,4-dione (Example 24, step 1) and 4-((trimethylsilyl)ethynyl)isothiazole (Example 25, step 1) (cleaved to the corresponding acetylene in situ by addition of 1.5 equiv. of TBAF).

Example 26

(6S)-3-[2,6-Difluoro-4-(2-phenylethynyl)phenyl]-1,6-dimethyl-6-(1-methylpyrazol-3-yl)hexahydropyrimidine-2,4-dione

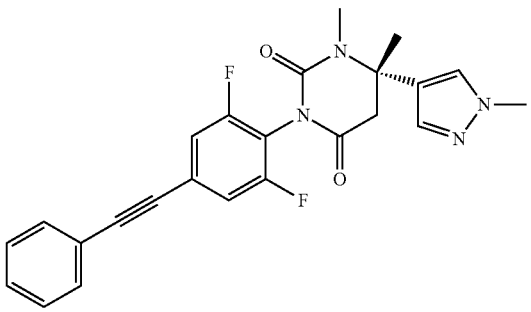 [SMILES: CN1C(=O)N(c2c(F)cc(C#Cc3ccccc3)cc2F)C(=O)C[C@@]1(C)c1cnn(C)c1]

Step 1: Methyl (3S)-3-amino-3-(1-methylpyrazol-3-yl)butanoate

The title compound was obtained as a yellow oil, MS: m/e=198.1 (M+H$^+$), using chemistry similar to that described in Example 1, step 2,3 and 4 starting from 1-(1-methylpyrazol-3-yl)ethanone.

Step 2: (6S)-3-[2,6-Difluoro-4-(2-phenylethynyl)phenyl]-1,6-dimethyl-6-(1-methylpyrazol-3-yl)hexahydropyrimidine-2,4-dione The title compound was obtained as a white solid, MS: m/e=435.1 (M+H$^+$), using chemistry similar to that described in Example 1, step 5, 6 and 7 starting from 2,6-difluoro-4-phenylethynyl-phenylamine (Example 1, step 1) and methyl (3S)-3-amino-3-(1-methylpyrazol-3-yl)butanoate (Example 26, step 1).

Example 27

(6S)-3-[2,6-Difluoro-4-(2-phenylethynyl)phenyl]-6-ethyl-1-methyl-6-(1-methylpyrazol-3-yl)hexahydropyrimidine-2,4-dione

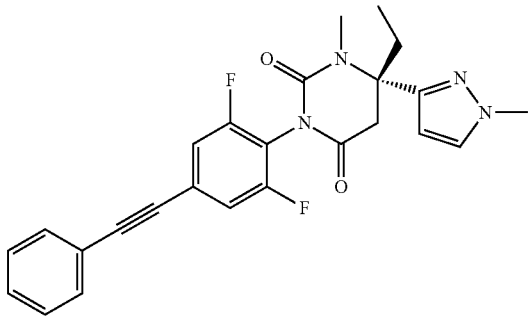 [SMILES: CC[C@@]1(c2ccn(C)n2)CC(=O)N(c2c(F)cc(C#Cc3ccccc3)cc2F)C(=O)N1C]

Step 1: Methyl (3S)-3-amino-3-(1-methylpyrazol-3-yl)pentanoate

The title compound was obtained as a yellow oil, MS: m/e=212.1 (M+H$^+$), using chemistry similar to that described in Example 1, step 2,3 and 4 starting from 1-(1-methylpyrazol-3-yl)propanone.

Step 2: (6S)-3-[2,6-Difluoro-4-(2-phenylethynyl)phenyl]-6-ethyl-1-methyl-6-(1-methylpyrazol-3-yl)hexahydropyrimidine-2,4-dione The title compound was obtained as a yellow solid, MS: m/e=449.2 (M+H$^+$), using chemistry similar to that described in Example 1, step 5, 6 and 7 starting from 2,6-difluoro-4-phenylethynyl-phenylamine (Example 1, step 1) and methyl (3S)-3-amino-3-(1-methylpyrazol-3-yl)pentanoate (Example 27, step 1).

Example 28

(6S)-3-[2,6-Difluoro-4-(2-phenylethynyl)phenyl]-6-(1-ethylpyrazol-3-yl)-1,6-dimethyl-hexahydropyrimidine-2,4-dione

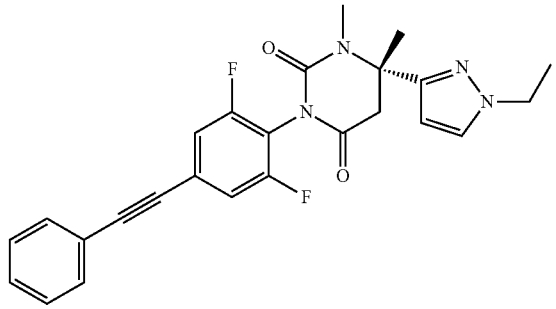 [SMILES: CCn1ccc([C@]2(C)CC(=O)N(c3c(F)cc(C#Cc4ccccc4)cc3F)C(=O)N2C)n1]

The title compound was obtained as a white semi-solid, MS: m/e=449.2 (M+H$^+$), using chemistry similar to that described in Example 1, step 7 starting from (6S)-3-[2,6-difluoro-4-(2-phenylethynyl)phenyl]-1,6-dimethyl-6-(1H-pyrazol-3-yl)hexahydropyrimidine-2,4-dione (Example 10) and iodoethane.

Example 29

(6S)-3-[2,6-Difluoro-4-(2-phenylethynyl)phenyl]-6-(1-isopropylpyrazol-3-yl)-1,6-dimethyl-hexahydropyrimidine-2,4-dione

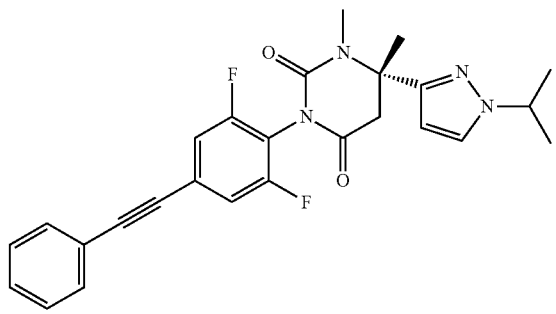 [SMILES: CC(C)n1ccc([C@]2(C)CC(=O)N(c3c(F)cc(C#Cc4ccccc4)cc3F)C(=O)N2C)n1]

The title compound was obtained as a light yellow oil, MS: m/e=463.2 (M+H$^+$), using chemistry similar to that described in Example 1, step 7 starting from (6S)-3-[2,6-difluoro-4-(2-phenylethynyl)phenyl]-1,6-dimethyl-6-(1H-pyrazol-3-yl)hexahydropyrimidine-2,4-dione (Example 10) and 2-iodopropane.

Example 30

(6S)-3-[2,6-Difluoro-4-(2-phenylethynyl)phenyl]-6-[1-(2-methoxyethyl)pyrazol-3-yl]-1,6-dimethyl-hexahydropyrimidine-2,4-dione

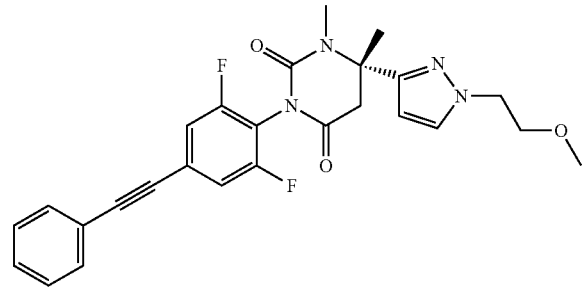 [SMILES: COCCn1ccc([C@]2(C)CC(=O)N(c3c(F)cc(C#Cc4ccccc4)cc3F)C(=O)N2C)n1]

The title compound was obtained as a white semi-solid, MS: m/e=479.2 (M+H$^+$), using chemistry similar to that described in Example 1, step 7 starting from (6S)-3-[2,6-difluoro-4-(2-phenylethynyl)phenyl]-1,6-dimethyl-6-(1H-pyrazol-3-yl)hexahydropyrimidine-2,4-dione (Example 10) and 1-iodo-2-methoxyethane.

Example 31

(6S)-3-[2,6-Difluoro-4-(2-phenylethynyl)phenyl]-6-[1-(3-methoxypropyl)pyrazol-3-yl]-1,6-dimethyl-hexahydropyrimidine-2,4-dione

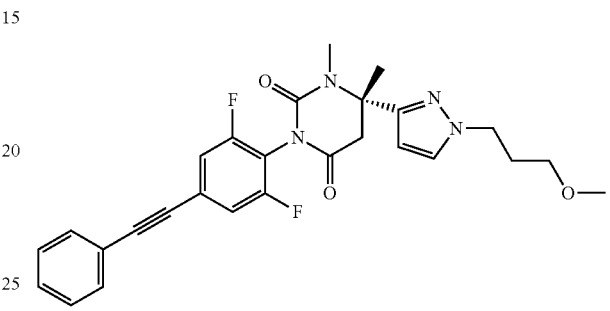

The title compound was obtained as a light yellow oil, MS: m/e=493.2 (M+H$^+$), using chemistry similar to that described in Example 1, step 7 starting from (6S)-3-[2,6-difluoro-4-(2-phenylethynyl)phenyl]-1,6-dimethyl-6-(1H-pyrazol-3-yl)hexahydropyrimidine-2,4-dione (Example 10) and 1-bromo-3-methoxypropane.

Example 32

(6S)-3-[2,6-Difluoro-4-(2-phenylethynyl)phenyl]-1,6-dimethyl-6-(1H-triazol-5-yl)hexahydropyrimidine-2,4-dione

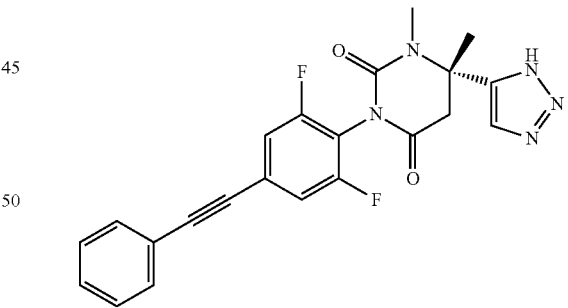

Step 1: 1-(1-((2-(Trimethylsilyl)ethoxy)methyl)-1H-1,2,3-triazol-4-yl)ethanone (2-(Azidomethoxy)ethyl)trimethylsilane (2 g, 11.5 mmol) was dissolved in 40 ml of DMF. But-3-yn-2-one (1.96 g, 28.9 mmol, 2.5 equiv.), triethylamine (8.04 ml, 5.84 g, 57.7 mmol, 5 equiv.) and copper(I) iodide (5.5 g, 28.9 mmol, 2.5 equiv.) were added and the mixture was stirred for 2 hours at room temperature. The reaction mixture was extracted with saturated NaHCO$_3$ solution and ethyl acetate. The aqueous layer was extracted twice with ethyl acetate. The organic layers were washed with water and brine, dried over sodium sulfate and evaporated to dryness. The crude product was purified by flash chromatography on a silica gel column eluting with an ethyl acetate:heptane 0:100 to 50:50 gradient. The desired 1-(1-((2-(trimethylsilyl)ethoxy)methyl)-1H-1,2,3-triazol-4-yl)ethanone (1.3 g, 47% yield) was obtained as a white solid, MS: m/e=242.2 (M+H$^+$).

Step 2: (S)-Methyl 3-amino-3-(1-((2-(trimethylsilyl)ethoxy)methyl)-1H-1,2,3-triazol-4-yl)butanoate The title compound was obtained as a light yellow solid, MS: m/e=315.2 (M+H$^+$), using chemistry similar to that described in Example 1, step 2,3 and 4 starting from 1-(1-((2-(trimethyl silyl)ethoxy)methyl)-1H-1,2,3-triazol-4-yl)ethanone (Example 32, step 1) by stirring the cleavage step with HCl just 10 minutes instead of 1 hour.

Step 3: (S)-3-(2,6-Difluoro-4-(phenylethynyl)phenyl)-1,6-dimethyl-6-(1-((2-(trimethylsilyl)ethoxy)methyl)-1H-1,2,3-triazol-4-yl)dihydropyrimidine-2,4 (1H,3H)-dione The title compound was obtained as a colorless oil, MS: m/e=552.2 (M+H$^+$), using chemistry similar to that described in Example 1, step 5, 6 and 7 starting from 2,6-difluoro-4-phenylethynyl-phenylamine (Example 1, step 1) and (S)-methyl 3-amino-3-(1-((2-(trimethyl silyl)ethoxy)methyl)-1H-1,2,3-triazol-4-yl)butanoate (Example 32, step 2).

Step 4: (6S)-3-[2,6-Difluoro-4-(2-phenylethynyl)phenyl]-1,6-dimethyl-6-(1H-triazol-5-yl)hexahydropyrimidine-2,4-dione The title compound was obtained as a light yellow oil, MS: m/e=422.2 (M+H$^+$), using chemistry similar to that described in Example 1, step 4 starting from (S)-3-(2,6-difluoro-4-(phenylethynyl)phenyl)-1,6-dimethyl-6-(1-((2-(trimethylsilyl)ethoxy)methyl)-1H-1,2,3-triazol-4-yl)dihydropyrimidine-2,4(1H,3H)-dione (Example 32, step 3).

Example 33

(6S)-3-[2,6-Difluoro-4-(2-phenylethynyl)phenyl]-1,6-dimethyl-6-(2-methyltriazol-4-yl)hexahydropyrimidine-2,4-dione

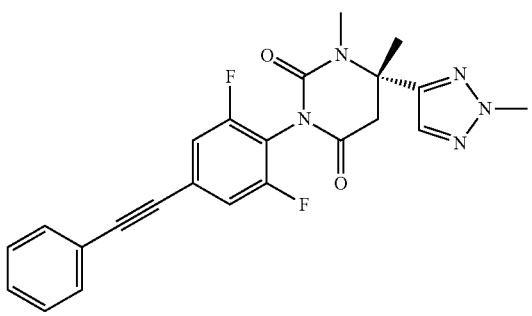 [SMILES: CN1C(=O)N(c2c(F)cc(C#Cc3ccccc3)cc2F)C(=O)C[C@@]1(C)c1cnn(C)n1]

The title compound was obtained as a white solid, MS: m/e=436.2 (M+H$^+$), using chemistry similar to that described in Example 1, step 7 starting from (6S)-3-[2,6-difluoro-4-(2-phenylethynyl)phenyl]-1,6-dimethyl-6-(1H-triazol-5-yl)hexahydropyrimidine-2,4-dione (Example 32, step 4) and iodomethane.

Example 34

(6S)-3-[2,6-Difluoro-4-(2-phenylethynyl)phenyl]-1,6-dimethyl-6-(1-methyltriazol-4-yl)hexahydropyrimidine-2,4-dione

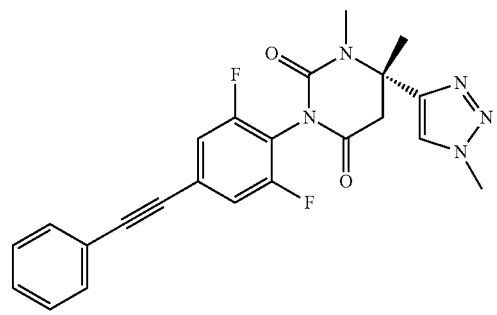 [SMILES: CN1C(=O)N(c2c(F)cc(C#Cc3ccccc3)cc2F)C(=O)C[C@@]1(C)c1cn(C)nn1]

The title compound was obtained as a white solid, MS: m/e=436.2 (M+H$^+$), using chemistry similar to that described in Example 1, step 7 starting from (6S)-3-[2,6-difluoro-4-(2-phenylethynyl)phenyl]-1,6-dimethyl-6-(1H-triazol-5-yl)hexahydropyrimidine-2,4-dione (Example 32, step 4) and iodomethane.

Example 35

(6S)-3-[2,6-Difluoro-4-(2-phenylethynyl)phenyl]-1,6-dimethyl-6-oxazol-5-yl-hexahydropyrimidine-2,4-dione

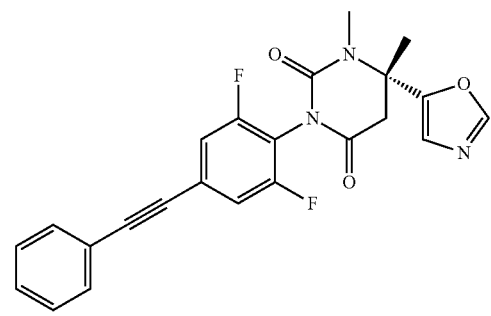

Step 1: (S)-Methyl 3-amino-3-(oxazol-5-yl)butanoate

The title compound was obtained as a light yellow oil, MS: m/e=185.1 (M+H$^+$), using chemistry similar to that described in Example 1, step 2,3 and 4 starting from 1-(oxazol-5-yl)ethanone (CAS 1263378-07-9).

Step 2: (6S)-3-[2,6-Difluoro-4-(2-phenylethynyl)phenyl]-1,6-dimethyl-6-oxazol-5-yl-hexahydropyrimidine-2,4-dione The title compound was obtained as a white solid, MS: m/e=422.1 (M+H$^+$), using chemistry similar to that described in Example 1, step 5, 6 and 7 starting from 2,6-difluoro-4-phenylethynyl-phenylamine (Example 1, step 1) and (S)-methyl 3-amino-3-(oxazol-5-yl)butanoate (Example 35, step 1).

Example 36

(6S)-3-[2,6-Difluoro-4-[2-(3-pyridyl)ethynyl]phenyl]-1,6-dimethyl-6-(1H-pyrazol-4-yl)hexahydropyrimidine-2,4-dione

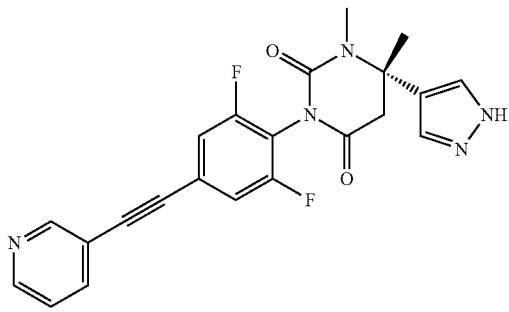 [SMILES: CN1C(=O)N(c2c(F)cc(C#Cc3cccnc3)cc2F)C(=O)C[C@@]1(C)c1cn[nH]c1]

Step 1: (S)-3-(2,6-Difluoro-4-iodophenyl)-1,6-dimethyl-6-(1-((2-(trimethylsilyl)ethoxy)methyl)-1H-pyrazol-4-yl)dihydropyrimidine-2,4(1H,3H)-dione The title compound was obtained as a light brown solid, MS: m/e=577.1 (M+H⁺), using chemistry similar to that described in Example 1, step 5, 6 and 7 starting from 2,6-difluoro-4-iodoaniline and methyl (3S)-3-amino-3-[1-(2-trimethylsilylethoxymethyl)pyrazol-4-yl]butanoate (Example 16, step 2).

Step 2: (S)-3-(2,6-Difluoro-4-iodophenyl)-1,6-dimethyl-6-(1H-pyrazol-4-yl)dihydropyrimidine-2,4(1H,3H)-dione The title compound was obtained as a light yellow oil, MS: m/e=447.0 (M+H⁺), using chemistry similar to that described in Example 1, step 4 starting from (S)-3-(2,6-difluoro-4-iodophenyl)-1,6-dimethyl-6-(1-((2-(trimethylsilyl)ethoxy)methyl)-1H-pyrazol-4-yl)dihydropyrimidine-2,4(1H,3H)-dione (Example 36, step 1).

Step 3: (6S)-3-[2,6-Difluoro-4-[2-(3-pyridyl)ethynyl]phenyl]-1,6-dimethyl-6-(1H-pyrazol-4-yl)hexahydropyrimidine-2,4-dione The title compound was obtained as a white solid, MS: m/e=422.2 (M+H⁺), using chemistry similar to that described in Example 1, step 1 starting from (S)-3-(2,6-difluoro-4-iodophenyl)-1,6-dimethyl-6-(1H-pyrazol-4-yl)dihydropyrimidine-2,4(1H,3H)-dione (Example 36, step 2) and 3-ethynylpyridine.

Example 37

(6S)-3-[2-Chloro-4-(2-phenylethynyl)phenyl]-1,6-dimethyl-6-(1-methylpyrazol-4-yl)hexahydropyrimidine-2,4-dione

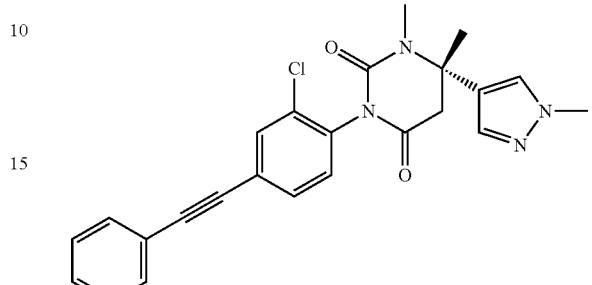

Step 1: (S)-Methyl 3-(3-(2-chloro-4-iodophenyl)ureido)-3-(1H-pyrazol-4-yl)butanoate The title compound isolated as a byproduct was obtained as a light yellow oil, MS: m/e=463.1/465.1 (M+H⁺), using chemistry similar to that described in Example 1, step 5 by using triphosgene in toluene instead of CDI in DMF starting from 2-chloro-4-iodoaniline and methyl (3S)-3-amino-3-[1-(2-trimethylsilylethoxymethyl)pyrazol-4-yl]butanoate (Example 16, step 2).

Step 2: (S)-3-(2-Chloro-4-iodophenyl)-6-methyl-6-(1H-pyrazol-4-yl)dihydropyrimidine-2,4(1H,3H)-dione The title compound was obtained as a colorless oil, MS: m/e=431.0/432.9 (M+H⁺), using chemistry similar to that described in Example 1, step 6 starting from (S)-methyl 3-(3-(2-chloro-4-iodophenyl)ureido)-3-(1H-pyrazol-4-yl)butanoate (Example 37, step 1).

Step 3: (S)-3-(2-Chloro-4-iodophenyl)-1,6-dimethyl-6-(1-methyl-1H-pyrazol-4-yl)dihydropyrimidine-2,4(1H,3H)-dione The title compound was obtained as a colorless oil, MS: m/e=459.1/461.1 (M+H⁺), using chemistry similar to that described in Example 1, step 7 starting from (S)-3-(2-chloro-4-iodophenyl)-6-methyl-6-(1H-pyrazol-4-yl)dihydropyrimidine-2,4(1H,3H)-dione (Example 37, step 2) and iodomethane.

Step 4: (6S)-3-[2-Chloro-4-(2-phenylethynyl)phenyl]-1,6-dimethyl-6-(1-methylpyrazol-4-yl)hexahydropyrimidine-2,4-dione The title compound was obtained as a light yellow foam, MS: m/e=433.1/435.2 (M+H⁺), using chemistry similar to that described in Example 1, step 1 starting from (S)-3-(2-chloro-4-iodophenyl)-1,6-dimethyl-6-(1-methyl-1H-pyrazol-4-yl)dihydropyrimidine-2,4(1H,3H)-dione (Example 37, step 3) and phenylacetylene.

Example 38

(6S)-3-[2,6-Difluoro-4-(2-phenylethynyl)phenyl]-6-isothiazol-3-yl-1,6-dimethyl-hexahydropyrimidine-2,4-dione

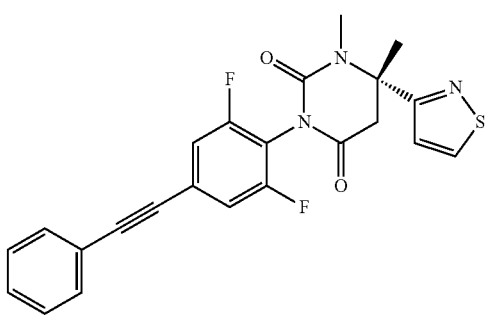 [SMILES: CN1C(=O)N(c2c(F)cc(C#Cc3ccccc3)cc2F)C(=O)C[C@@]1(C)c1ccsn1]

Step 1: (S)-Methyl 3-amino-3-(isothiazol-3-yl)butanoate

The title compound was obtained as a yellow oil, MS: m/e=201.1 (M+H⁺), using chemistry similar to that described in Example 1, step 2,3 and 4 starting from 1-(isothiazol-3-yl)ethanone (CAS 88511-35-7).

Step 2: (6S)-3-[2,6-Difluoro-4-(2-phenylethynyl)phenyl]-6-isothiazol-3-yl-1,6-dimethyl-hexahydropyrimidine-2,4-dione The title compound was obtained as a light yellow oil, MS: m/e=438.2 (M+H⁺), using chemistry similar to that described in Example 1, step 5, 6 and 7 starting from 2,6-difluoro-4-phenylethynyl-phenylamine (Example 1, step 1) and (S)-methyl 3-amino-3-(isothiazol-3-yl)butanoate (Example 38, step 1).

Example 39

(6S)-3-[2,6-Difluoro-4-(2-phenylethynyl)phenyl]-1,6-dimethyl-6-(2-methylthiazol-5-yl)hexahydropyrimidine-2,4-dione

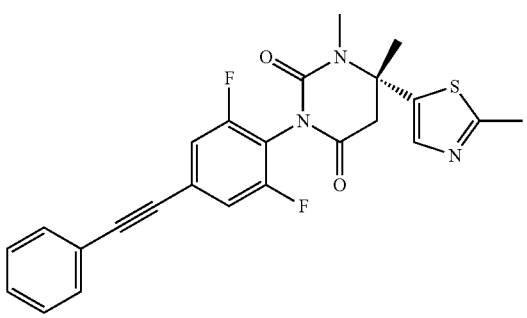

Step 1: (S)-Methyl 3-amino-3-(2-methylthiazol-5-yl)butanoate

The title compound was obtained as a yellow oil, MS: m/e=216.0 (M+H⁺), using chemistry similar to that described in Example 1, step 2,3 and 4 starting from 1-(2-methylthiazol-5-yl)ethanone (CAS 43040-02-4).

Step 2: (6S)-3-[2,6-Difluoro-4-(2-phenylethynyl)phenyl]-1,6-dimethyl-6-(2-methylthiazol-5-yl)hexahydropyrimidine-2,4-dione The title compound was obtained as a light yellow oil, MS: m/e=452.1 (M+H⁺), using chemistry similar to that described in Example 1, step 5, 6 and 7 starting from 2,6-difluoro-4-phenylethynyl-phenylamine (Example 1, step 1) and (S)-methyl 3-amino-3-(2-methylthiazol-5-yl)butanoate (Example 39, step 1).

Example 40

(6S)-3-[2,6-Difluoro-4-(2-phenylethynyl)phenyl]-6-isoxazol-3-yl-1,6-dimethyl-hexahydropyrimidine-2,4-dione

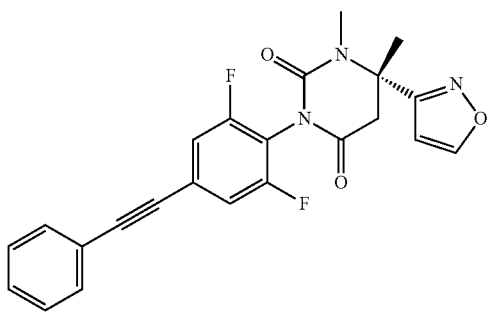 [SMILES: CN1C(=O)N(c2c(F)cc(C#Cc3ccccc3)cc2F)C(=O)C[C@@]1(C)c1ccon1]

Step 1: (S)-Methyl 3-amino-3-(isoxazol-3-yl)butanoate

The title compound was obtained as a yellow liquid, MS: m/e=185.1 (M+H⁺), using chemistry similar to that described in Example 1, step 2,3 and 4 starting from 1-(isoxazol-3-yl)ethanone (CAS 88511-37-9).

Step 2: (6S)-3-[2,6-Difluoro-4-(2-phenylethynyl)phenyl]-6-isoxazol-3-yl-1,6-dimethyl-hexahydropyrimidine-2,4-dione The title compound was obtained as a white solid, MS: m/e=422.1 (M+H⁺), using chemistry similar to that described in Example 1, step 5, 6 and 7 starting from 2,6-difluoro-4-phenylethynyl-phenylamine (Example 1, step 1) and (S)-methyl 3-amino-3-(isoxazol-3-yl)butanoate (Example 40, step 1).

Example 41

(6S)-3-[2,6-Difluoro-4-(2-phenylethynyl)phenyl]-6-isoxazol-5-yl-1,6-dimethyl-hexahydropyrimidine-2,4-dione

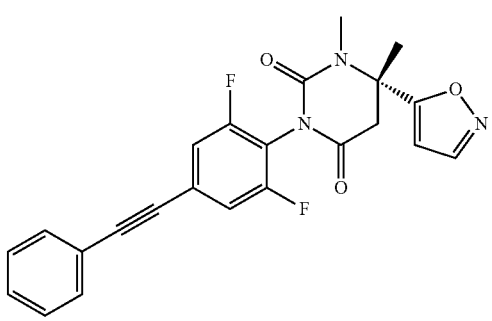 [SMILES: CN1C(=O)N(c2c(F)cc(C#Cc3ccccc3)cc2F)C(=O)C[C@@]1(C)c1ccno1]

Step 1: (S)-Methyl 3-amino-3-(isoxazol-3-yl)butanoate

The title compound was obtained as a brown oil, MS: m/e=185.1 (M+H$^+$), using chemistry similar to that described in Example 1, step 2,3 and 4 starting from 1-(isoxazol-5-yl)ethanone (CAS 88511-38-0).

Step 2: (6S)-3-[2,6-Difluoro-4-(2-phenylethynyl)phenyl]-6-isoxazol-5-yl-1,6-dimethyl-hexahydropyrimidine-2,4-dione The title compound was obtained as a light yellow oil, MS: m/e=422.2 (M+H$^+$), using chemistry similar to that described in Example 1, step 5, 6 and 7 starting from 2,6-difluoro-4-phenylethynyl-phenylamine (Example 1, step 1) and (S)-methyl 3-amino-3-(isoxazol-5-yl)butanoate (Example 41, step 1).

Example 42

(6S)-3-[2,6-Difluoro-4-(2-phenylethynyl)phenyl]-1,6-dimethyl-6-thiazol-5-yl-hexahydropyrimidine-2,4-dione

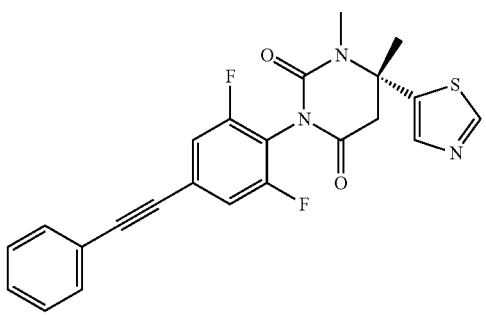

Step 1: (S)-Methyl 3-amino-3-(thiazol-5-yl)butanoate

The title compound was obtained as a yellow oil, MS: m/e=201.0 (M+H$^+$), using chemistry similar to that described in Example 1, step 2,3 and 4 starting from 1-(thiazol-5-yl)ethanone (CAS 91516-28-8).

Step 2: (6S)-3-[2,6-Difluoro-4-(2-phenylethynyl)phenyl]-1,6-dimethyl-6-thiazol-5-yl-hexahydropyrimidine-2,4-dione The title compound was obtained as a colorless oil, MS: m/e=438.1 (M+H$^+$), using chemistry similar to that described in Example 1, step 5, 6 and 7 starting from 2,6-difluoro-4-phenylethynyl-phenylamine (Example 1, step 1) and (S)-methyl 3-amino-3-(thiazol-5-yl)butanoate (Example 42, step 1).

Example 43

(6S)-3-[2,6-Difluoro-4-(2-phenylethynyl)phenyl]-6-isothiazol-5-yl-1,6-dimethyl-hexahydropyrimidine-2,4-dione

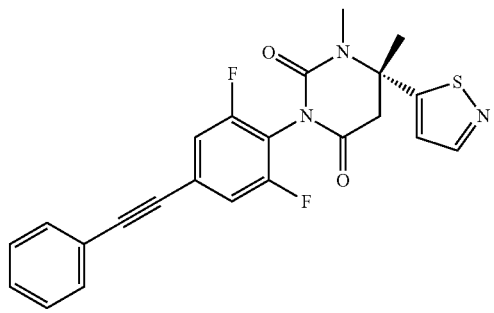

Step 1: (S)-Methyl 3-amino-3-(isothiazol-5-yl)butanoate

The title compound was obtained as a yellow oil, MS: m/e=201.1 (M+H$^+$), using chemistry similar to that described in Example 1, step 2,3 and 4 starting from 1-(isothiazol-5-yl)ethanone (CAS 3684-00-2).

Step 2: (6S)-3-[2,6-Difluoro-4-(2-phenylethynyl)phenyl]-6-isothiazol-5-yl-1,6-dimethyl-hexahydropyrimidine-2,4-dione The title compound was obtained as a light yellow oil, MS: m/e=438.1 (M+H$^+$), using chemistry similar to that described in Example 1, step 5, 6 and 7 starting from 2,6-difluoro-4-phenylethynyl-phenylamine (Example 1, step 1) and (S)-methyl 3-amino-3-(isothiazol-5-yl)butanoate (Example 43, step 1).

Example 44

(6S)-3-[2-Chloro-6-fluoro-4-(2-phenylethynyl)phenyl]-1,6-dimethyl-6-(1-methylpyrazol-4-yl)hexahydropyrimidine-2,4-dione

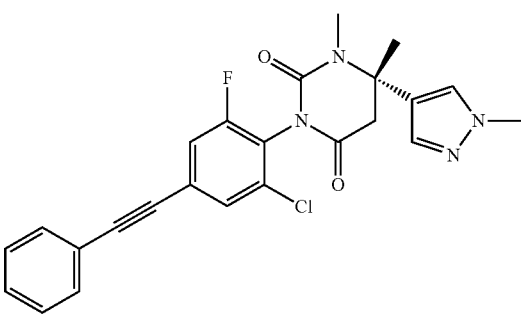

Step 1: (S)-Methyl 3-(3-(4-bromo-2-chloro-6-fluorophenyl)ureido)-3-(1H-pyrazol-4-yl)butanoate 4-Bromo-2-chloro-6-fluorobenzoic acid (194 mg, 0.766 mmol, 1.2 equiv.) was dissolved in toluene (4.0 ml) and Et₃N (194 mg, 0.267 ml, 1.91 mmol, 3 equiv.) and DPPA (211 mg, 0.165 ml, 0.766 mmol, 1.2 equiv.) were added at room temperature. The mixture was stirred for 30 minutes at 100° C. To the mixture methyl (3S)-3-amino-3-[1-(2-trimethylsilylethoxymethyl)pyrazol-4-yl]butanoate (Example 16, step 2) (200 mg, 0.638 mmol) was added at room temperature and stirred for 1 hour. The reaction mixture was loaded directly onto a silica gel column. The crude product was purified by flash chromatography eluting with an ethyl acetate:heptane 10:90 to 100:0 gradient. The desired (S)-methyl 3-(3-(4-bromo-2-chloro-6-fluorophenyl)ureido)-3-(1H-pyrazol-4-yl)butanoate (85 mg, 31% yield) formed as a byproduct in this reaction, was obtained as a colorless oil, MS: m/e=433.0/435.1 (M+H⁺).

Step 2: (S)-3-(4-Bromo-2-chloro-6-fluorophenyl)-6-methyl-6-(1H-pyrazol-4-yl)dihydropyrimidine-2,4(1H,3H)-dione The title compound was obtained as a white solid, MS: m/e=401.0/402.9 (M+H⁺), using chemistry similar to that described in Example 1, step 6 starting from (S)-methyl 3-(3-(4-bromo-2-chloro-6-fluorophenyl)ureido)-3-(1H-pyrazol-4-yl)butanoate (Example 44, step 1).

Step 3: (S)-3-(4-Bromo-2-chloro-6-fluorophenyl)-1,6-dimethyl-6-(1-methyl-1H-pyrazol-4-yl)dihydropyrimidine-2,4(1H,3H)-dione The title compound was obtained as a colorless oil, MS: m/e=429.0/431.1 (M+H⁺), using chemistry similar to that described in Example 1, step 7 starting from (S)-3-(4-bromo-2-chloro-6-fluorophenyl)-6-methyl-6-(1H-pyrazol-4-yl)dihydropyrimidine-2,4(1H,3H)-dione (Example 44, step 2) and iodomethane.

Step 4: (6S)-3-[2-Chloro-6-fluoro-4-(2-phenylethynyl)phenyl]-1,6-dimethyl-6-(1-methylpyrazol-4-yl)hexahydropyrimidine-2,4-dione The title compound was obtained as a light yellow oil, MS: m/e=451.2/453.1 (M+H⁺), using chemistry similar to that described in Example 1, step 1 starting from (S)-3-(4-bromo-2-chloro-6-fluorophenyl)-1,6-dimethyl-6-(1-methyl-1H-pyrazol-4-yl)dihydropyrimidine-2,4(1H,3H)-dione (Example 44, step 3) and phenylacetylene.

Example 45

(6S)-3-[2,6-Difluoro-4-(2-phenylethynyl)phenyl]-6-ethyl-1-methyl-6-(1H-pyrazol-4-yl)hexahydropyrimidine-2,4-dione

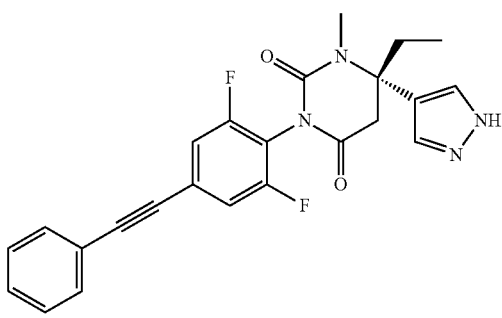

Step 1: Ethyl 1-((2-(trimethylsilyl)ethoxy)methyl)-1H-pyrazole-4-carboxylate

The title compound was obtained as a yellow oil, MS: m/e=271.2 (M+H⁺), using chemistry similar to that described in Example 10, step 1 starting from ethyl 1H-pyrazole-4-carboxylate and (2-(chloromethoxy)ethyl)trimethylsilane.

Step 2: 1-((2-(Trimethylsilyl)ethoxy)methyl)-1H-pyrazole-4-carboxylic acid

Ethyl 1-((2-(trimethylsilyl)ethoxy)methyl)-1H-pyrazole-4-carboxylate (Example 45, step 1) (36.3 g, 107 mmol) was dissolved in 300 ml of THF and 100 ml of MeOH. 4N NaOH (80.5 ml, 322 mmol, 3 equiv.) was added at room temperature and the mixture was stirred for 4 hours. The organic solvent were evaporated off and the aqueous mixture acidified to pH 2 with 2N HCl. The mixture was extracted twice with ethyl acetate. The organic layers were washed with brine, dried over sodium sulfate and evaporated to dryness. The desired 1-((2-(trimethylsilyl)ethoxy)methyl)-1H-pyrazole-4-carboxylic acid (29.5 g, quant. yield) was obtained as a light yellow solid, MS: m/e=243.1 (M+H⁺).

Step 3: N-Methoxy-N-methyl-1-((2-(trimethylsilyl)ethoxy)methyl)-1H-pyrazole-4-carboxamide 1-((2-(Trimethylsilyl)ethoxy)methyl)-1H-pyrazole-4-carboxylic acid (Example 45, step 2) (22.5 g, 92.8 mmol) was suspended in 200 ml of THF and N,O-dimethylhydroxylamine hydrochloride (13.6 g, 139 mmol, 1.5 equiv.) and N,N-diisopropylethylamine (48.6 ml, 36 g, 279 mmol, 3 equiv.) were added at room temperature. Propylphosphonic anhydride solution (50% in ethyl acetate) (66.3 ml, 111 mmol, 1.2 equiv.) was added drop wise at room temperature under ice cooling. The mixture was stirred for 2.5 hours at room temperature. The reaction mixture was extracted with saturated NaHCO₃ solution and two times with ethyl acetate. The organic layers were washed with brine, dried over sodium sulfate and evaporated to dryness. The crude product was used directly in the next step. The desired N-methoxy-N-methyl-1-((2-(trimethylsilyl)ethoxy)methyl)-1H-pyrazole-4-carboxamide (20 g, 76% yield) was obtained as an orange oil, MS: m/e=386.2 (M+H⁺).

Step 4: 1-(1-((2-(Trimethylsilyl)ethoxy)methyl)-1H-pyrazol-4-yl)propan-1-one

N-methoxy-N-methyl-1-((2-(trimethylsilyl)ethoxy)methyl)-1H-pyrazole-4-carboxamide (Example 45, step 3) (1 g, 3.5 mmol) was dissolved in 10 ml of THF and ethylmagnesium bromide (3M in diethylether) (1.75 ml, 5.26 mmol, 1.5 equiv.) was added drop wise at 0-5° C. The mixture was stirred for 4 hours at 0-5° C. The reaction mixture was extracted with saturated NH₄Cl solution and two times with ethyl acetate. The organic layers were washed with water, brine, dried over sodium sulfate and evaporated to dryness. The crude product was used directly in the next step. The desired 1-(1-((2-(trimethylsilyl)ethoxy)methyl)-1H-pyrazol-4-yl)propan-1-one (870 mg, 98% yield) was obtained as a yellow oil, MS: m/e=255.2 (M+H⁺).

Step 5: (S)-Methyl 3-amino-3-(1-((2-(trimethyl silyl)ethoxy)methyl)-1H-pyrazol-4-yl)pentanoate The title compound was obtained as a light yellow oil, MS: m/e=328.2 (M+H⁺), using chemistry similar to that described in Example 1, step 2,3 and 4 starting from 1-(1-((2-(trimethyl silyl)ethoxy)methyl)-1H-pyrazol-4-yl)propan-1-one (Example 45, step 4) by stirring the cleavage step with HCl just 15 minutes instead of 1 hour.

Step 6: (S)-3-(2,6-Difluoro-4-(phenylethynyl)phenyl)-6-ethyl-1-methyl-6-(1-((2-(trimethylsilyl)ethoxy)methyl)-1H-pyrazol-4-yl)dihydropyrimidine-2,4(1H,3H)-dione The title compound was obtained as a light yellow oil, MS: m/e=565.1 (M+H⁺), using chemistry similar to that described in Example 1, step 5, 6 and 7 starting from 2,6-difluoro-4-phenylethynyl-phenylamine (Example 1, step 1) and (S)-methyl 3-amino-3-(1-((2-(trimethyl silyl)ethoxy)methyl)-1H-pyrazol-4-yl)pentanoate (Example 45, step 5).

Step 7: (6S)-3-[2,6-Difluoro-4-(2-phenylethynyl)phenyl]-6-ethyl-1-methyl-6-(1H-pyrazol-4-yl)hexahydropyrimidine-2,4-dione The title compound was obtained as a light yellow foam, MS: m/e=435.2 (M+H⁺), using chemistry similar to that described in Example 1, step 4 starting from (S)-3-(2,6-difluoro-4-(phenylethynyl)phenyl)-6-ethyl-1-methyl-6-(1-((2-(trimethyl silyl)ethoxy)methyl)-1H-pyrazol-4-yl)dihydropyrimidine-2,4(1H,3H)-dione (Example 45, step 6).

Example 46

(S)-3-(2,6-Difluoro-4-(phenylethynyl)phenyl)-6-(1-(2-hydroxyethyl)-1H-pyrazol-3-yl)-1,6-dimethyldihydropyrimidine-2,4(1H,3H)-dione

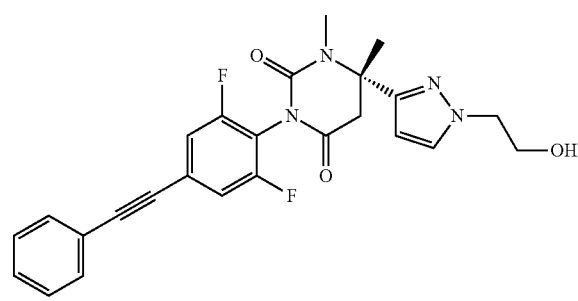 [SMILES: CN1C(=O)N(c2c(F)cc(C#Cc3ccccc3)cc2F)C(=O)C[C@@]1(C)c1ccn(CCO)n1]

The title compound was obtained as a light yellow oil, MS: m/e=465.2 (M+H⁺), using chemistry similar to that described in Example 1, step 7 starting from (6S)-3-[2,6-difluoro-4-(2-phenylethynyl)phenyl]-1,6-dimethyl-6-(1H-pyrazol-3-yl)hexahydropyrimidine-2,4-dione (Example 10) and 2-iodoethanol.

Example 47

(6S)-3-[2,6-Difluoro-4-[2-(3-fluorophenyl)ethynyl]phenyl]-1,6-dimethyl-6-(1-methylpyrazol-4-yl)hexahydropyrimidine-2,4-dione

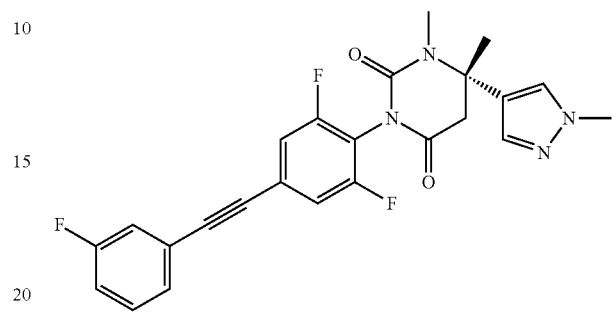

The title compound was obtained as a light yellow oil, MS: m/e=453.2 (M+H⁺), using chemistry similar to that described in Example 1, step 1 starting from (6S)-3-(2,6-difluoro-4-iodo-phenyl)-1,6-dimethyl-6-(1-methylpyrazol-4-yl)hexahydropyrimidine-2,4-dione (Example 24, step 1) and 1-ethynyl-3-fluorobenzene.

Example 48

(6S)-3-[4-[2-(2,5-Difluorophenyl)ethynyl]-2,6-difluoro-phenyl]-1,6-dimethyl-6-(1-methylpyrazol-4-yl)hexahydropyrimidine-2,4-dione

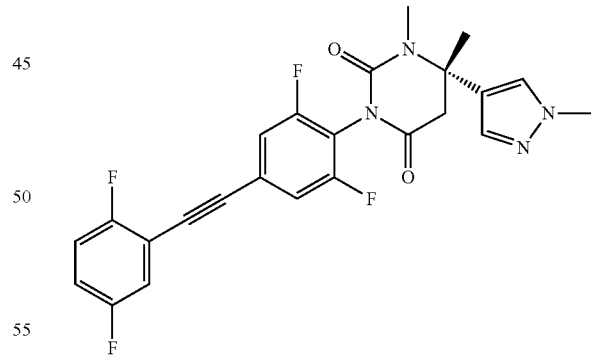

The title compound was obtained as a white foam, MS: m/e=471.2 (M+H⁺), using chemistry similar to that described in Example 1, step 1 starting from (6S)-3-(2,6-difluoro-4-iodo-phenyl)-1,6-dimethyl-6-(1-methylpyrazol-4-yl)hexahydropyrimidine-2,4-dione (Example 24, step 1) and 2-ethynyl-1,4-difluorobenzene.

Example 49

(6S)-3-[2,6-Difluoro-4-[2-(4-fluorophenyl)ethynyl]phenyl]-1,6-dimethyl-6-(1-methylpyrazol-4-yl)hexahydropyrimidine-2,4-dione

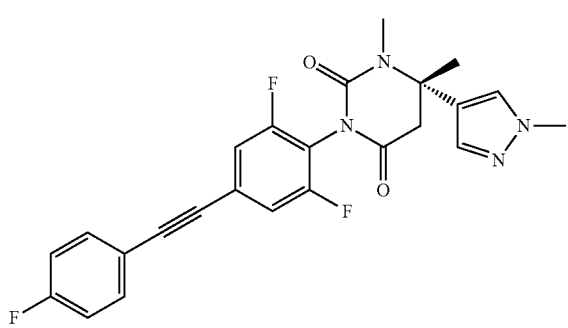 [SMILES: CN1C(=O)N(c2c(F)cc(C#Cc3ccc(F)cc3)cc2F)C(=O)C[C@@]1(C)c1cnn(C)c1]

The title compound was obtained as a light yellow oil, MS: m/e=453.2 (M+H$^+$), using chemistry similar to that described in Example 1, step 1 starting from (6S)-3-(2,6-difluoro-4-iodo-phenyl)-1,6-dimethyl-6-(1-methylpyrazol-4-yl)hexahydropyrimidine-2,4-dione (Example 24, step 1) and 2-ethynyl-1,4-difluorobenzene.

Example 50

(6S)-3-[2,6-Difluoro-4-[2-(2-fluorophenyl)ethynyl]phenyl]-1,6-dimethyl-6-(1-methylpyrazol-4-yl)hexahydropyrimidine-2,4-dione

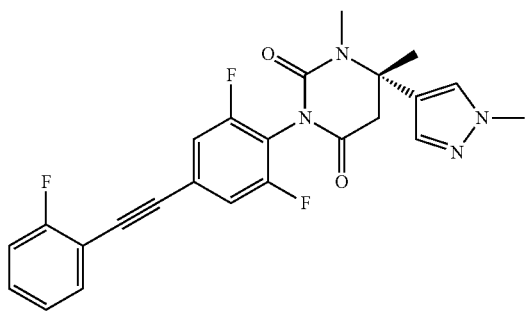 [SMILES: CN1C(=O)N(c2c(F)cc(C#Cc3ccccc3F)cc2F)C(=O)C[C@@]1(C)c1cnn(C)c1]

The title compound was obtained as a light yellow oil, MS: m/e=453.2 (M+H$^+$), using chemistry similar to that described in Example 1, step 1 starting from (6S)-3-(2,6-difluoro-4-iodo-phenyl)-1,6-dimethyl-6-(1-methylpyrazol-4-yl)hexahydropyrimidine-2,4-dione (Example 24, step 1) and 1-ethynyl-2-fluorobenzene.

Example 51

(6S)-3-[2,6-Difluoro-4-[2-(3-pyridyl)ethynyl]phenyl]-6-ethyl-1-methyl-6-(1H-pyrazol-4-yl)hexahydropyrimidine-2,4-dione

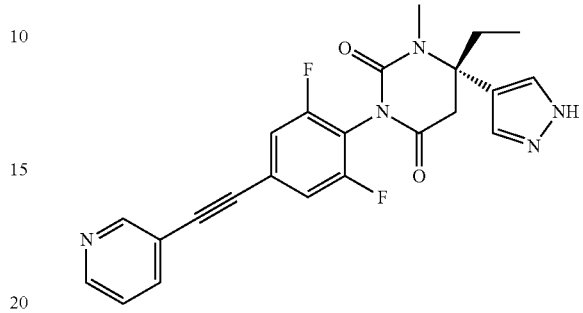

Step 1: Phenyl (2,6-difluoro-4-iodophenyl)carbamate 2,6-Difluoro-4-iodoaniline (10 g, 39.2 mmol) was dissolved in 100 ml of THF. Hunig's base (7.53 ml, 5.58 g, 43.1 mmol, 1.1 equiv.) and phenyl chloroformate (5.4 ml, 6.75 g, 43.1 mmol, 1.1 equiv.) were added at room temperature and the mixture was stirred for 16 hours at 60° C. The reaction mixture was extracted with saturated NaHCO$_3$ solution and two times with ethyl acetate. The organic layers were washed with water and brine, dried over sodium sulfate and evaporated to dryness. The residue was stirred in heptane, filtered off and dried for 2 hours at 50° C. and <10 mbar. The desired phenyl (2,6-difluoro-4-iodophenyl)carbamate (10.3 g, 70% yield) was obtained as a light brown solid, MS: m/e=376.0 (M+H$^+$).

Step 2: (S)-Methyl 3-(3-(2,6-difluoro-4-iodophenyl)ureido)-3-(1-((2-(trimethylsilyl)ethoxy)methyl)-1H-pyrazol-4-yl)pentanoate Phenyl (2,6-difluoro-4-iodophenyl)carbamate (Example 51, step 1) (1.82 g, 4.86 mmol, 1.5 equiv) was dissolved in 20 ml of THF. Potassium carbonate (1.34 g, 9.73 mmol, 3 equiv.) and (S)-methyl 3-amino-3-(1-((2-(trimethylsilyl)ethoxy)methyl)-1H-pyrazol-4-yl)pentanoate (Example 45, step 5) (1.18 g, 3.24 mmol) were added at room temperature and the mixture was stirred for 16 hours at 60° C. The reaction mixture was extracted with saturated NaHCO$_3$ solution and two times with ethyl acetate. The organic layers were washed with water, brine, dried over sodium sulfate and evaporated to dryness. The crude product was purified by flash chromatography on a silica gel column eluting with an ethyl acetate:heptane 0:100 to 100:0 gradient. The desired (S)-methyl 3-(3-(2,6-difluoro-4-iodophenyl)ureido)-3-(1-((2-(trimethylsilyl)ethoxy)methyl)-1H-pyrazol-4-yl)pentanoate (300 mg, 15% yield) was obtained as a light brown oil, MS: m/e=609.1 (M+H$^+$).

Step 3: (S)-3-(2,6-Difluoro-4-iodophenyl)-6-ethyl-1-methyl-6-(1-((2-(trimethylsilyl)ethoxy)methyl)-1H-pyrazol-4-yl)dihydropyrimidine-2,4(1H,3H)-dione The title compound was obtained as a colorless oil, MS: m/e=591.2 (M+H$^+$), using chemistry similar to that described in Example 1, step 6 and 7 starting from (S)-methyl 3-(3-(2,6-difluoro-4-iodophenyl)ureido)-3-(1-((2-(trimethylsilyl)ethoxy)methyl)-1H-pyrazol-4-yl)pentanoate (Example 51, step 2).

Step 4: (S)-3-(2,6-Difluoro-4-iodophenyl)-6-ethyl-1-methyl-6-(1H-pyrazol-4-yl)dihydropyrimidine-2,4(1H,3H)-dione The title compound was obtained as a colorless oil, MS: m/e=461.0 (M+H⁺), using chemistry similar to that described in Example 1, step 4 starting from (S)-3-(2,6-difluoro-4-iodophenyl)-6-ethyl-1-methyl-6-(1-((2-(trimethyl silyl)ethoxy)methyl)-1H-pyrazol-4-yl)dihydropyrimidine-2,4(1H,3H)-dione (Example 51, step 3).

Step 5: (6S)-3-[2,6-Difluoro-4-[2-(3-pyridyl)ethynyl]phenyl]-6-ethyl-1-methyl-6-(1H-pyrazol-4-yl)hexahydropyrimidine-2,4-dione The title compound was obtained as a white foam, MS: m/e=436.2 (M+H⁺), using chemistry similar to that described in Example 1, step 1 starting from (S)-3-(2,6-difluoro-4-iodophenyl)-6-ethyl-1-methyl-6-(1H-pyrazol-4-yl)dihydropyrimidine-2,4(1H,3H)-dione (Example 51, step 4) and 3-ethynylpyridine.

Example 52

(6S)-6-(1-Cyclopropylpyrazol-4-yl)-3-[2,6-difluoro-4-(2-phenylethynyl)phenyl]-1,6-dimethyl-hexahydropyrimidine-2,4-dione

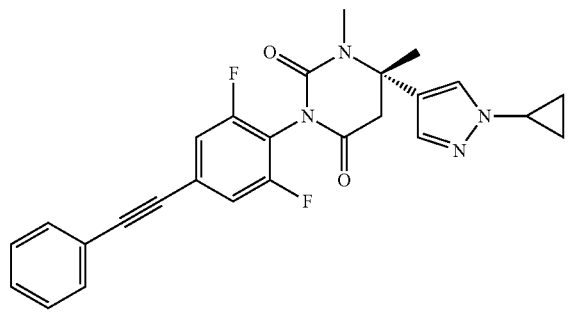 [SMILES: CN1C(=O)N(c2c(F)cc(C#Cc3ccccc3)cc2F)C(=O)C[C@@]1(C)c1cnn(C2CC2)c1]

(6S)-3-[2,6-difluoro-4-(2-phenylethynyl)phenyl]-1,6-dimethyl-6-(1H-pyrazol-4-yl)hexahydropyrimidine-2,4-dione (Example 16) (85 mg, 0.2 mmol) was dissolved in 2 ml of 1,2-dichloroethane. Cyclopropylboronic acid (35 mg, 0.4 mmol, 2 equiv.), sodium carbonate (54 mg, 0.5 mmol, 2.5 equiv.), 2,2'-bipyridine (38 mg, 0.24 mmol, 1.2 equiv.) and copper (II) acetate (44 mg, 0.24 mmol, 1.2 equiv.) were added at room temperature and the mixture was stirred for 2 hours at 70° C. The reaction mixture was extracted with saturated NaHCO₃ solution and two times with DCM. The organic layers were purified directly by flash chromatography on a silica gel column eluting with an ethyl acetate: heptane 0:100 to 100:0 gradient. The desired (6S)-6-(1-cyclopropylpyrazol-4-yl)-3-[2,6-difluoro-4-(2-phenylethynyl)phenyl]-1,6-dimethyl-hexahydropyrimidine-2,4-dione (31 mg, 33% yield) was obtained as a white solid, MS: m/e=461.3 (M+H⁺).

Example 53

(6S)-3-[2,6-Difluoro-4-[2-(2-fluorophenyl)ethynyl]phenyl]-1,6-dimethyl-6-(1H-pyrazol-4-yl)hexahydropyrimidine-2,4-dione

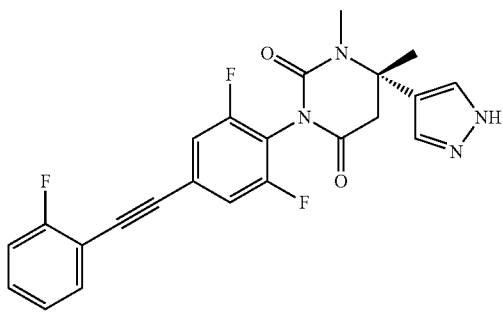 [SMILES: CN1C(=O)N(c2c(F)cc(C#Cc3ccccc3F)cc2F)C(=O)C[C@@]1(C)c1cn[nH]c1]

The title compound was obtained as a white solid, MS: m/e=439.2 (M+H⁺), using chemistry similar to that described in Example 1, step 1 starting from (S)-3-(2,6-difluoro-4-iodophenyl)-1,6-dimethyl-6-(1H-pyrazol-4-yl)dihydropyrimidine-2,4(1H,3H)-dione (Example 36, step 2) and 1-ethynyl-2-fluorobenzene.

Example 54

(6S)-3-[2,6-Difluoro-4-[2-(4-fluorophenyl)ethynyl]phenyl]-1,6-dimethyl-6-(1H-pyrazol-4-yl)hexahydropyrimidine-2,4-dione

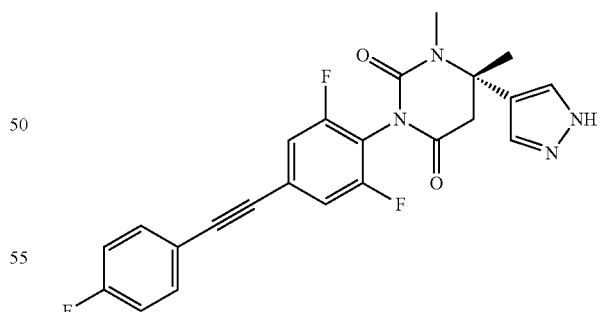

The title compound was obtained as a white solid, MS: m/e=439.2 (M+H⁺), using chemistry similar to that described in Example 1, step 1 starting from (S)-3-(2,6-difluoro-4-iodophenyl)-1,6-dimethyl-6-(1H-pyrazol-4-yl)dihydropyrimidine-2,4(1H,3H)-dione (Example 36, step 2) and 1-ethynyl-4-fluorobenzene.

Example 55

(6S)-3-[4-[2-(2,3-Difluorophenyl)ethynyl]-2,6-difluoro-phenyl]-1,6-dimethyl-6-(1H-pyrazol-4-yl)hexahydropyrimidine-2,4-dione

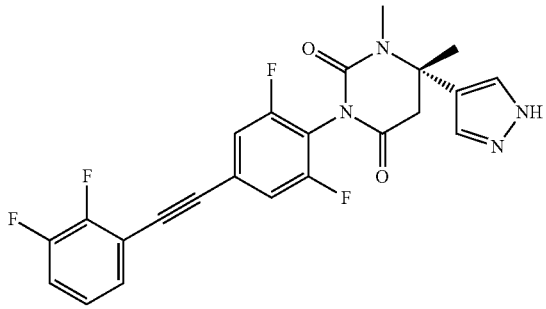 [SMILES: CN1C(=O)N(c2c(F)cc(C#Cc3cccc(F)c3F)cc2F)C(=O)C[C@@]1(C)c1cn[nH]c1]

Step 1: (S)-3-(4-((2,3-Difluorophenyl)ethynyl)-2,6-difluorophenyl)-1,6-dimethyl-6-(1-((2-(trimethylsilyl)ethoxy)methyl)-1H-pyrazol-4-yl)dihydropyrimidine-2,4(1H,3H)-dione The title compound was obtained as a light yellow solid, MS: m/e=587.3 (M+H⁺), using chemistry similar to that described in Example 1, step 1 starting from (S)-3-(2,6-difluoro-4-iodophenyl)-1,6-dimethyl-6-(1-((2-(trimethyl silyl)ethoxy)methyl)-1H-pyrazol-4-yl)dihydropyrimidine-2,4(1H,3H)-dione (Example 36, step 1) and 1-ethynyl-2,3-difluorobenzene.

Step 2: (6S)-3-[4-[2-(2,3-Difluorophenyl)ethynyl]-2,6-difluoro-phenyl]-1,6-dimethyl-6-(1H-pyrazol-4-yl)hexahydropyrimidine-2,4-dione The title compound was obtained as a white solid, MS: m/e=457.2 (M+H⁺), using chemistry similar to that described in Example 1, step 4 starting from (S)-3-(4-((2,3-difluorophenyl)ethynyl)-2,6-difluorophenyl)-1,6-dimethyl-6-(1-((2-(trimethyl silyl)ethoxy)methyl)-1H-pyrazol-4-yl)dihydropyrimidine-2,4(1H,3H)-dione (Example 55, step 1).

Example 56

(6S)-3-[4-[2-(2,4-Difluorophenyl)ethynyl]-2,6-difluoro-phenyl]-1,6-dimethyl-6-(1H-pyrazol-4-yl)hexahydropyrimidine-2,4-dione

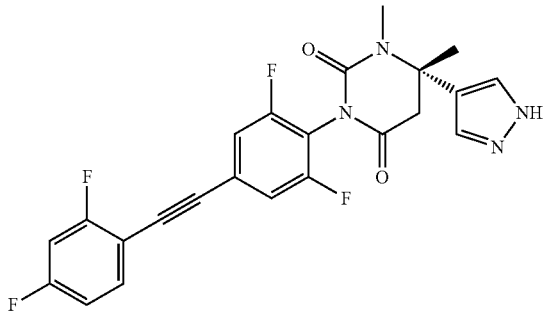 [SMILES: CN1C(=O)N(c2c(F)cc(C#Cc3ccc(F)cc3F)cc2F)C(=O)C[C@@]1(C)c1cn[nH]c1]

Step 1: (S)-3-(4-((2,4-difluorophenyl)ethynyl)-2,6-difluorophenyl)-1,6-dimethyl-6-(1-((2-(trimethylsilyl)ethoxy)methyl)-1H-pyrazol-4-yl)dihydropyrimidine-2,4(1H,3H)-dione The title compound was obtained as a yellow oil, MS: m/e=587.3 (M+H⁺), using chemistry similar to that described in Example 1, step 1 starting from (S)-3-(2,6-difluoro-4-iodophenyl)-1,6-dimethyl-6-(1-((2-(trimethyl silyl)ethoxy)methyl)-1H-pyrazol-4-yl)dihydropyrimidine-2,4(1H,3H)-dione (Example 36, step 1) and 1-ethynyl-2,4-difluorobenzene.

Step 2: (6S)-3-[4-[2-(2,4-Difluorophenyl)ethynyl]-2,6-difluoro-phenyl]-1,6-dimethyl-6-(1H-pyrazol-4-yl)hexahydropyrimidine-2,4-dione The title compound was obtained as a white solid, MS: m/e=457.3 (M+H⁺), using chemistry similar to that described in Example 1, step 4 starting from (S)-3-(4-((2,4-difluorophenyl)ethynyl)-2,6-difluorophenyl)-1,6-dimethyl-6-(1-((2-(trimethyl silyl)ethoxy)methyl)-1H-pyrazol-4-yl)dihydropyrimidine-2,4(1H,3H)-dione (Example 56, step 1).

Example 57

(6S)-3-[4-[2-(2,3-Difluorophenyl)ethynyl]-2,6-difluoro-phenyl]-1,6-dimethyl-6-(1-methylpyrazol-4-yl)hexahydropyrimidine-2,4-dione

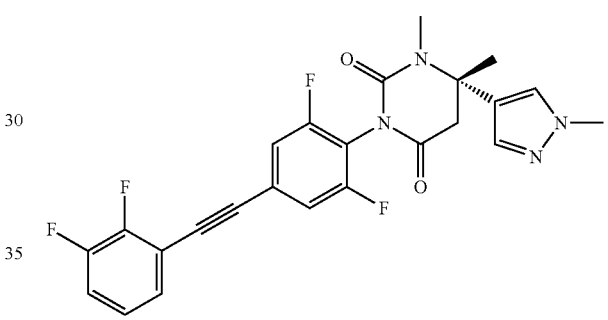

The title compound was obtained as a light yellow oil, MS: m/e=471.3 (M+H⁺), using chemistry similar to that described in Example 1, step 7 starting from (6S)-3-[4-[2-(2,3-difluorophenyl)ethynyl]-2,6-difluoro-phenyl]-1,6-dimethyl-6-(1H-pyrazol-4-yl)hexahydropyrimidine-2,4-dione (Example 55, step 2) and iodomethane.

Example 58

(6S)-3-[4-[2-(2,4-Difluorophenyl)ethynyl]-2,6-difluoro-phenyl]-1,6-dimethyl-6-(1-methylpyrazol-4-yl)hexahydropyrimidine-2,4-dione

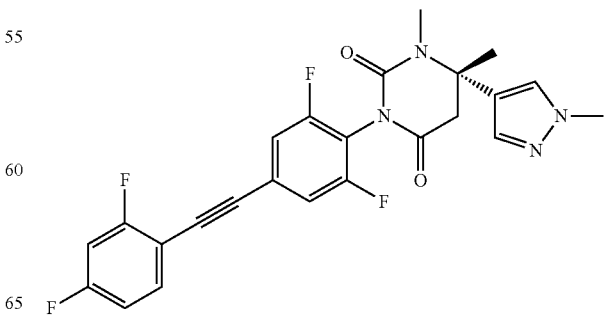

The title compound was obtained as a light yellow oil, MS: m/e=471.3 (M+H⁺), using chemistry similar to that described in Example 1, step 7 starting from (6S)-3-[4-[2-(2,4-difluorophenyl)ethynyl]-2,6-difluoro-phenyl]-1,6-dimethyl-6-(1H-pyrazol-4-yl)hexahydropyrimidine-2,4-dione (Example 56, step 2) and iodomethane.

Example 59

(6S)-3-[2,6-Difluoro-4-[2-(3-fluorophenyl)ethynyl]phenyl]-1,6-dimethyl-6-(1H-pyrazol-4-yl)hexahydropyrimidine-2,4-dione

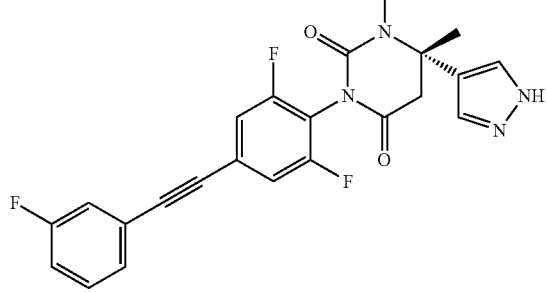

Step 1: (S)-3-(2,6-Difluoro-4-((3-fluorophenyl)ethynyl)phenyl)-1,6-dimethyl-6-(1-((2-(trimethylsilyl)ethoxy)methyl)-1H-pyrazol-4-yl)dihydropyrimidine-2,4(1H,3H)-dione The title compound was obtained as a light yellow oil, MS: m/e=569.3 (M+H⁺), using chemistry similar to that described in Example 1, step 1 starting from (S)-3-(2,6-difluoro-4-iodophenyl)-1,6-dimethyl-6-(1-((2-(trimethylsilyl)ethoxy)methyl)-1H-pyrazol-4-yl)dihydropyrimidine-2,4(1H,3H)-dione (Example 36, step 1) and 1-ethynyl-3-fluorobenzene.

Step 2: (6S)-3-[2,6-Difluoro-4-[2-(3-fluorophenyl)ethynyl]phenyl]-1,6-dimethyl-6-(1H-pyrazol-4-yl)hexahydropyrimidine-2,4-dione The title compound was obtained as a white foam, MS: m/e=439.2 (M+H⁺), using chemistry similar to that described in Example 1, step 4 starting from (S)-3-(2,6-difluoro-4-((3-fluorophenyl)ethynyl)phenyl)-1,6-dimethyl-6-(1-((2-(trimethylsilyl)ethoxy)methyl)-1H-pyrazol-4-yl)dihydropyrimidine-2,4(1H,3H)-dione (Example 59, step 1).

Example 60

(6S)-3-[2,6-Difluoro-4-(2-phenylethynyl)phenyl]-6-[1-(2-hydroxy-2-methyl-propyl)pyrazol-4-yl]-1,6-dimethyl-hexahydropyrimidine-2,4-dione

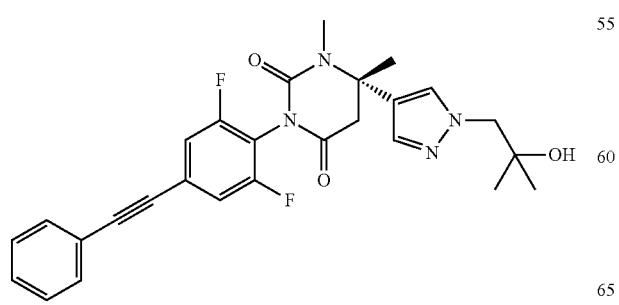

The title compound was obtained as a white solid, MS: m/e=493.3 (M+H⁺), using chemistry similar to that described in Example 1, step 7 starting from (6S)-3-[2,6-difluoro-4-(2-phenylethynyl)phenyl]-1,6-dimethyl-6-(1H-pyrazol-4-yl)hexahydropyrimidine-2,4-dione (Example 16) and 1-iodo-2-methylpropan-2-ol.

Example 61

(6S)-3-[2,6-Difluoro-4-(2-phenylethynyl)phenyl]-1,6-dimethyl-6-[1-(oxetan-3-ylmethyl)pyrazol-4-yl]hexahydropyrimidine-2,4-dione

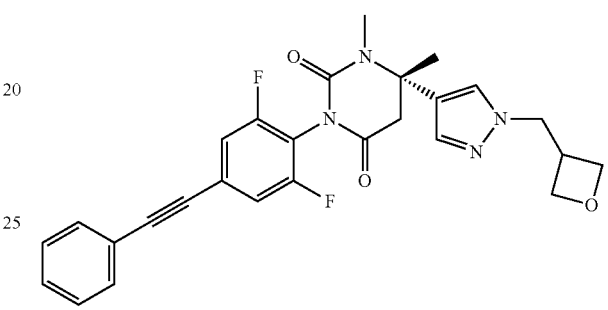

The title compound was obtained as a yellow oil, MS: m/e=491.3 (M+H⁺), using chemistry similar to that described in Example 1, step 7 starting from (6S)-3-[2,6-difluoro-4-(2-phenylethynyl)phenyl]-1,6-dimethyl-6-(1H-pyrazol-4-yl)hexahydropyrimidine-2,4-dione (Example 16) and 3-(bromomethyl)oxetane.

Example 62

(6S)-3-[2,6-Difluoro-4-(2-phenylethynyl)phenyl]-1,6-dimethyl-6-[1-[(3RS)-tetrahydrofuran-3-yl]pyrazol-4-yl]hexahydropyrimidine-2,4-dione

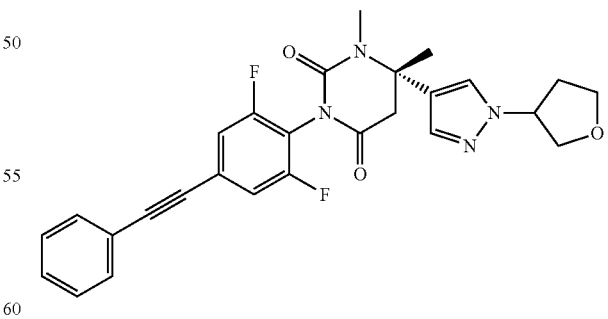

The title compound was obtained as a light yellow oil, MS: m/e=491.4 (M+H⁺), using chemistry similar to that described in Example 1, step 7 starting from (6S)-3-[2,6-difluoro-4-(2-phenylethynyl)phenyl]-1,6-dimethyl-6-(1H-pyrazol-4-yl)hexahydropyrimidine-2,4-dione (Example 16) and (RS)-3-bromotetrahydrofuran.

Example 63

(6S)-3-[2,6-Difluoro-4-(2-phenylethynyl)phenyl]-6-[1-(2-hydroxy-2-methyl-propyl)pyrazol-3-yl]-1,6-dimethyl-hexahydropyrimidine-2,4-dione

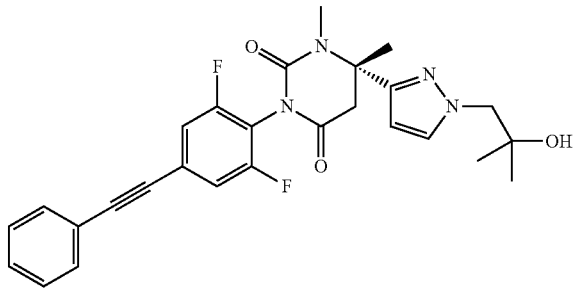 [SMILES: CN1C(=O)N(c2c(F)cc(C#Cc3ccccc3)cc2F)C(=O)C[C@@]1(C)c1ccn(CC(C)(C)O)n1]

The title compound was obtained as a yellow gum, MS: m/e=493.4 (M+H$^+$), using chemistry similar to that described in Example 1, step 7 starting from (6S)-3-[2,6-difluoro-4-(2-phenylethynyl)phenyl]-1,6-dimethyl-6-(1H-pyrazol-3-yl)hexahydropyrimidine-2,4-dione (Example 10) and 1-iodo-2-methylpropan-2-ol.

Example 64

(6S)-3-[2,6-Difluoro-4-(2-phenylethynyl)phenyl]-1,6-dimethyl-6-[1-[(3RS)-tetrahydrofuran-3-yl]pyrazol-3-yl]hexahydropyrimidine-2,4-dione

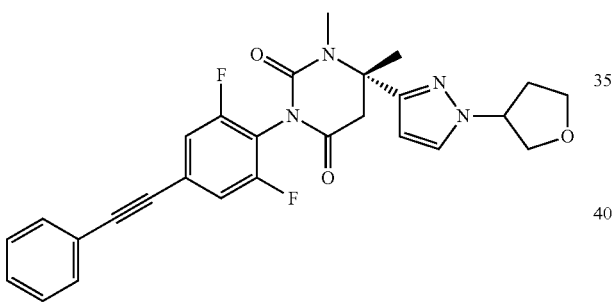

The title compound was obtained as a colorless gum, MS: m/e=491.4 (M+H$^+$), using chemistry similar to that described in Example 1, step 7 starting from (6S)-3-[2,6-difluoro-4-(2-phenylethynyl)phenyl]-1,6-dimethyl-6-(1H-pyrazol-3-yl)hexahydropyrimidine-2,4-dione (Example 10) and (RS)-3-iodotetrahydrofuran.

The invention claimed is:

1. A compound of formula I

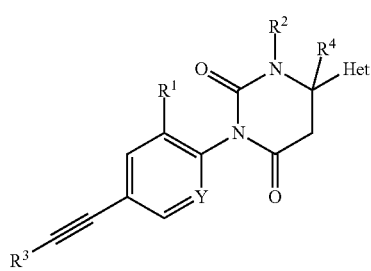

wherein
Y is C—R$^{1'}$;
R$^{1'}$ is hydrogen, F or Cl;
R$^1$ is F or Cl;
R$^2$ is hydrogen or lower alkyl;
R$^3$ is phenyl, pyridinyl or isothiazolyl, wherein the N atom in the pyridinyl group may be in different positions, optionally substituted by one or two halogen atoms;
R$^4$ is hydrogen or lower alkyl;
Het is a 5-membered heteroaryl group, containing two or three heteroatoms, selected from N, O or S, optionally substituted by lower alkyl, cycloalkyl, lower alkoxyalkyl, heterocycloalkyl, wherein the hetero-atom is O, or lower alkyl substituted by hydroxy, or is a bicyclic heteroaromatic ring, containing two or three N-heteroatoms selected from the groups

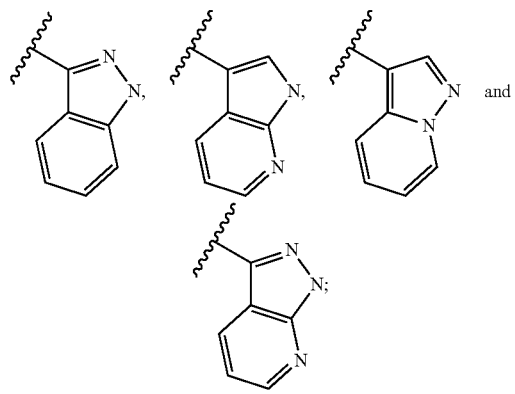

or a pharmaceutically acceptable salt or acid addition salt, a racemic mixture, or its corresponding enantiomer and/or optical isomer and/or stereoisomer thereof.

2. A compound of formula IA according to claim 1,

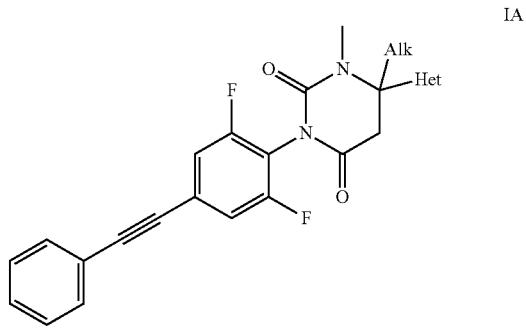

wherein
Het is a 5-membered heteroaryl group, containing two or three heteroatoms, selected from N, O or S, optionally substituted by lower alkyl, cycloalkyl, lower alkoxyalkyl, heterocycloalkyl, wherein the hetero-atom is O, or lower alkyl substituted by hydroxy;
Alk is lower alkyl;
or a pharmaceutically acceptable salt or acid addition salt, a racemic mixture, or its corresponding enantiomer and/or optical isomer and/or stereoisomer thereof.

3. A compound of formula IA according to claim 2, selected from the group consisting of (6S)-3-[2,6-Difluoro-4-(2-phenylethynyl)phenyl]-1,6-dimethyl-6-thiazol-2-yl-hexahydropyrimidine-2,4-dione
(6S)-3-[2,6-Difluoro-4-(2-phenylethynyl)phenyl]-1,6-dimethyl-6-(1-methylimidazol-4-yl)hexahydropyrimidine-2,4-dione
(6RS)-3-[2,6-Difluoro-4-(2-phenylethynyl)phenyl]-1,6-dimethyl-6-(2-methylthiazol-4-yl)hexahydropyrimidine-2,4-dione
(6S)-3-[2,6-Difluoro-4-(2-phenylethynyl)phenyl]-1,6-dimethyl-6-(2-methyl-1,2,4-triazol-3-yl)hexahydropyrimidine-2,4-dione
(6S)-3-[2,6-Difluoro-4-(2-phenylethynyl)phenyl]-6-methyl-6-(1-methylpyrazol-4-yl)hexahydropyrimidine-2,4-dione
(6S)-3-[2,6-Difluoro-4-(2-phenylethynyl)phenyl]-1,6-dimethyl-6-(1-methylpyrazol-4-yl)hexahydropyrimidine-2,4-dione
(6S)-3-[2,6-Difluoro-4-(2-phenylethynyl)phenyl]-1,6-dimethyl-6-(2-methylpyrazol-3-yl)hexahydropyrimidine-2,4-dione
(6S)-3-[2,6-Difluoro-4-(2-phenylethynyl)phenyl]-1,6-dimethyl-6-(1H-pyrazol-3-yl)hexahydropyrimidine-2,4-dione
(6S)-3-[2,6-Difluoro-4-(2-phenylethynyl)phenyl]-1,6-dimethyl-6-(3-methylimidazol-4-yl)hexahydropyrimidine-2,4-dione
(6S)-3-[2,6-Difluoro-4-(2-phenylethynyl)phenyl]-1-ethyl-6-methyl-6-(1-methylpyrazol-4-yl)hexahydropyrimidine-2,4-dione
(6S)-3-[2,6-Difluoro-4-(2-phenylethynyl)phenyl]-6-(1-ethylpyrazol-4-yl)-1,6-dimethyl-hexahydropyrimidine-2,4-dione
(6S)-3-[2,6-Difluoro-4-(2-phenylethynyl)phenyl]-6-isothiazol-4-yl-1,6-dimethyl-hexahydropyrimidine-2,4-dione
(6S)-3-[2,6-Difluoro-4-(2-phenylethynyl)phenyl]-1,6-dimethyl-6-(1H-pyrazol-4-yl)hexahydropyrimidine-2,4-dione
(6S)-3-[2,6-Difluoro-4-(2-phenylethynyl)phenyl]-6-ethyl-1-methyl-6-(1-methylpyrazol-4-yl)hexahydropyrimidine-2,4-dione
(6S)-3-[2,6-Difluoro-4-(2-phenylethynyl)phenyl]-6-(1-isopropylpyrazol-4-yl)-1,6-dimethyl-hexahydropyrimidine-2,4-dione
(6S)-3-[2,6-Difluoro-4-(2-phenylethynyl)phenyl]-6-[1-(2-methoxyethyl)pyrazol-4-yl]-1,6-dimethyl-hexahydropyrimidine-2,4-dione
(6S)-3-[2,6-Difluoro-4-(2-phenylethynyl)phenyl]-6-[1-(3-methoxypropyl)pyrazol-4-yl]-1,6-dimethyl-hexahydropyrimidine-2,4-dione
(6S)-3-[2,6-Difluoro-4-(2-phenylethynyl)phenyl]-6-[1-(3-hydroxypropyl)pyrazol-4-yl]-1,6-dimethyl-hexahydropyrimidine-2,4-dione
(6S)-3-[2,6-Difluoro-4-(2-phenylethynyl)phenyl]-6-[1-(2-hydroxyethyl)pyrazol-4-yl]-1,6-dimethyl-hexahydropyrimidine-2,4-dione
(6S)-3-[2,6-Difluoro-4-(2-phenylethynyl)phenyl]-1,6-dimethyl-6-(1-methylpyrazol-3-yl)hexahydropyrimidine-2,4-dione
(6S)-3-[2,6-Difluoro-4-(2-phenylethynyl)phenyl]-6-ethyl-1-methyl-6-(1-methylpyrazol-3-yl)hexahydropyrimidine-2,4-dione
(6S)-3-[2,6-Difluoro-4-(2-phenylethynyl)phenyl]-6-(1-ethylpyrazol-3-yl)-1,6-dimethyl-hexahydropyrimidine-2,4-dione
(6S)-3-[2,6-Difluoro-4-(2-phenylethynyl)phenyl]-6-(1-isopropylpyrazol-3-yl)-1,6-dimethyl-hexahydropyrimidine-2,4-dione
(6S)-3-[2,6-Difluoro-4-(2-phenylethynyl)phenyl]-6-[1-(2-methoxyethyl)pyrazol-3-yl]-1,6-dimethyl-hexahydropyrimidine-2,4-dione
(6S)-3-[2,6-Difluoro-4-(2-phenylethynyl)phenyl]-6-[1-(3-methoxypropyl)pyrazol-3-yl]-1,6-dimethyl-hexahydropyrimidine-2,4-dione
(6S)-3-[2,6-Difluoro-4-(2-phenylethynyl)phenyl]-1,6-dimethyl-6-(1H-triazol-5-yl)hexahydropyrimidine-2,4-dione
(6S)-3-[2,6-Difluoro-4-(2-phenylethynyl)phenyl]-1,6-dimethyl-6-(2-methyltriazol-4-yl)hexahydropyrimidine-2,4-dione
(6S)-3-[2,6-Difluoro-4-(2-phenylethynyl)phenyl]-1,6-dimethyl-6-(1-methyltriazol-4-yl)hexahydropyrimidine-2,4-dione
(6S)-3-[2,6-Difluoro-4-(2-phenylethynyl)phenyl]-1,6-dimethyl-6-oxazol-5-yl-hexahydropyrimidine-2,4-dione
(6S)-3-[2,6-Difluoro-4-(2-phenylethynyl)phenyl]-6-isothiazol-3-yl-1,6-dimethyl-hexahydropyrimidine-2,4-dione
(6S)-3-[2,6-Difluoro-4-(2-phenylethynyl)phenyl]-1,6-dimethyl-6-(2-methylthiazol-5-yl)hexahydropyrimidine-2,4-dione
(6S)-3-[2,6-Difluoro-4-(2-phenylethynyl)phenyl]-6-isoxazol-3-yl-1,6-dimethyl-hexahydropyrimidine-2,4-dione
(6S)-3-[2,6-Difluoro-4-(2-phenylethynyl)phenyl]-6-isoxazol-5-yl-1,6-dimethyl-hexahydropyrimidine-2,4-dione
(6S)-3-[2,6-Difluoro-4-(2-phenylethynyl)phenyl]-1,6-dimethyl-6-thiazol-5-yl-hexahydropyrimidine-2,4-dione
(6S)-3-[2,6-Difluoro-4-(2-phenylethynyl)phenyl]-6-isothiazol-5-yl-1,6-dimethyl-hexahydropyrimidine-2,4-dione
(6S)-3-[6-Difluoro-4-(2-phenylethynyl)phenyl]-6-ethyl-1-methyl-6-(1H-pyrazol-4-yl)hexahydropyrimidine-2,4-dione
(S)-3-(2,6-Difluoro-4-(phenylethynyl)phenyl)-6-(1-(2-hydroxyethyl)-1H-pyrazol-3-yl)-1,6-dimethyldihydropyrimidine-2,4(1H,3H)-dione
(6S)-6-(1-Cyclopropylpyrazol-4-yl)-3-[2,6-difluoro-4-(2-phenylethynyl)phenyl]-1,6-dimethyl-hexahydropyrimidine-2,4-dione
(6S)-3-[2,6-Difluoro-4-(2-phenylethynyl)phenyl]-6-[1-(2-hydroxy-2-methyl-propyl)pyrazol-4-yl]-1,6-dimethyl-hexahydropyrimidine-2,4-dione
(6S)-3-[2,6-Difluoro-4-(2-phenylethynyl)phenyl]-1,6-dimethyl-6-[1-(oxetan-3-ylmethyl)pyrazol-4-yl]hexahydropyrimidine-2,4-dione
(6S)-3-[2,6-Difluoro-4-(2-phenylethynyl)phenyl]-1,6-dimethyl-6-[1-[(3RS)-tetrahydrofuran-3-yl]pyrazol-4-yl]hexahydropyrimidine-2,4-dione
(6S)-3-[2,6-Difluoro-4-(2-phenylethynyl)phenyl]-6-[1-(2-hydroxy-2-methyl-propyl)pyrazol-3-yl]-1,6-dimethyl-hexahydropyrimidine-2,4-dione and
(6S)-3-[2,6-Difluoro-4-(2-phenylethynyl)phenyl]-1,6-dimethyl-6-[1-[(3RS)-tetrahydrofuran-3-yl]pyrazol-3-yl]hexahydropyrimidine-2,4-dione or a pharmaceutically acceptable salt or acid addition salt, a racemic mixture, or its corresponding enantiomer and/or optical isomer and/or stereoisomer thereof.

4. A compound of formula D3 according to claim 1

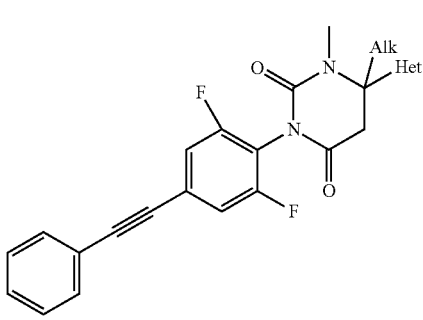

IB wherein

Het is a bicyclic heteroaromatic ring, containing two or three N-heteroatoms, selected from the groups

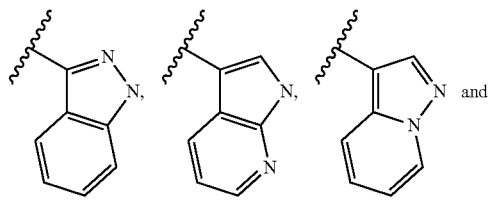

and

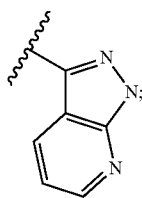

Alk is lower alkyl;

or a pharmaceutically acceptable salt or acid addition salt, a racemic mixture, or its corresponding enantiomer and/or optical isomer and/or stereoisomer thereof.

5. A compound of formula D3 according to claim 4, selected from the group consisting of (6S)-3-[2,6-Difluoro-4-(2-phenylethynyl)phenyl]-1,6-dimethyl-6-(1-methylindazol-3-yl)hexahydropyrimidine-2,4-dione (6S)-3-[2,6-Difluoro-4-(2-phenylethynyl)phenyl]-1,6-dimethyl-6-(1-methylpyrrolo[2,3-b]pyridin-3-yl)hexahydropyrimidine-2,4-dione (6S)-3-[2,6-Difluoro-4-(2-phenylethynyl)phenyl]-1,6-dimethyl-6-pyrazolo[1,5-a]pyridin-3-yl-hexahydropyrimidine-2,4-dione and (6S)-3-[2,6-Difluoro-4-(2-phenylethynyl)phenyl]-1,6-dimethyl-6-(1-methylpyrazolo[3,4-b]pyridin-3-yl)hexahydropyrimidine-2,4-dione or a pharmaceutically acceptable salt or acid addition salt, a racemic mixture, or its corresponding enantiomer and/or optical isomer and/or stereoisomer thereof.

6. A compound of formula IC according to claim 1

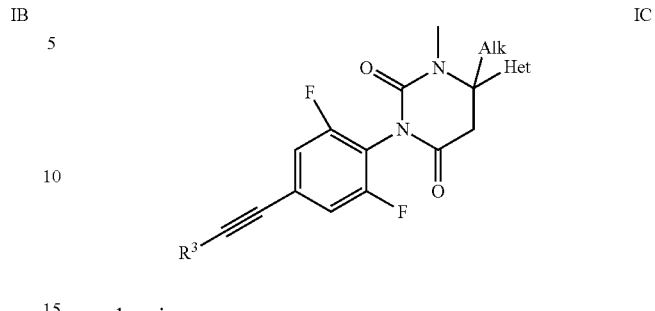

IC wherein $R^3$ is phenyl, pyridinyl or isothiazolyl, wherein the N atom in the pyridinyl group may be in different positions, and wherein phenyl is substituted by one or two halogen atoms;

Het is a 5-membered heteroaryl group, containing two or three heteroatoms, selected from N, O or S, optionally substituted by lower alkyl, cycloalkyl, lower alkoxyalkyl, heterocycloalkyl, wherein the hetero-atom is O, or lower alkyl substituted by hydroxy;

Alk is lower alkyl;

or a pharmaceutically acceptable salt or acid addition salt, a racemic mixture, or its corresponding enantiomer and/or optical isomer and/or stereoisomer thereof.

7. A compound of formula IC according to claim 6, selected from the group consisting of (6S)-3-[2,6-Difluoro-4-[2-(3-pyridyl)ethynyl]phenyl]-1,6-dimethyl-6-(1-methylpyrazol-4-yl)hexahydropyrimidine-2,4-dione (6S)-3-[2,6-Difluoro-4-(2-isothiazol-4-ylethynyl)phenyl]-1,6-dimethyl-6-(1-methylpyrazol-4-yl)hexahydropyrimidine-2,4-dione (6S)-3-[2,6-Difluoro-4-[2-(3-pyridyl)ethynyl]phenyl]-1,6-dimethyl-6-(1H-pyrazol-4-yl)hexahydropyrimidine-2,4-dione (6S)-3-[2,6-Difluoro-4-[2-(3-fluorophenyl)ethynyl]phenyl]-1,6-dimethyl-6-(1-methylpyrazol-4-yl)hexahydropyrimidine-2,4-dione (6S)-3-[4-[2-(2,5-Difluorophenyl)ethynyl]-2,6-difluorophenyl]-1,6-dimethyl-6-(1-methylpyrazol-4-yl)hexahydropyrimidine-2,4-dione (6S)-3-[2,6-Difluoro-4-[2-(4-fluorophenyl)ethynyl]phenyl]-1,6-dimethyl-6-(1-methylpyrazol-4-yl)hexahydropyrimidine-2,4-dione (6S)-3-[2,6-Difluoro-4-[2-(2-fluorophenyl)ethynyl]phenyl]-1,6-dimethyl-6-(1-methylpyrazol-4-yl)hexahydropyrimidine-2,4-dione (6S)-3-[2,6-Difluoro-4-[2-(3-pyridyl)ethynyl]phenyl]-6-ethyl-1-methyl-6-(1H-pyrazol-4-yl)hexahydropyrimidine-2,4-dione (6S)-3-[2,6-Difluoro-4-[2-(2-fluorophenyl)ethynyl]phenyl]-1,6-dimethyl-6-(1H-pyrazol-4-yl)hexahydropyrimidine-2,4-dione (6S)-3-[2,6-Difluoro-4-[2-(4-fluorophenyl)ethynyl]phenyl]-1,6-dimethyl-6-(1H-pyrazol-4-yl)hexahydropyrimidine-2,4-dione (6S)-3-[4-[2-(2,3-Difluorophenyl)ethynyl]-2,6-difluorophenyl]-1,6-dimethyl-6-(1H-pyrazol-4-yl)hexahydropyrimidine-2,4-dione (6S)-3-[4-[2-(2,4-Difluorophenyl)ethynyl]-2,6-difluorophenyl]-1,6-dimethyl-6-(1H-pyrazol-4-yl)hexahydropyrimidine-2,4-dione (6S)-3-[4-[2-(2,3-Difluorophenyl)ethynyl]-2,6-difluorophenyl]-1,6-dimethyl-6-(1-methylpyrazol-4-yl)hexahydropyrimidine-2,4-dione (6S)-3-[4[2-(2,4-Difluorophenyl)ethynyl]-2,6-difluorophenyl]-1,6-dimethyl-6-(1-methylpyrazol-4-yl)hexahydropyrimidine-2,4-dione and (6S)-3-[2,6-Difluoro-4-[2-(3-fluorophenyl)ethynyl]phenyl]-1,6-dimethyl-6-(1H-pyrazol-4-yl)hexahydropyrimidine-2,4-dione or a pharmaceutically acceptable salt or acid addition salt, a racemic mixture, or its corresponding enantiomer and/or optical isomer and/or stereoisomer thereof.

8. A compound of formula ID according to claim 1

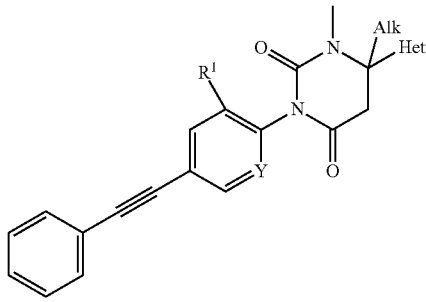

ID wherein
R¹ is Cl or F;
Y is CH or CCl;
Het is a 5-membered heteroaryl group, containing two or three heteroatoms, selected from N, O or S, optionally substituted by lower alkyl, lower alkoxyalkyl or lower alkyl substituted by hydroxyl;
Alk is lower alkyl;
or a pharmaceutically acceptable salt or acid addition salt, a racemic mixture, or its corresponding enantiomer and/or optical isomer and/or stereoisomer thereof.

9. A compound of formula ID according to claim 8, which is (6S)-3-[2-Chloro-4-(2-phenylethynyl)phenyl]-1,6-dimethyl-6-(1-methylpyrazol-4-yl)hexahydropyrimidine-2,4-dione or (6S)-3-[2-Chloro-6-fluoro-4-(2-phenylethynyl)phenyl]-1,6-dimethyl-6-(1-methyl pyrazol-4-yl)hexahydropyrimidine-2,4-dione or a pharmaceutically acceptable salt or acid addition salt, a racemic mixture, or its corresponding enantiomer and/or optical isomer and/or stereoisomer thereof.

10. A process for the manufacture of a compound of formula I of claim 1, which process comprises a) alkylating a compound of formula

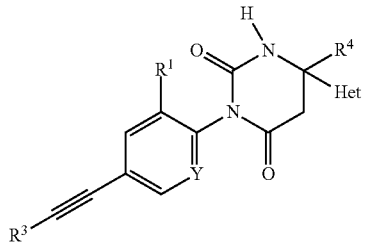

I-1 with R²—I in the presence of NaH or Cs₂CO₃ in DMF to form a compound of formula

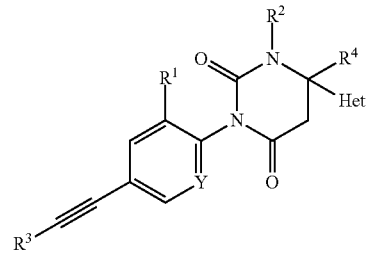

I-2 wherein R² is lower alkyl and the remaining substituents are described in claim 1, or if desired, converting the compound obtained into a pharmaceutically acceptable acid addition salt, or b) reacting a compound of formula 5

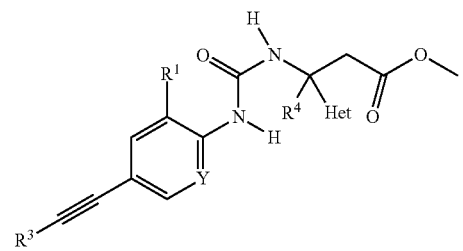

5 with NaH in THF or DMF
to form a compound of formula I-1

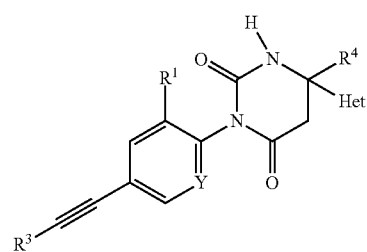

I-1 wherein the substituents are described in claim 1, or
if desired, converting the compound obtained into a pharmaceutically acceptable acid addition salt, or c) reacting a compound of formula 9

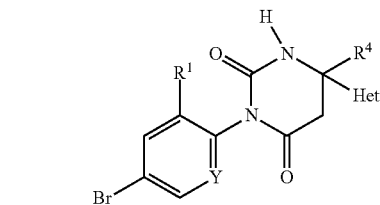

9 with a compound of formula

2 in the presence of Bis-(tpp)-Pd(II)Cl$_2$, Et3N, TPP, CUI in DMF or THF to form a compound of formula

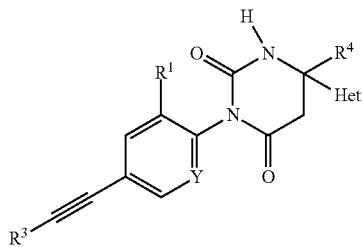

I-1 wherein the substituents are described in claim 1, or
if desired, converting the compound obtained into a pharmaceutically acceptable acid addition salt.

11. A pharmaceutical composition comprising a compound of formula I as in claim 1 or a pharmaceutically acceptable salt or acid addition salt, a racemic mixture, or its corresponding enantiomer and/or optical isomer and/or stereoisomer thereof, and a pharmaceutically acceptable excipient.

12. A method for the treatment of Parkinson's disease, anxiety, emesis, obsessive compulsive disorder, autism, neuroprotection, depression or diabetes type 2 in a patient, which method comprises administering to the patient an effective amount of a compound of formula I as in claim 1 or a pharmaceutically acceptable salt or acid addition salt, a racemic mixture, or its corresponding enantiomer and/or optical isomer and/or stereoisomer thereof.

* * * * *